(12) United States Patent
Cashman et al.

(10) Patent No.: US 11,492,325 B2
(45) Date of Patent: Nov. 8, 2022

(54) COMPOUNDS AS INHIBITORS OF SODIUM CHANNELS

(71) Applicant: Human BioMolecular Research Institute, San Diego, CA (US)

(72) Inventors: John R Cashman, San Diego, CA (US); Daniel J Ryan, El Segundo, CA (US); Karl Okolotowicz, Omaha, NE (US)

(73) Assignee: Human Biomolecular Research Institute, San Diego, CA (US)

( * ) Notice: Subject to any disclaimer, the term of this patent is extended or adjusted under 35 U.S.C. 154(b) by 0 days.

(21) Appl. No.: 16/343,395

(22) PCT Filed: May 31, 2017

(86) PCT No.: PCT/US2017/035328
§ 371 (c)(1),
(2) Date: Apr. 18, 2019

(87) PCT Pub. No.: WO2017/210371
PCT Pub. Date: Dec. 7, 2017

(65) Prior Publication Data
US 2019/0270696 A1    Sep. 5, 2019

Related U.S. Application Data

(60) Provisional application No. 62/392,399, filed on May 31, 2016.

(51) Int. Cl.
| | |
|---|---|
| C07C 213/02 | (2006.01) |
| C07C 217/58 | (2006.01) |
| A61P 9/06 | (2006.01) |
| A61P 25/08 | (2006.01) |
| C07D 213/64 | (2006.01) |
| C07D 213/65 | (2006.01) |
| C07D 213/68 | (2006.01) |
| A61K 35/12 | (2015.01) |
| A61K 31/138 | (2006.01) |
| A61K 31/44 | (2006.01) |
| A61K 35/545 | (2015.01) |
| A61K 45/06 | (2006.01) |

(52) U.S. Cl.
CPC .......... *C07C 217/58* (2013.01); *A61K 31/138* (2013.01); *A61K 31/44* (2013.01); *A61K 35/12* (2013.01); *A61K 35/545* (2013.01); *A61P 9/06* (2018.01); *A61P 25/08* (2018.01); *C07D 213/64* (2013.01); *C07D 213/65* (2013.01); *C07D 213/68* (2013.01); *A61K 45/06* (2013.01)

(58) Field of Classification Search
CPC .................................................. C07C 213/02
See application file for complete search history.

(56) References Cited

U.S. PATENT DOCUMENTS

| | | |
|---|---|---|
| 6,300,368 B1 | 10/2001 | Yamhashita et al. |
| 3,012,901 A1 | 9/2011 | Ortiz-Marciales et al. |
| 2003/0073724 A1 | 4/2003 | Shao et al. |

FOREIGN PATENT DOCUMENTS

WO    2017210371 A3    1/2018

OTHER PUBLICATIONS

Franchini, C., et al. "Optically Active Mexiletine Analogues as Stereoselective Blockers of Voltage-Gated Na+ Channels." J. Med. Chem. (2003), vol. 46, pp. 5238-5248. (Year: 2003).*
Roselli, M., et al. "Synthesis, antiarrhythmic activity, and toxicological evaluation of mexiletine analogues." European Journal of Medicinal Chemistry. (2016), vol. 121, pp. 300-307. (Year: 2016).*
Drug (Tiwari, G., et al. "Drug delivery systems: An updated review." Int J Pharm Investig. (Jan.-Mar. 2012), vol. 2, Issue 1, pp. 2-11). (Year: 2012).*
Leeming, Michael G., et al. "High-Resolution Twin-Ion Metabolite Extraction (HiTIME) Mass Spectrometry: Nontargeted Detection of Unknown Drug Metabolites by Isotope Labeling, Liquid Chromatography Mass Spectrometry, and Automated High-Performance Computing." Anal. Chem. (2015), vol. 87, 4104-4109. (Year: 2015).*
Franchini, C. et al., "Optically active mexiletine analogues as stereoselective blockers of voltage-gated Na+ channels", Journal of Medicinal Chemistry, 2003, vol. 46, No. 24, pp. 5238-5248.
Huang, K. et al., "Spiroborate ester-mediated asymmetric synthesis of beta-hydroxy esters and is conversion to highly enantiopure beta-amino ethers", Journal of Organic Chemistry, 2009, vol. 74, No. 11, pp. 4195-4202.
PCT/US2017/035328 International Preliminary Report on Patentability and Written Opinion of the International Searching Authority dated Nov. 27, 2017.
Altman, A. et al., "Novel Purine Nitrile Derived Inhibitors of the Cysteine Protease Cathepsin K", Journal of Medicinal Chemistry, 2004, vol. 47, pp. 5833-5836.
Carrieri, A. et al.,"2D- and 3D-QSAR of Tocainide and Mexiletine Analogues Acting as Nav12.4 channel blockers", European Journal of Medicinal Chemistry, 2009, vol. 44, pp. 1477-1485.
Cashman, J.R. et al. "N-Oxygenation of Amphetamine and Methamphetamine by the Human Flavin-Containing Monooxygenease (Form 3): Role in Bioactivation and Detoxification", The Journal of Pharmacology and Experimental Therapeutics, 1999, vol. 288, No. 3, pp. 1251-1260.

(Continued)

*Primary Examiner* — John S Kenyon
(74) *Attorney, Agent, or Firm* — Angelo Castellino

(57) ABSTRACT

Methods and small molecule compounds for inhibition of sodium channels are provided. One example of a class of compounds that may be used is represented by the compound of Formula (I) or a pharmaceutically acceptable salt, N-oxide or solvate thereof, wherein A, B, D, R, $R_1$, $R'_1$, $R_2$, $R_3$, $R_4$, $R_5$, $R_6$, $R_7$, $R_8$ are as described herein.

21 Claims, 2 Drawing Sheets

(56) References Cited

OTHER PUBLICATIONS

Cashman, J.R. "Role of Flavin-Containing Monooxygenases in Drug Development", Expert Opinion Drug Metabolism and Toxicology, 2008, vol. 4, No. 12, pp. 1507-1521.
Catalano, A. et al., "Mexiletine Metabolites: A Review", 2015, vol. 22, pp. 1400-1413.
De Luca, A., et al. "Molecular Determinants of Mexiletine Structure for Potent and Use-Dependent Block of Skeletal Muscle Sodium Channels" Molecular Pharmacology, 2000, vol. 57, pp. 268-277.
Lin, J. and Cashman, J.R. "N-Oxygenation of Phenethylamine to the trans-Oxime by Adult Human Liver Flavin-Containing Monooxygenase and Retrreduction of Phenethylamine Hydroxylamine by Human Liver Microsomes" The Journal of Pharmacology and Experimental Therapeutics, 1996, vol. 282, No. 3, pp. 1269-1279.
Lin, J. and Cashman, J.R., "Detoxification of Tyramine by the Flavin-Containing Monooxygenase: Seteroselective Formation of the trans-Oxime", Chemical Research in Toxicology, 1997, vol. 10, pp. 842-852.
Nakajima, M., et al. "Involvement of CYP1A2 in Mexiletine Metabolism", British Journal of Clinical Pharmacology, 1998, vol. 46, pp. 55-62.
White, D.E., "A Broadly Applicable and Practical Oligomeric (salen)Co Catalyst for Enantioselective Epoxide Ring-Opening Reactions", Tetrahedron, 2014, vol. 70, pp. 4165-4180.

\* cited by examiner

COMPOUNDS AS INHIBITORS OF SODIUM CHANNELS

CROSS-REFERENCE TO RELATED APPLICATIONS

The present application is a national phase filing under 35 USC § 371 of International Patent Application No. PCT/US2017/0355328, filed May 31, 2017, now expired, which claims the benefit under 35 USC § 119(e) of U.S. Provisional Application Ser. No. 62/392,399, filed May 31, 2016, the disclosures of which are incorporated by reference herein in their entireties for all purposes.

GRANT INFORMATION

This invention was not made with Federal government support.

FIELD OF THE DISCLOSURE

The disclosure relates generally to small molecule compounds and more specifically to derivatives of stereochemically defined phenoxy propan-2 amines and deuterated analogs for their use in cardiovascular and central nervous system diseases.

BACKGROUND OF THE DISCLOSURE

Cardiovascular disease is a leading cause of deaths in the United States. For example, heart attacks are the leading cause of death in men and women in the United States during 2010 with a total economic impact of $40 B/year. 50% of individuals over the age of 65 suffering heart attacks die within 5 years of a heart attack. Despite this prevalence, options are limited. Treating arrhythmia in individuals before or after heart attacks and arrhythmia with Long QT (LQT) prolongation is also an unmet need. Thus, there is a major unmet medical need for the development of selective and inexpensive targeted treatments for cardiovascular disease.

The blockade of voltage gated sodium channels that inhibits the generation and propagation of an action potential is the mechanism that local anesthetics, antiarrhythmics and anticonvulsants prevent pathological firing of action potentials in excitable tissues. For example, Mexiletine, a well-established orally effective antiarrhythmic drug of the IB class is effective in treatment of muscular hyperexcitability of myotonic syndromes including ones with abnormal membrane excitability and delayed muscle relaxation after voluntary contraction. Sodium channel myotonias, paramyotonia congenital and hyperkaliemic periodic paralysis and epilepsy are among many diseases related to sodium channel mutations. The therapeutic effect of Mexiletine is directly associated with its ability to block voltage-dependent sodium channels present in cardiac and skeletal muscle fibers. Use-dependent blockers of sodium channels stabilize the channels in the inactivated state and allows a greater potency on tissues characterized by excessive excitability including myotonic muscles with non-physiological phenotypes of sodium or chloride channels. The on and off rate of binding to the sodium channel determines the efficacy of the drug as well as the relative degree of toxicity. If the molecule binds too long, this interferes with sodium channel excitability. For Mexiletine, the potency of blocking the sodium channel can be correlated to lipophilicity of the molecule. The sodium channel target of Mexiletine that has a center of chirality has shown moderate or low stereoselectivity.

Mexiletine has shown clinical utility to decrease abnormal sodium channel discharges in myotonic syndromes. Mexiletine is the leading agent to treat cardiovascular disease in dogs. Despite the promise, Mexiletine has significant drawbacks. For example, the dose used for anti-myotonic effects are as great as those for exerting antiarrhythmic effects and can induce or worsen conduction defects. In addition, at the relatively elevated doses and multiple administrations due to its clearance required for therapeutic action, Mexiletine can have side effects on the central nervous system. Electrophysiological and biochemical evidence points to block of sodium channels in the central nervous system. For example, local anesthetics inhibits batrachotoxin A 20-alpha-benzoate and alters stereoselective binding of cocaine to sodium channels in the brain. After administration to animals, Mexiletine causes seizures and nausea. Thus, because the recommended dose to treat arrhythmia and myotonic patients are in the same range, adverse effects on both the cardiac and central nervous system are possible. Selective stimulation of different sodium channels may have utility for CNS diseases or seizures. In addition to effects on sodium channels, Mexiletine and other related drugs possess off-target effects on the potassium channel.

Despite the fact Mexiletine is a very old drug, little work has been done to re-engineer Mexiletine to remove side effects. For example, Class Ic anti-arrhythmics were examined in the CAST and CAST II studies. The results showed that treating patients with Class Ic sodium channel blockers post MI decreased arrhythmia in the short term, but led to greater instances of arrhythmia-related deaths in the long term. Class Ic anti-arrhythmics were chosen because other anti-arrhythmics (i.e., Class Ia and Ibs including Mexiletine) had been shown to not suppress arrhythmia or had adverse effects that precluded their use. In the current clinical setting sodium channel blockers are not used for the treatment of arrhythmia.

What is needed is a more potent compound with greater potency against on-target sites and less potency against off-target sites. For example, a desirable improvement on Mexiletine would be to optimize the use dependence and the refractory period effect or decrease the inhibition of potassium (hERG) channel effects. The basis for effecting this could be changing the 3D structure or introducing new pharmaceutical properties. Until our work, no phenotypic cell-based assay was available to discern these effects. Arrhythmogenic agents can be identified in normal and LQT3 human patient-derived cardiomyocytes using a voltage-sensitive kinetic imaging cytometry assay. A phenotypic screen in human cardiomyocytes provided powerful information to ascertain on-target and off-target effects in highly relevant human cells. Important metrics of compound efficacy and safety were obtained including: action potential delay (APD) shortening (i.e., $IC_{50}$ for on-target effects), APD prolongation (i.e., $IC_{50}$ for off-target effects), early after depolarizations (EADs that provide evidence of arrhythmogenicity) and cessation of beating (i.e., a marker of acute arrhythmogenicity/toxicity). Concurrent evaluation of these metrics underscores the value of this approach using a whole-cell physiological approach. Results from our work provided several new compounds that showed significantly less arrhythmogenicity than Mexiletine in normal and LQT3 patient-derived cardiomyocytes. Compounds evaluated by electrophysiology confirmed and extended the results. Together, these data showed that chemical modifications to different portions of the parent Mexiletine decreased arrhythmogenic liability while modifications elsewhere affected on- and off-target effects. For example, unexpected selectivity on sodium and potassium channel inhibition by Mexiletine analogs was observed due to novel substituents. Also, unanticipated decrease in metabolism was observed by moving certain substituents or deuteration of Mexiletine likely due to unexpected changes in regioselective metabolism or structural aspects.

Mexiletine is relatively rapidly metabolized by hepatic enzymes and is relatively rapidly cleared in vivo. Multiple doses of Mexiletine are required for human efficacy because of metabolism, clearance and toxicity. Replacement of metabolically labile C—H bonds with metabolically less labile groups containing C—Cl or C—F or C-D or C—$CF_3$ or C-aryl or C-cyclopropyl groups afforded more bioavailable compounds. Compounds were chemically ($t_{1/2}$>30 days) and metabolically (hepatic microsomes+NADPH) stable (human $t_{1/2}$, >60 min). In contrast to Mexiletine, select compounds showed no acute toxicity in mice in vivo. In a (24 hour) toxicity study, compounds administered to mice (100 or 200 mg/kg, (i.p.) did not produce seizures. In contrast, Mexiletine-treated animals (100 or 200 mg/kg, i.p.) showed death, seizures and other behavior issues. The $LD_{50}$ for Mexiletine (114 mg/kg, i.p.) in mice shows the therapeutic window is narrow. In contrast, analogs were non-toxic and well-tolerated in vivo.

Compounds described herein are drug-like small molecules and have characteristics that make them very attractive small molecules drugs. For example, analogs formulated as salts have excellent aqueous solubility and improved bioavailability, are chemically and metabolically stable and are non-toxic and highly potent and selective sodium channel inhibitors.

SUMMARY OF THE DISCLOSURE

In one aspect, the disclosure provides a nontoxic compound of Formula I or stereoisomers or a pharmaceutically acceptable salt, N-oxide or solvate capable of selectively inhibiting sodium channels:

A compound of Formula I:

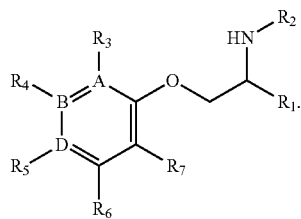

(I)

or a stereoisomer, tautomer, isotope, or salt or thereof, wherein:

A, B, D are independently Carbon or Nitrogen;

$R_1$ is selected from the group consisting of hydrogen, deuterium, methyl, trideuteromethyl, ($C_2$-$C_6$)alkyl, ($C_3$-$C_6$)cycloalkyl, ($C_6$-$C_{24}$)aryl, and ($C_5$-$C_{24}$)heteroaryl, wherein ($C_6$-$C_{24}$)aryl and ($C_6$-$C_{24}$)heteroarl are optionally substituted with 1 to 5 $R_8$ substituents independently selected from the group consisting of deuterium, halo, methyl, trideuteromethyl, trifluoromethyl, 2,2,2-trifluoroethyl, ($C_2$-$C_6$)alkyl, ($C_3$-$C_6$)cycloalkyl, ($C_1$-$C_6$)alkyloxy, ($C_3$-$C_6$)cycloalkyloxy, amino, ($C_1$-$C_6$)alkylamino, di-($C_1$-$C_6$)alkylamino, ($C_6$-$C_{24}$)arylamino, cyano, nitro, and ($C_1$-$C_6$)alkylsulfonyl;

$R_2$ is selected from the group consisting of hydrogen, deuterium, methyl, trideuteromethyl, trifluoromethyl, 2,2,2-trifluoroethyl, ($C_2$-$C_6$)alkyl, ($C_3$-$C_6$)cycloalkyl, ($C_3$-$C_6$)cycloheteroalkyl, 2-($C_1$-$C_6$)alkoxyethyl, 2-hydroxyethyl, 2-($C_6$-$C_{24}$)aryloxyethyl, bis(2-methoxyethyl), ($C_1$-$C_6$) alkoxymethyl, 2-($C_3$-$C_6$)cycloalkoxyethyl, ($C_6$-$C_{24}$)aryl, and ($C_6$-$C_{24}$)heteroaryl, wherein ($C_6$-$C_{24}$)aryl and ($C_6$-$C_{24}$) heteroaryl are optionally substituted with 1 to 5 $R_8$ substituents selected from the group consisting of deuterium, halo, methyl, trideuteromethyl, trifluoromethyl, 2,2,2-trifluoroethyl, ($C_2$-$C_6$)alkyl, ($C_3$-$C_6$)cycloalkyl, ($C_1$-$C_6$)alkyloxy, ($C_3$-$C_6$)cycloalkyloxy, amino, ($C_1$-$C_6$)alkylamino, di-($C_1$-$C_6$)alkylamino, ($C_6$-$C_{24}$)arylamino, cyano, nitro and and ($C_1$-$C_6$)alkylsulfonyl;

$R_3$ is absent if A is Nitrogen, or if A is Carbon $R_3$ is selected from the group consisting of hydrogen, deuterium, halo, methyl, trideuteromethyl, trifluoromethyl, 2,2,2-trifluoroethyl, ($C_2$-$C_6$)alkyl, ($C_3$-$C_6$)cycloalkyl, ($C_1$-$C_6$)alkyloxy, ($C_3$-$C_6$)cycloalkyloxy, amino, ($C_1$-$C_6$)alkylamino, di-($C_1$-$C_6$)alkylamino, ($C_6$-$C_{24}$)arylamino, cyano, nitro, and ($C_1$-$C_6$)alkylsulfonyl;

$R_4$ is absent if B is Nitrogen, or if B is Carbon $R_4$ is selected from the group consisting of hydrogen, deuterium, halo, methyl, trideuteromethyl, trifluoromethyl, 2,2,2-trifluoroethyl, ($C_2$-$C_6$)alkyl, ($C_3$-$C_6$)cycloalkyl, ($C_1$-$C_6$)alkyloxy, ($C_3$-$C_6$)cycloalkyloxy, amino, ($C_1$-$C_6$)alkylamino, di-($C_1$-$C_6$)alkylamino, ($C_6$-$C_{24}$)arylamino, cyano, nitro, and ($C_1$-$C_6$)alkylsulfonyl;

$R_5$ is absent if D is Nitrogen, or if D is Carbon $R_5$ is a substituent selected from the group consisting of hydrogen, deuterium, halo, methyl, trideuteromethyl, trifluoromethyl, 2,2,2-trifluoroethyl, ($C_2$-$C_6$)alkyl, ($C_3$-$C_6$)cycloalkyl, ($C_1$-$C_6$)alkyloxy, ($C_3$-$C_6$)cycloalkyloxy, amino, ($C_1$-$C_6$)alkylamino, di-($C_1$-$C_6$)alkylamino, ($C_6$-$C_{24}$)arylamino, cyano, nitro, and ($C_1$-$C_6$)alkylsulfonyl;

$R_6$ and $R_7$ are independently selected from the group consisting of hydrogen, deuterium, halo, methyl, trideuteromethyl, trifluoromethyl, 2,2,2-trifluoroethyl, ($C_2$-$C_6$)alkyl, ($C_3$-$C_6$)cycloalkyl, ($C_1$-$C_6$)alkyloxy, ($C_3$-$C_6$)cycloalkyloxy, amino, ($C_1$-$C_6$)alkylamino, di-($C_1$-$C_6$)alkylamino, ($C_6$-$C_{24}$) arylamino, cyano, nitro, and ($C_1$-$C_6$)alkylsulfonyl.

$R_1$ is independently substituted S and/or R isomeric forms and/or racemic forms and can also be substituted with a deuterium at the center of chirality.

In another aspect the disclosure provides methods for stereoselectively synthesizing compounds inhibiting sodium channels, comprising contacting cells with a aryloxy propan-2-amine-based compound of Formula I in the form of a free base or a pharmaceutically acceptable salt, prodrug, hydrate, solvate or N-oxide thereof, wherein A, B, D, R, $R_1$-$R_6$, are as described above.

In another aspect the disclosure provides methods for stereoselectively inhibiting sodium channels, comprising contacting cells with a aryloxy propan-2-amine-based compound of Formula I in the form of a free base or a pharmaceutically acceptable salt, prodrug, hydrate, solvate or N-oxide thereof, wherein A, B, D, R, $R_1$-$R_6$, are as described above.

DETAILED DESCRIPTION OF THE DISCLOSURE

Figure 1:
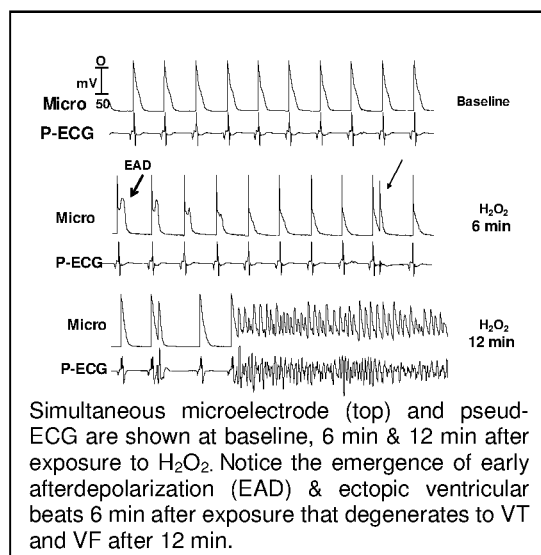
FIG. 1. Initiation of Early After Depolarizations-Mediated Ectopic Ventricular Beats and Ventricular Fibrillation in an Isolated Perfused Aged Rat Heart Exposed to hydrogen peroxide.

The following terms, definitions and abbreviations apply. Abbreviations used herein have their conventional meaning within the chemical and biological arts.

The term "lipophilic" refers to moieties having an affinity for lipids and other fat-like substances, tending to combine with, and capable of dissolving, them.

The term "sodium channels" refers to voltage-dependent sodium channels in cells.

The term "mutant sodium channels" refers to variant sodium channels in cells with traits associated with abnormal or pathophysiologic behavior.

The term "myotonia" refers to a condition of cellular hyperexcitability and abnormal membrane excitability and delayed muscle relaxation after voluntary contraction, where the cells have lost specific structural, functional, and biochemical cell-cycle checkpoints.

The term "patient" refers to organisms to be treated by the methods of the disclosure. Such organisms include, but are not limited to humans or other animals. In the context of the disclosure, the term "subject" generally refers to an individual who will receive or who has received treatment described below (e.g., administration of the compounds of the disclosure, and optionally one or more additional therapeutic agents).

Where substituent groups are specified by their conventional chemical formula, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain, or cyclic hydrocarbon radical, or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclopropyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent radical derived from an alkyl, as exemplified, but not limited, by —CH$_2$CH$_2$CH$_2$CH$_2$—, —CH$_2$CH═CHCH$_2$—, —CH$_2$CCCH$_2$—, —CH$_2$CH$_2$CH(CH$_2$CH$_2$CH$_3$)CH$_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms. The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, —CH═CH—N(CH$_3$)—CH$_3$, O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclopropyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings, which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent radicals of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g., "3 to 7 membered"), the term "member" refers to a carbon or heteroatom.

The term "oxo or keto" as used herein means an oxygen that is double bonded to a carbon atom.

The terms "heterocycle" and "heterocyclic" refer to a monovalent unsaturated group having a single ring or multiple condensed rings, from 1 to 8 carbon atoms and from 1 to 4 heteroatoms, for example, nitrogen, sulfur or oxygen within the ring.

The term "methylthio" refers to a moiety —S—CH$_3$. Sulfonyl refers to S-oxide.

The term "sulfonamide" refers to compound A shown below, as well as to the other

R—SO$_2$—N—R$_2$          A moieties derived from compound A: The terms "furyl," "tetrahydrofuryl," and "pyridyl" refer to radicals formed by removing one hydrogen from the molecules of furan, tetrahydrofuran, and pyridine, respectively.

The terms "alkyl amine" and "cyclic amine" refer to alkanes or cycloalkanes, respectively, having one hydrogen substituted by a primary, secondary or tertiary amino group, as well as to the moieties and radicals derived from such amines.

The term "alkyl amide" refers to alkanes, having one hydrogen substituted by a primary, secondary or tertiary amino group.

Each of above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O) CH$_3$, —C(O) CF$_3$, —C(O) CH$_2$O CH$_3$, and the like).

The term "alkoxy" refers to the moiety —O-alkyl, wherein alkyl is as defined above. Examples of alkoxy structures that are within the purview of the definition include, but are not limited to, (C$_1$-C$_6$)alkoxy radicals, such as methoxy, ethoxy, propoxy, isopropoxy, butoxy, iso-butoxy, sec-butoxy, tert-butoxy, pentoxy, 3-pentoxy, or hexyloxy.

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'", —S(O)R', —S(O)$_2$R', —S(O)$_2$NR'R", —NR SO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R", R'" and R"" are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')q-U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)r-B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' are independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), or silicon (Si).

An "aminoalkyl" as used herein refers to an amino group covalently bound to an alkylene linker. The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

A "substituent group," as used herein, means a group selected from the following moieties: (A) —OH, —NH$_2$, —SH, —CN, —CF$_3$, —NO$_2$, —S(O)-alkyl, —S(O)-aryl, —S(O$_2$)-alkyl, S(O$_2$)-aryl, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from: (i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from: (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

In the examples, we categorized the effects of 1 on biological assays as follows: ++++, $IC_{50}$ 0-10 μM; +++, $IC_{50}$ 10-50 μM; ++, $IC_{50}$ 50-100 μM; +, $IC_{50}$>100 μM; NR, no response.

The compounds of the disclosure may exist as salts. Examples of applicable salt forms include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When the disclosed compounds contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the disclosure contain both basic and acidic functionalities that allow the compounds to be converted into either base or acid addition salts.

The term "pharmaceutically acceptable salts" is meant to include salts of active compounds which are prepared with relatively nontoxic acids or bases, depending on the particular substituent moieties found on the compounds described herein. When compounds of the disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the disclosure can exist in unsolvated forms as well as solvated forms, including hydrated forms. In general, the solvated forms are equivalent to unsolvated forms and are encompassed within the scope of the disclosure. Certain compounds of the disclosure may exist in multiple crystalline or amorphous forms. In general, all physical forms are equivalent for the uses contemplated by and are intended to be within the scope of the disclosure.

Certain compounds of the disclosure possess centers of chirality (e.g., asymmetric carbon atoms), optical or chiral centers or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the disclosure. The compounds of the disclosure do not include those which are known in art to be too unstable to synthesize and/or isolate. The disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another. It will be apparent to one skilled in the art that certain compounds of the disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each center of chirality (e.g., an asymmetric carbon center). Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the disclosure.

The compounds of the disclosure may also contain unnatural proportions of atomic isotopes at one or more atoms that constitute such compounds. For example, the compounds may be radiolabeled with radioactive isotope, such as for example, tritium ($^{3}$H), iodine-125 ($^{125}$I) or carbon-14 ($^{14}$C). All isotopic variations of the compounds of the disclosure, whether radioactive or not, are encompassed within the scope of the disclosure. Nonradioactive isotopes include deuterium ($^{2}$H), carbon-13 ($^{13}$C) and nitrogen-15 ($^{15}$N).

In addition to salt forms, the disclosure provides compounds, which are in a prodrug form. Prodrugs of the compounds described herein are those compounds that readily undergo chemical or metabolism-mediated changes under physiological conditions to provide the compounds of the disclosure. For example, a phosphate or other ester moiety or other prodrug moiety may be independently attached to $R_1$-$R_6$). Additionally, prodrugs can be converted to the compounds of the disclosure by chemical or biochemical methods in an ex vivo environment. For example, prodrugs can be slowly converted to the compounds of the disclosure when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" in reference to a particular disease includes prevention of the disease.

The disclosure also provides articles of manufacture comprising packaging material and a pharmaceutical composition contained within said packaging material, wherein said packaging material comprises a label which indicates that said pharmaceutical composition can be used for treatment of disorders and wherein said pharmaceutical composition comprises a compound according to the disclosure.

The disclosure also provides pharmaceutical compositions comprising at least one compound in an amount effective for treating a disorder, and a pharmaceutically acceptable vehicle or diluent. The compositions of the disclosure may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the disclosure may be formulated into therapeutic compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like. Salts of the disclosure include amine salts formed by the protonation of an amino group with inorganic acids such as hydrochloric acid, hydrobromic acid, hydroiodic acid, sulfuric acid, phosphoric acid, and the like. Salts of the disclosure may also include amine salts formed by the protonation of an amino group with suitable organic acids, such as p-toluenesulfonic acid, acetic acid, and the like. Additional excipients which are contemplated for use in the practice of the disclosure are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference. In addition, polymorphs, hydrates, and solvates of the compounds are included in the disclosure.

The disclosed pharmaceutical compositions may be administered by any suitable means, for example, orally, such as in the form of tablets, capsules, granules or powders; sublingually; buccally; parenterally, such as by subcutaneous, intravenous, intramuscular, intrathecal, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally or with cavitands (i.e., Captisol).

In addition to primates, such as humans, a variety of other mammals can be treated according to the method of the disclosure. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The term "therapeutically effective amount" means the amount of the compound or pharmaceutical composition that will elicit the biological or medical response of a tissue, system, animal or human that is being sought by the researcher, veterinarian, medical doctor or other clinician, e.g., restoration or maintenance of vasculostasis or prevention of the compromise or loss or vasculostasis; reduction of tumor burden; reduction of morbidity and/or mortality.

By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the disclosure or pharmaceutical composition to the subject in need of treatment. The term "contacting" should be understood to mean providing a compound of the disclosure or pharmaceutical composition either in vitro or in vivo.

The pharmaceutical compositions for the administration of the compounds of this embodiment either alone or in combination with other agents, may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of disease. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Also useful as a solubilizer is polyethylene glycol, for example. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent or cosolvent or complexing agent or dispersing agent or excipient or combination thereof, for example 1,3-butane diol, polyethylene glycols, polypropylene glycols, ethanol or other alcohols, povidones, Tweens, sodium dodecyle sulfate, sodium deoxycholate, dimethylacetamide, polysorbates, poloxamers, cyclodextrins, e.g., sulfobutyl ether O-cyclodextrin, Captisol, lipids, and excipients such as inorganic salts (e.g., sodium chloride), buffering agents (e.g., sodium citrate, sodium phosphate), and sugars (e.g., saccharose and dextrose). Among the acceptable vehicles and solvents that may be employed are water, dextrose solutions, Ringer's solutions and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

Depending on the condition being treated, these pharmaceutical compositions may be formulated and administered systemically or locally. Suitable routes may, for example, include oral or transmucosal administration; as well as parenteral delivery, including intramuscular, subcutaneous, intramedullary, intrathecal, intraventricular, intravenous, intraperitoneal, or intranasal administration. For injection, the pharmaceutical compositions of the disclosure may be formulated in aqueous solutions, for example, in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

The compounds of the disclosure may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. For topical use, creams, ointments, jellies, solutions or suspensions, etc., containing the compounds of the disclosure are employed. For purposes of this application, topical application shall include mouthwashes and gargles.

In the methods described herein, an appropriate dosage level will generally be about 0.01 to 500 mg per kg patient body weight per day which can be administered in single or multiple doses. The dosage level can be about 0.01 to about 250 mg/kg per day, such as 0.01 to about 100 mg/kg per day, for example, 0.01 to about 10 mg/kg per day, such as 0.04 to about 5 mg/kg per day, or about 0.5 to about 100 mg/kg per day. A suitable dosage level may be also about 0.05 to 100 mg/kg per day, or about 0.1 to 50 mg/kg per day or 1.0 mg/kg per day. Within this range the dosage may be 0.05 to 0.5, 0.5 to 5 or 5 to 50 mg/kg per day for example. The Examples section shows that one of the exemplary compounds was dosed at 30 mg/kg/day and also at about 100 mg/kg/day. For oral administration, the compositions may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or once or twice per day. There may be a period of no administration followed by another regimen of administration. Administration of the compounds may be closely associated with the schedule of a second agent of administration.

It will be understood, however, that the specific dose level and frequency of dosage for any particular patient may be varied and will depend upon a variety of factors including the potency of the specific compound employed, the metabolic stability and length of action of that compound, the age, body weight, general health, gender, diet, mode and time of administration, rate of excretion, drug combination, the severity of the particular condition, and the host undergoing therapy.

Thus, in one embodiment the disclosure provides a compound of Formula I or stereoisomers or a pharmaceutically acceptable salt, prodrugs, N-oxide or solvate capable of inhibiting sodium channels:

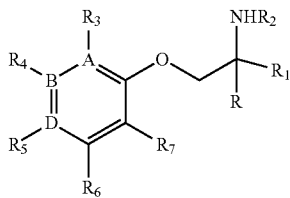

Formula I

A, B, D are independently Carbon, Nitrogen. R, $R_1$, $R_2$, $R_3$, $R_4$, $R_5$=H, deuterium, alkyl, aryl, halo, O-alkyl, O-aryl, N-alkyl, N,N-dialkyl, N-aryl, N,N-diaryl, S—, S-aryl, S(O)-alkyl, S(O)-aryl, S(O$_2$)-alkyl, S(O$_2$)-aryl, cycloalkyl, cycloheteroalkyl, heteroaryl.

R is independently substituted hydrogen, deuterium, trideuteromethyl, (C$_1$-C$_6$)alkyl, aryl, halogen, CF$_3$, C$_2$F$_5$, O-alkyl, N-alkyl, O-aryl, —(CH$_2$)$_{1-6}$OH, —(CH$_2$)$_{1-6}$SH, —(CH$_2$)$_{1-6}$NH$_2$, —(CH$_2$)$_{1-6}$OR$_{11}$, —(CH$_2$)$_{1-6}$SR$_{11}$, —(CH$_2$)$_{1-6}$N(R$_{11}$)$_2$. where R$_{11}$ is independently substituted hydrogen, (C$_1$-C$_6$)alkyl, aryl, CF$_3$, C$_2$F$_5$, hydroxyl, O-alkyl, O-aryl, cycloalkyl(C$_1$-C$_6$), alkyl(C$_1$-C$_6$)amine, alkyl cyclic (C$_1$-C$_6$)amine, alkyl(C$_1$-C$_6$) N,N-dialkylamino, alkyl (C$_1$-C$_6$)aryl amine, cycloheteroalkyl, heteroaryl, methylcycloalkyl(C$_1$-C$_6$), methylaryl, methylcycloheteroalkyl, methylheteroaryl, methylcyclopropyl, or a moiety forming a salt; or unsubstituted phenyl, substituted or unsubstituted pyridine, wherein phenyl or pyridine is optionally independently substituted with 1 to 3 independently substituted; or a moiety forming a salt;

$R_1$ is independently substituted hydrogen, deuterium, trideuteromethyl, (C$_1$-C$_6$)alkyl, aryl, halogen, CF$_3$, C$_2$F$_5$, O-alkyl, N-alkyl O-aryl, —(CH$_2$)$_{1-6}$OH, —(CH$_2$)$_{1-6}$SH, —(CH$_2$)$_{1-6}$NH$_2$, —(CH$_2$)$_{1-6}$OR$_{11}$, —(CH$_2$)$_{1-6}$SR$_{11}$, —(CH$_2$)$_{1-6}$N(R$_{11}$)$_2$. where R$_{11}$ is independently substituted hydrogen, (C$_1$-C$_6$)alkyl, aryl, CF$_3$, C$_2$F$_5$, hydroxyl, O-alkyl, O-aryl, cycloalkyl(C$_1$-C$_6$), alkyl(C$_1$-C$_6$)amine, alkyl cyclic (C$_1$-C$_6$)amine, alkyl(C$_1$-C$_6$) N,N-dialkylamino, alkyl (C$_1$-C$_6$)aryl amine, cycloheteroalkyl, heteroaryl, methylcycloalkyl(C$_1$-C$_6$), methylaryl, methylcycloheteroalkyl, methylheteroaryl, methylcyclopropyl, or a moiety forming a salt; or unsubstituted phenyl, substituted or unsubstituted pyridine, wherein phenyl or pyridine is optionally independently substituted with 1 to 3 independently substituted; or a moiety forming a salt;

$R_2$ is independently substituted hydrogen, deuterium, trideuteromethyl, O, O$_2$, (C$_1$-C$_6$)alkyl, aryl, CF$_3$, C$_2$F$_5$, hydroxyl, O-alkyl, O-aryl, cycloalkyl(C$_1$-C$_6$), alkyl(C$_1$-C$_6$) amine, alkyl cyclic(C$_1$-C$_6$)amine, alkyl(C$_1$-C$_6$) N,N-dialkylamino, alkyl (C$_1$-C$_6$)aryl amine, cycloheteroalkyl, heteroaryl, methylcycloalkyl(C$_1$-C$_6$), methylaryl, methylcycloheteroalkyl, methylheteroaryl, methylcyclopropyl, or a moiety forming a salt; or unsubstituted phenyl, substituted or unsubstituted pyridine, wherein phenyl or pyridine is optionally independently substituted with 1 to 3 independently substituted;

$R_3$ is independently substituted hydrogen, deuterium, trideuteromethyl, (C$_1$-C$_6$)alkyl, aryl, halogen, CF$_3$, C$_2$F$_5$, O-alkyl, O-aryl, S-alkyl, S-aryl, amine, cyclic amine, aryl amine or a moiety forming a salt;

$R_4$ is independently substituted hydrogen, deuterium, trideuteromethyl, (C$_1$-C$_6$)alkyl, aryl, halogen, CF$_3$, C$_2$F$_5$, O-alkyl, O-aryl, S-alkyl, S-aryl, S(O)-alkyl, S(O)-aryl, S(O$_2$)-alkyl, S(O$_2$)-aryl, amine, cyclic amine, aryl amine or a moiety forming a salt;

$R_5$ is independently substituted hydrogen, deuterium, (C$_1$-C$_6$)alkyl, aryl, halogen, CF$_3$, C$_2$F$_5$, hydroxyl, O-alkyl, O-aryl, S-alkyl, S-aryl, S(O)-alkyl, S(O)-aryl, S(O$_2$)-alkyl, S(O$_2$)-aryl, cycloalkyl(C$_1$-C$_6$), alkyl(C$_1$-C$_6$)amine, alkyl cyclic(C$_1$-C$_6$)amine, alkyl(C$_1$-C$_6$) N,N-dialkylamino, alkyl (C$_1$-C$_6$)aryl amine, cycloheteroalkyl, heteroaryl, methylcycloalkyl(C$_1$-C$_6$), methylaryl, methylcycloheteroalkyl, methylheteroaryl, methylcyclopropyl, or a moiety forming a salt; or unsubstituted phenyl, substituted or unsubstituted pyridine, wherein phenyl or pyridine is optionally independently substituted with 1 to 3 independent substitutes, O-alkyl, O-aryl, amino, N-alkylamino, N-arylamino, or hydroxyl or amino prodrug moieties;

$R_6$ is independently substituted hydrogen, deuterium, trideuteromethyl, (C$_1$-C$_6$)alkyl, aryl, halogen, CF$_3$, C$_2$F$_5$, O-alkyl, N-alkyl O-aryl, —(CH$_2$)$_{1-6}$OH, —(CH$_2$)$_{1-6}$SH, —(CH$_2$)$_{1-6}$NH$_2$, —(CH$_2$)$_{1-6}$OR$_{11}$, —(CH$_2$)$_{1-6}$SR$_{11}$, —(CH$_2$)$_{1-6}$N(R$_{11}$)$_2$. where R$_{11}$ is independently substituted hydrogen, (C$_1$-C$_6$)alkyl, aryl, CF$_3$, C$_2$F$_5$, hydroxyl, O-alkyl, O-aryl, cycloalkyl(C$_1$-C$_6$), alkyl(C$_1$-C$_6$)amine, alkyl cyclic (C$_1$-C$_6$)amine, alkyl(C$_1$-C$_6$) N,N-dialkylamino, alkyl (C$_1$-C$_6$)aryl amine, cycloheteroalkyl, heteroaryl, methylcycloalkyl(C$_1$-C$_6$), methylaryl, methylcycloheteroalkyl, methylheteroaryl, methylcyclopropyl, or a moiety forming a salt; or unsubstituted phenyl, substituted or unsubstituted pyridine, wherein phenyl or pyridine is optionally independently substituted with 1 to 3 independently substituted; or a moiety forming a salt;

R is independently substituted S and/or R isomeric forms and/or racemic forms,

In another aspect the disclosure provides methods for stereoselectively synthesizing compounds inhibiting sodium channels, comprising contacting cells with a aryloxy propan-2-amine-based compound of Formula I in the form of a free base or a pharmaceutically acceptable salt, prodrug, hydrate, solvate or N-oxide thereof, wherein A, B, D, R, $R_1$-$R_6$, are as described above.

In another aspect the disclosure provides methods for stereoselectively inhibiting sodium channels, comprising contacting cells with a aryloxy propan-2-amine-based compound of Formula I in the form of a free base or a pharmaceutically acceptable salt, prodrug, hydrate, solvate or N-oxide thereof, wherein A, B, D, R, $R_1$-$R_6$, are as described above.

R is independently substituted as the R isomeric form

R is independently substituted S and/or R isomeric forms and/or racemic forms,

In another aspect the disclosure provides compounds of Formula I wherein the pharmaceutically acceptable salt is the salt of 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1, 5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), or undecylenic acid

EXAMPLES

The embodiments of the disclosure may be further illustrated by the following non-limiting examples.

Example 1: Kinetics for APD in Cardiomyocytes

Data (i.e., IC50 values) from experiments with normal human induced pluripotent stem cell (hiPSC) cardiomyocyte or cardiomyocytes derived from hiPSCs from a LQTS3 patient (cells obtained from CDI International) were obtained from dose escalation experiments using a high throughput membrane potential assay using the novel voltage sensitive dye, VF2.1 Cl. Normal or LQTS3 patient-derived cardiomyocytes were cultured for 2 weeks prior to imaging. On the day of the experiment, the cells were washed with Tyrode's solution and each compound was added to the cells from a 2× stock, incubated for 5 minutes and imaged for 6.5 seconds at 100 Hz using a kinetic imaging cytometer (KIC) (Vala Sciences) to obtain fluorescence versus concentration effects. Subsequent image analysis and physiological parameter calculations was conducted using Cyteseer software from Vala Sciences. Dose response curves were generated using Graphpad Prism software. Maturity of sodium, potassium and calcium channels were fully characterized in both normal and LQT3 cardiomyocytes with single cell patch clamp voltage-gated studies. This data was compared to data obtained from channels transfected into cells (see Example 2).

Normal cardiomyocytes dose response. A plot of log of action potential delay (APD)75 vs. log of racemic Mexiletine or Mexiletine analogs concentration in molar dose response curve for a dose escalation of Mexiletine in normal hiPSC derived cardiomyocytes afforded prolongation of 2.85 fold (n=5) (Table 1, below). The plot showed the dose dependent prolongation of the action potential duration in response to Mexiletine.

LQTS3 dose response-log: A plot of log of APD75 vs. log of racemic Mexiletine concentration in molar dose response curve for a dose escalation of Mexiletine in LQTS3 patient-derived cardiomyocytes afforded an IC50 value of 1.83 uM for shortening APD and 1.34-fold shortening (n=5) (Table 2, below). The plot showed a dose dependent shortening of the action potential duration for a dose escalation of Mexiletine. The data showed the utility of using normal human and patient-derived cardiomyocytes to afford molecules with superior on-target vs. off-target effects. Mexiletine analogs were likewise tested. This identified optimal compounds that shortened the APD.

TABLE 1

Pharmacological Parameters in Normal human IPSC-derived Cardiomyocytes.

| No. Code | Structure | Peak Na+ ($I_{NaP}$) IC$_{50}$ (uM) | Late Na+ ($I_{NaL}$) IC$_{50}$ (uM) | $D_{NaP/NaL}$ | hERG ($I_{Kr}$) IC$_{50}$ (uM) | $D_{Kr/NaL}$ | $D_{NaP/Kr}$ | WT-EAD Dose (uM) | WT-Fold Prolongation | WT-Prolongation Dose (uM) | Cessation of Beating (uM) |
|---|---|---|---|---|---|---|---|---|---|---|---|
| 1 | 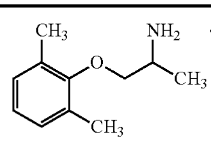 | 183 | 22 | 8.3 | 54 | 2.5 | 3.4 | 200 | 2.653 | 66 | |
| 2a | 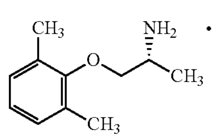 | 128 | 30 | 4.3 | 54 | 1.8 | 2.4 | 200 | 2.661 | 133 | |
| 2b | 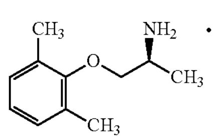 | 129 | 19 | 6.8 | 84 | 4.4 | 1.5 | 200 | 2.289 | 200 | |
| 9 | 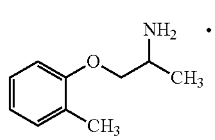 | 162 | 52 | 3.1 | 98 | 1.9 | 1.7 | 200 | 2.363 | 200 | |
| 10 | 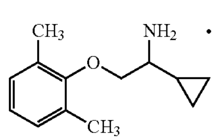 | 130 | 7.3 | 18.0 | 30 | 4.1 | 4.3 | 66 | 2.262 | 22 | |

TABLE 1-continued

| # | Structure | | | | | | | | | |
|---|---|---|---|---|---|---|---|---|---|---|
| 11 | 2,6-dimethylphenoxy-CH₂-CH(CH₃)-NH-CH₃ · HCl | 124 | 36 | 3.4 | 44 | 1.2 | 2.8 | 22 | 2.194 | 22 |
| 12 | 2,6-dimethylphenoxy-CH₂-C(NH₂)(C(CH₃)₃) · HCl | 91 | 11 | 8.3 | 49 | 4.5 | 1.9 | 7.4 | >4 | 22 |
| 13 | 2,6-dimethylphenoxy-CH(NH₂)-phenyl · HCl | 21 | 12 | 1.8 | 8 | 0.7 | 2.6 | | 1.389 | 22 |
| 14 | 2,6-dimethylphenoxy-CH₂-C(=N-OBn)-phenyl | | | | | | | None | None | None |
| 15 | 2,6-dimethylphenoxy-CH₂-CH(NH₂)-(4-methoxyphenyl) · HCl | | | | | | | None | None | 66 |
| 16 | 2,6-dimethylphenoxy-CH₂-CH(NH₂)-(4-CF₃-phenyl) · HCl | | | | | | | None | None | 66 |
| 17 | 2,6-dimethylphenoxy-CH₂-CH(NH₂)-(4-methylphenyl) · HCl | | | | | | | None | None | 66 |
| 18 | pyridin-2-yloxy-CH₂-C(=N-OBn)-phenyl · HCl | | | | | | | None | None | None |
| 19 | (3-methylpyridin-2-yl)oxy-CH₂-C(=N-OBn)-phenyl · HCl | | | | | | | None | None | 133 |
| 20 | pyridin-2-yloxy-CH(NH₂)-phenyl · HCl | | | | | | | None | None | None |
| 21 | (3-methylpyridin-2-yl)oxy-CH₂-CH(OH)-phenyl · HCl | 128.6 | 21.2 | 6.1 | 100 | 4.7 | 1.3 | None | None | None |

TABLE 1-continued

| # | Structure | | | | | | | | | | |
|---|---|---|---|---|---|---|---|---|---|---|---|
| 22 | 2,6-dimethylphenoxy-CH₂-CH(OH)-C(CH₃)₃ · HCl | Not Done | | | | | | | | | |
| 23 | 2-(n-propyl)phenoxy-CH₂-CH(NH₂)-Ph · HCl | | | | | | | None | None | 22 |
| 24 | 2-ethylphenoxy-CH₂-CH(NH₂)-Ph · HCl | | | | | | | None | None | 66 |
| 25 | 2-methylphenoxy-CH₂-CH(NH₂)-Ph · HCl | 34.2 | 0.642 | 53.3 | 22.9 | 35.7 | 1.5 | None | None | 133 |
| 26 | 2-methoxyphenoxy-CH₂-CH(NH₂)-Ph · HCl | | | | | | 7.4 | 2.502 | 7.4 | 22 |
| 27 | 2-trifluoromethylphenoxy-CH₂-CH(NH₂)-Ph · HCl | 41.1 | 1.04 | 39.5 | 37.5 | 36.1 | 1.1 | None | None | 66 |
| 28 | 2,6-dimethylphenoxy-CH₂-CH(NHC(O)CH₃)-Ph | | | | | | | None | None | 66 |
| 29 | 2,6-dimethylphenoxy-CH₂-CH(NHC(O)Ph)-Ph | | | | | | | None | None | None |
| 30 | 2,3-dimethylphenoxy-CH₂-CH(NH(n-butyl))-Ph · HCl | | | | | | | None | None | 133 |

TABLE 1-continued

| | Structure | | | | | | | | | |
|---|---|---|---|---|---|---|---|---|---|---|
| 31 | [2-(2,3-dimethylphenoxy)-1-phenylethyl]propylamine · HCl | | | | | | | None | None | None |
| 32 | 2-(2,3-dimethylphenoxy)-1-phenylethanol · HCl | | | | | | | None | None | 133 |
| 33 | [2-(2,3-dimethylphenoxy)-1-phenylethyl]ethylamine · HCl | | | | | | | None | None | 133 |
| 34 | [2-(2,3-dimethylphenoxy)-1-phenylethyl]methylamine · HCl | | | | | | | None | None | 133 |
| 35 | 2-(2,3-dimethylphenoxy)-1-phenylethylamine · HCl | | | | | | | None | None | 133 |
| 36 | [2-(2,3-dimethylphenoxy)-1-phenylethyl](2-methoxyethyl)amine · HCl | 25.8 | 0.747 | 34.5 | 27.6 | 36.9 | 0.9 | None | None | None |
| 37 | 1-(2,6-dimethylphenoxy)propan-2-ol · HCl | | | | | | | None | None | None |
| 38 | [1-(2,6-dimethylphenoxy)propan-2-yl]propylamine · HCl | | | | | | 66 | 4.584 | 66 | 200 |

TABLE 1-continued

| # | Structure | | | | |
|---|---|---|---|---|---|
| 39 | 2,6-dimethylphenoxy-propyl-N-butyl amine · HCl | 66 | 3.827 | 22 | 133 |
| 40 | 2,6-dimethylphenoxy-propyl-N-(2-methoxyethyl) amine · HCl | 66 | 4.366 | 32 | None |
| 41 | 2,6-dimethylphenoxy-propyl-N-ethyl amine · HCl | 133 | 5.338 | 32 | None |
| 42 | 2,6-dimethylphenoxy-propyl-N-benzyl amine · HCl | | 1.684 | 5.7 | 200 |
| 43 | 2,6-dimethylphenoxy-propyl-N-phenyl amine · HCl | | None | None | None |
| 44 | 2,6-dimethylphenoxy-propyl-N-phenethyl amine · HCl | 22 | 2.698 | 2.5 | 133 |
| 45 | cyclohexyloxy-propan-2-one O-benzyl oxime · HCl | | None | None | None |
| 46 | 1-(2,6-dimethylphenoxymethyl)-1-cyclopropyl methanone O-benzyl oxime · HCl | | None | None | None |

TABLE 1-continued
| # | Structure | | | | | | | | | |
|---|---|---|---|---|---|---|---|---|---|---|
| 47 | 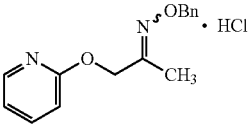 [SMILES: CC(COc1ccccn1)=NOCc1ccccc1 ; "·  HCl"] | | | | | | | Not Determined | | |
| 48 | 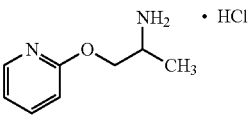 | | | | | | | None | None | None |
| 49 | 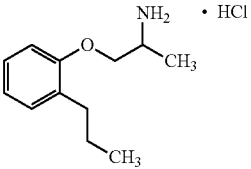 | | | | | | | 1.385 | 7.8 | 200 |
| 50 | 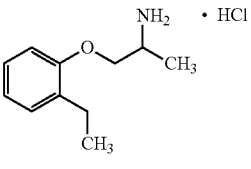 | | | | | | | 1.392 | 23.5 | None |
| 51 | 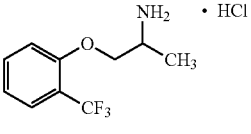 | | | | | | | None | None | None |
| 52 | 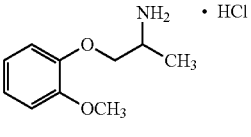 | | | | | | 133 | 2.499 | 97.7 | None |
| 53 | 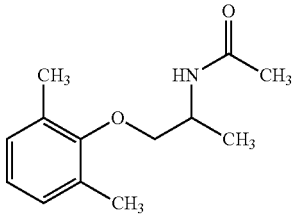 [SMILES: CC(=O)NC(C)COc1c(C)cccc1C] | | | | | | | None | None | None |
| 54 | 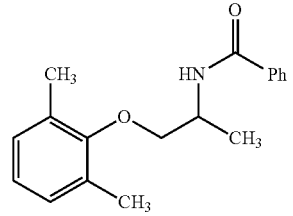 [SMILES: Cc1cccc(C)c1OCC(C)NC(=O)c1ccccc1] | | | | | | | None | None | 66 |
| 55 | 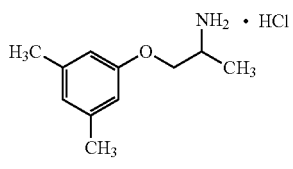 | 154 | 17 | 9.1 | 49 | 2.9 | 3.1 | 1.159 | 22 | None |

TABLE 1-continued
| | | | | | |
|---|---|---|---|---|---|
| 56 | 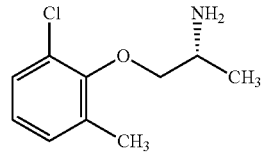 | | 133 | 3.925 | 133 | None |
| 57 | 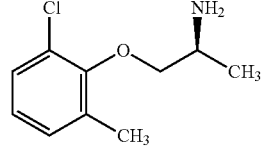 | | 200 | 3.615 | 133 | None |
| 58 | 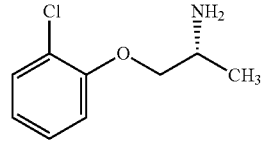 | | 200 | 2.392 | 133 | None |
| 59 | 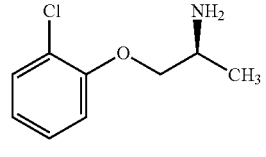 | | 133 | 2.832 | 22 | None |
| 60 | 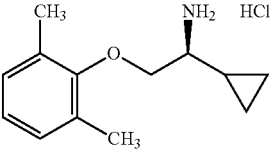 | | 66 | 2.805 | 22 | 200 |
| 61 | 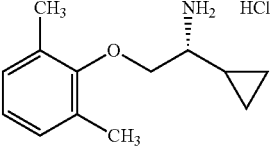 | | 66 | 3.829 | 66 | None |
| 62 | 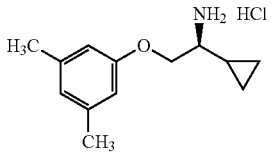 | | 66 | 1.585 | 66 | 200 |
| 63 | 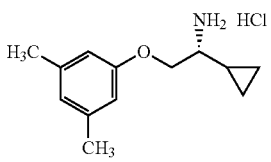 | | 66 | 1.577 | 66 | None |
| 64 | 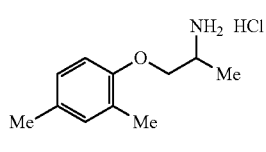 [SMILES: Cl ; Cc1ccc(OCC(C)N)c(C)c1] | | 133 | 2.621 | 66 | None |
| 65 | 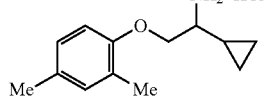 | | 66 | 2.12 | 66 | 200 |

TABLE 1-continued

| # | Structure | | | | | | | | | | |
|---|---|---|---|---|---|---|---|---|---|---|---|
| 66 | 2,4-dimethylphenoxy-CH2-CH(NH2)-Ph · HCl | 22.1 | 2.1 | 10.5 | 5.9 | 2.8 | 3.7 | | None | None | 66 |
| 67 | 3,5-dimethylphenoxy-CH2-CH(NH-CH2CH2-OCH3)-CH3 · HCl | 135.6 | 10.6 | 12.8 | 63 | 5.9 | 2.2 | 66 | 2.408 | 66 | None |
| 68 | 3,5-dimethylphenoxy-CH2-CH(NH-CH2CH2-OCH3)-cyclopropyl · HCl | | | | | | | 66 | 1.686 | 66 | 200 |
| 69 | 3,5-dimethylphenoxy-CH2-CH(NH-CH2CH2-OCH3)-Ph · HCl | 38.3 | 0.845 | 45.3 | 5.1 | 6.0 | 7.5 | | None | None | 200 |
| 70 | 3,5-dimethylphenoxy-CH2-CH(NH2)-Ph · HCl | 18.9 | 0.182 | 103 | 6.2 | 34.0 | 3.0 | | None | None | 66 |
| 71 | phenoxy-CH2-CH(NH2)-Me (R) · HCl | | | | | | | 200 | 1.997 | 200 | None |
| 72 | phenoxy-CH2-CH(NH2)-Me (S) · HCl | | | | | | | 133 | 2.93 | 200 | None |
| 73 | 2,6-dimethylphenoxy-CH2-CH(NH2)-cyclohexyl · HCl | | | | | | | | None | None | 66 |
| 74 | 9-methyl-3-cyclopropyl-2,3,4,5-tetrahydro-1,4-benzoxazepine · HCl | | | | | | | 133 | 2.633 | 133 | None |

TABLE 1-continued
| # | Structure | | | | | | | | | |
|---|---|---|---|---|---|---|---|---|---|---|
| 75 | 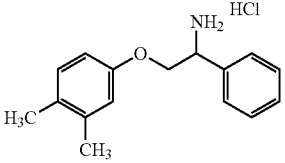 [SMILES: Cl ; Cc1ccc(OCC(N)c2ccccc2)cc1C] | | | | | | | None | None | 66 |
| 76 | 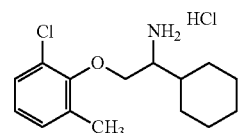 | | | | | | | None | None | 66 |
| 77 | 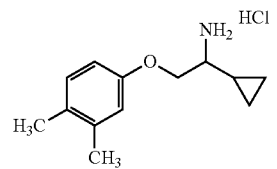 | | | | | | | None | None | 66 |
| 78 | 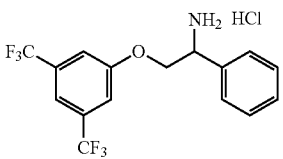 | 20 | 1.03 | 19.4 | | | | None | None | 133 |
| 79 | 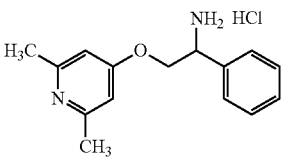 [SMILES: Cl ; NC(COc1cc(C(F)(F)F)cc(C(F)(F)F)c1)c1ccccc1] | | | | | 200 | 5.06 | 133 | None | |
| 80 | 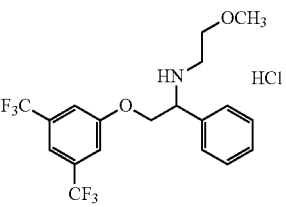 [SMILES: COCCNC(COc1cc(C(F)(F)F)cc(C(F)(F)F)c1)c1ccccc1 ; Cl] | 45.1 | 1.02 | 44.2 | 16.8 | 16.5 | 2.7 | None | None | None |
| 81 | 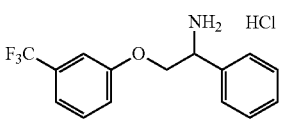 | | | | | | | None | None | 66 |
| 82 | 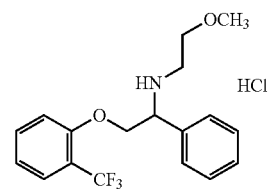 | 44.3 | 1.14 | 38.9 | | | | None | None | 66 |
| 83 | 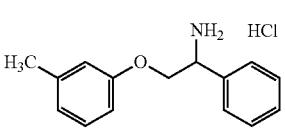 [SMILES: NC(COc1cccc(C(F)(F)F)c1)c1ccccc1 ; Cl] | | | | | | | None | None | 133 |

TABLE 1-continued

| # | Structure | Salt | | | | | | | | | |
|---|---|---|---|---|---|---|---|---|---|---|---|
| 84 | 3,5-bis(CF₃)-C₆H₃-O-CH₂-CH(NH₂)-CH₃ | HCl | | | | | | | None | None | 133 |
| 85 | 3-CF₃-C₆H₄-O-CH₂-CH(NH₂)-CH₃ | HCl | | | | | | | None | None | 200 |
| 86 | 3-CH₃-C₆H₄-O-CH₂-CH(NH₂)-CH₃ | HCl | | | | | | 66 | 1.68 | 66 | None |
| 87 | cyclohexyl-O-CH₂-CH(NH₂)-CH₃ | HCl | | | | | | | None | None | None |
| 88 | (4-methylpyridin-3-yl)-O-CH₂-CH(NH₂)-Ph | HCl | | | | | | | 1.52 | 66 | None |
| 89 | 3,5-(CH₃)₂-C₆H₃-O-CH₂-CH(NH₂)-cyclohexyl | HCl | 24.3 | 1.6 | 15.2 | 4.9 | 3.1 | 5.0 | | | |
| 90 | 2-CH₃-C₆H₄-O-CH₂-CH(NH-CH₂CH₂OCH₃)-Ph | HCl | 33.4 | 2.83 | 11.8 | | | | None | None | 133 |
| 91 | 3,5-(CH₃)₂-C₆H₃-O-CH₂-CH(NH₂)-cyclopropyl | HCl | 76.8 | 10 | 7.7 | 45.8 | 4.6 | 1.7 | | | |
| 92 | 3,5-(CH₃)₂-C₆H₃-O-CH₂-CH(NH-CH₂CH₂OH)-Ph | | | | | | | | None | None | 66 |
| 93 | 3,5-bis(CF₃)-C₆H₃-O-CH₂-CH(NH-CH₂CH₂OH)-Ph | | | | | | | | None | None | 66 |

TABLE 1-continued
| No. | Structure | | | | | | LQT-IC50 | LQT-Fold Shortening | LQT-Shortening Dose (uM) | |
|---|---|---|---|---|---|---|---|---|---|---|
| 94 | 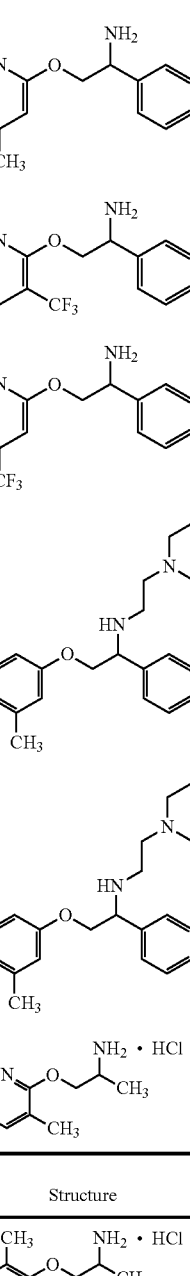 | | | | | | 133 | 2.48 | 133 | None |
| 95 | 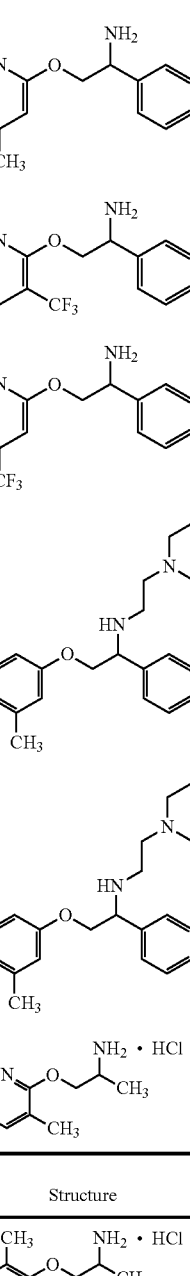 | | | | | | 133 | 2.68 | 200 | None |
| 96 | 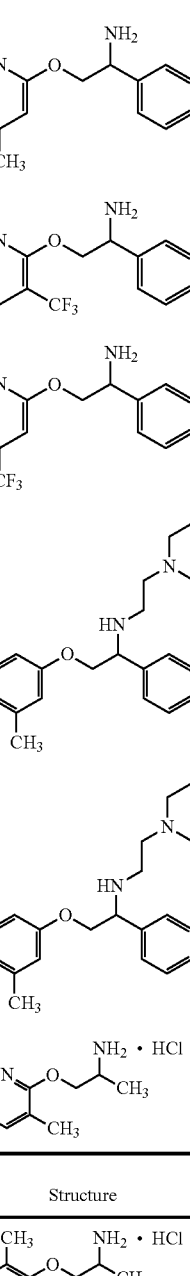 | | | | | | | 1.163 | 200 | None |
| 97 | 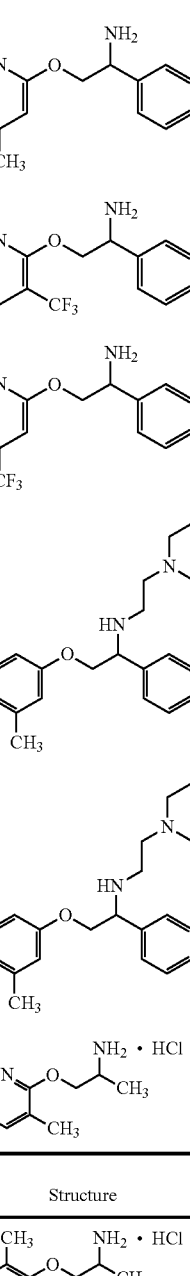 | | | | | | 133 | None | None | None |
| 98 | 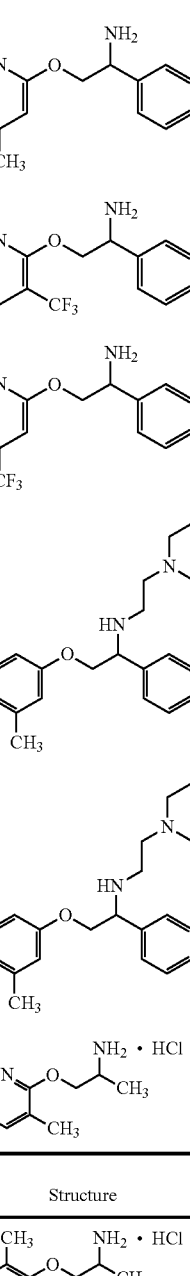 | | | | | | | 1.54 | 7.4 | |
| 99 | 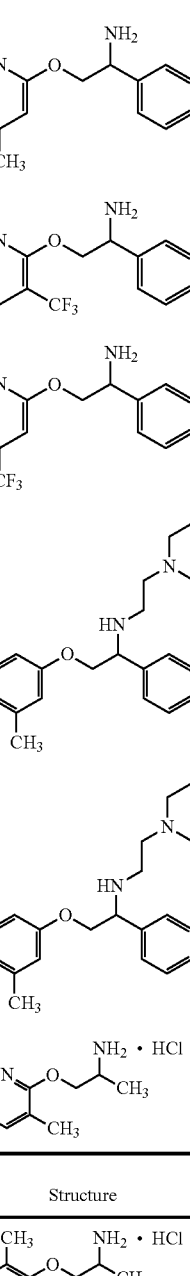 | | | | | | | | | |
| 100 | 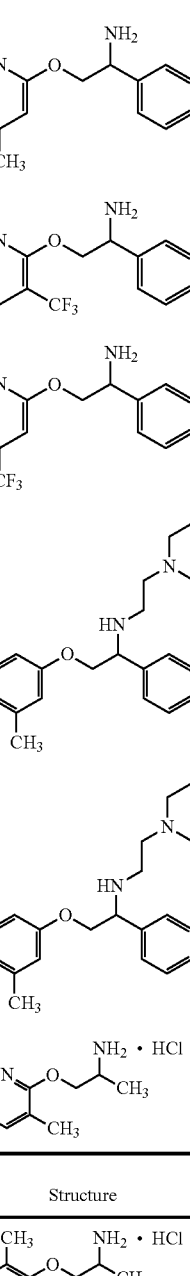 | 252 | n/a | n/a | n/a | n/a | | None | None | None |
| No. Code | Structure | LQT-IC50 (uM)-Shortening | LQT-Cessation Dose (uM) | LQT-EAD Dose (uM) | LQT-Fold Shortening | LQT-Shortening Dose (uM) |
|---|---|---|---|---|---|---|
| 1 | | 1.83 | None | | 1.335 | 22 |
| 2a | | 0.96 | None | | 1.346 | 7.4 |
| 2b | | 0.8 | None | | 1.25 | 22 |

TABLE 1-continued

| # | Structure | | | | |
|---|---|---|---|---|---|
| 9 | 2-methylphenoxy-propan-2-amine·HCl | 0.76 | None | 1.28 | 22 |
| 10 | 1-(2,6-dimethylphenoxy)-1-cyclopropyl-methanamine·HCl | 0.8 | 200 | 1.162 | 22 |
| 11 | N-methyl-1-(2,6-dimethylphenoxy)propan-2-amine·HCl | 1.48 | 133 | 1.112 | 22 |
| 12 | 1-(2,6-dimethylphenoxy)-3,3-dimethylbutan-2-amine·HCl | 0.648 | 22 | 1.182 | 2.5 |
| 13 | 2-(2,6-dimethylphenoxy)-1-phenylethan-1-amine·HCl | 0.72 | 66 | 1.174 | 2.5 |
| 14 | O-benzyl oxime of 2-(2,6-dimethylphenoxy)-1-phenylethan-1-one | None | None | None | None |
| 15 | 2-(2,6-dimethylphenoxy)-1-(4-methoxyphenyl)ethan-1-amine·HCl | | 66 | 1.42 | 7.4 |
| 16 | 2-(2,6-dimethylphenoxy)-1-(4-trifluoromethylphenyl)ethan-1-amine·HCl | 1.38 | 66 | 1.480 | 22 |
| 17 | 2-(2,6-dimethylphenoxy)-1-(4-methylphenyl)ethan-1-amine·HCl | | 66 | 1.58 | 22 |
| 18 | O-benzyl oxime of 2-(pyridin-2-yloxy)-1-phenylethan-1-one·HCl | | None | None | None |
| 19 | O-benzyl oxime of 2-(3-methylpyridin-2-yloxy)-1-phenylethan-1-one·HCl | 1.38 | 133 | 1.406 | 66 |

TABLE 1-continued

| # | Structure | | | |
|---|---|---|---|---|
| 20 | 2-pyridyl-O-CH2-CH(NH2·HCl)-Ph | None | None | None |
| 21 | 3-methyl-2-pyridyl-O-CH2-CH(OH·HCl)-Ph | None | 1.23 | 7.4 |
| 22 | 2,6-dimethylphenyl-O-CH2-CH(OH)-C(CH3)3 ·HCl | None | 1.29 | 133 |
| 23 | 2-propylphenyl-O-CH2-CH(NH2·HCl)-Ph | 0.78 | 22 | 1.32 | 2.5 |
| 24 | 2-ethylphenyl-O-CH2-CH(NH2·HCl)-Ph | 0.38 | 22 | 1.979 | 7.4 |
| 25 | 2-methylphenyl-O-CH2-CH(NH2·HCl)-Ph | 0.73 | 66 | 1.606 | 22 |
| 26 | 2-methoxyphenyl-O-CH2-CH(NH2·HCl)-Ph | 0.13 | 133 | 1.482 | 0.8 |
| 27 | 2-trifluoromethylphenyl-O-CH2-CH(NH2·HCl)-Ph | >0.8 | 66 | 1.783 | 22 |
| 28 | 2,6-dimethylphenyl-O-CH2-CH(NHAc)-Ph | >0.8 | 66 | 1.620 | 22 |
| 29 | 2,6-dimethylphenyl-O-CH2-CH(NHC(O)Ph)-Ph | >0.8 | None | 1.64 | 66 |

TABLE 1-continued

| 30 | *structure: N-butyl, 2,3-dimethylphenoxy phenethylamine · HCl* | 20.16 | 200 | 1.423 | 133 |
| 31 | *structure: N-propyl, 2,3-dimethylphenoxy phenethylamine · HCl* | | 133 | None | None |
| 32 | *structure: 2,3-dimethylphenoxy-1-phenylethanol · HCl* | 7.53 | 66 | 1.355 | 22 |
| 33 | *structure: N-ethyl, 2,3-dimethylphenoxy phenethylamine · HCl* | | 22 | None | None |
| 34 | *structure: N-methyl, 2,3-dimethylphenoxy phenethylamine · HCl* | | 66 | 1.29 | 22 |
| 35 | *structure: 2,3-dimethylphenoxy phenethylamine · HCl* | | 66 | 1.406 | 22 |
| 36 | *structure: N-(2-methoxyethyl), 2,3-dimethylphenoxy phenethylamine · HCl* | 5.73 | 200 | 1.508 | 133 |
| 37 | *structure: 1-(2,6-dimethylphenoxy)-2-propanol · HCl* | | None | None | None |

TABLE 1-continued
| | | | | | |
|---|---|---|---|---|---|
| 38 | 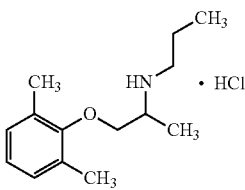 [SMILES: CCCNC(C)COc1c(C)cccc1C ; "·  HCl"] | | 200 | 1.19 | 2.5 |
| 39 | 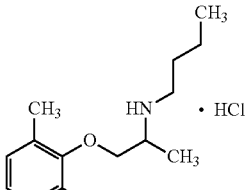 | 0.73 | 66 | 1.180 | 2.5 |
| 40 | 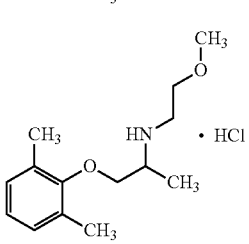 | 2.31 | None | 1.267 | 7.4 |
| 41 | 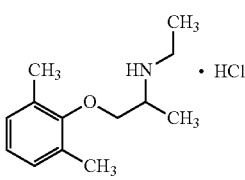 | | None | None | None |
| 42 | 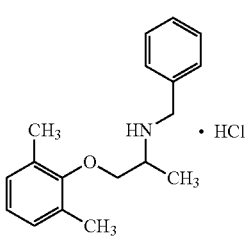 [SMILES: Cc1cccc(C)c1OCC(C)NCc1ccccc1 ; "·  HCl"] | | 133 | 1.26 | 22 |
| 43 | 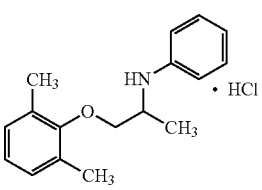 | | None | None | None |
| 44 | 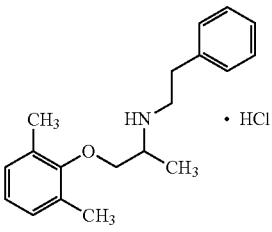 [SMILES: Cc1cccc(C)c1OCC(C)NCCc1ccccc1 ; "·  HCl"] | | 7.4 | 1.7 | 2.5 |
| 45 | 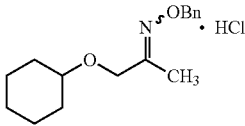 [SMILES: CC(COC1CCCCC1)=NOCc1ccccc1 ; "·  HCl"] | | None | 1.37 | 133 |

TABLE 1-continued

| # | Structure | Col A | Col B | Col C | Col D |
|---|---|---|---|---|---|
| 46 | 2,6-dimethylphenyl-O-CH2-C(=N-OBn)-cyclopropyl · HCl | None | | 1.67 | 133 |
| 47 | pyridin-2-yl-O-CH2-C(=N-OBn)-CH3 · HCl | Not done | | — | — |
| 48 | pyridin-2-yl-O-CH2-CH(NH2)-CH3 · HCl | None | | None | None |
| 49 | 2-propylphenyl-O-CH2-CH(NH2)-CH3 · HCl | 0.85 | 133 | 1.192 | 7.4 |
| 50 | 2-ethylphenyl-O-CH2-CH(NH2)-CH3 · HCl | 6.01 | None | 1.12 | 22 |
| 51 | 2-trifluoromethylphenyl-O-CH2-CH(NH2)-CH3 · HCl | None | | 1.37 | 133 |
| 52 | 2-methoxyphenyl-O-CH2-CH(NH2)-CH3 · HCl | None | | None | None |
| 53 | 2,6-dimethylphenyl-O-CH2-CH(NHC(O)CH3)-CH3 | None | | None | None |
| 54 | 2,6-dimethylphenyl-O-CH2-CH(NHC(O)Ph)-CH3 | 57.82 | 133 | 1.45 | 66 |

TABLE 1-continued

| # | Structure | | | | |
|---|---|---|---|---|---|
| 55 | (S)-1-(3,5-dimethylphenoxy)propan-2-amine · HCl | 4.45 | 200 | 1.232 | 66 |
| 56 | (S)-1-(2-chloro-6-methylphenoxy)propan-2-amine | 0.04 | None | 1.189 | 7.4 |
| 57 | (R)-1-(2-chloro-6-methylphenoxy)propan-2-amine | 0.19 | None | 1.14 | 7.4 |
| 58 | (S)-1-(2-chlorophenoxy)propan-2-amine | | None | None | None |
| 59 | (R)-1-(2-chlorophenoxy)propan-2-amine | | None | None | None |
| 60 | (S)-2-(2,6-dimethylphenoxy)-1-cyclopropylethan-1-amine · HCl | 0.11 | 200 | 1.22 | 0.8 |
| 61 | (R)-2-(2,6-dimethylphenoxy)-1-cyclopropylethan-1-amine · HCl | | 200 | None | None |
| 62 | (S)-2-(3,5-dimethylphenoxy)-1-cyclopropylethan-1-amine · HCl | 1.03 | 200 | 1.19 | 22 |
| 63 | (R)-2-(3,5-dimethylphenoxy)-1-cyclopropylethan-1-amine · HCl | 7.5 | 200 | 1.11 | 22 |
| 64 | 1-(2,4-dimethylphenoxy)propan-2-amine · HCl | | None | None | None |

TABLE 1-continued
| | | | | | |
|---|---|---|---|---|---|
| 65 | 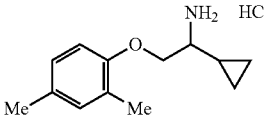 | 1.36 | 200 | 1.119 | 66 |
| 66 | 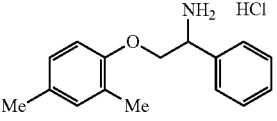 [SMILES: Cl ; Cc1ccc(OCC(N)c2ccccc2)c(C)c1] | 0.486 | 66 | 1.192 | 7.4 |
| 67 | 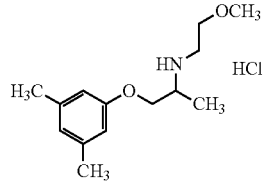 | None | None | None | None |
| 68 | 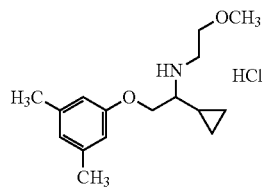 [SMILES: COCCNC(COc1cc(C)cc(C)c1)C1CC1 ; Cl] | 0.022 | 200 | 1.11 | 66 |
| 69 | 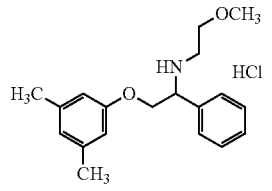 [SMILES: COCCNC(COc1cc(C)cc(C)c1)c1ccccc1 ; Cl] | None | 200 | None | None |
| 70 | 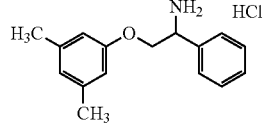 [SMILES: Cc1cc(C)cc(OCC(N)c2ccccc2)c1 ; Cl] | 0.0013 | 66 | 1.279 | 7.4 |
| 71 | 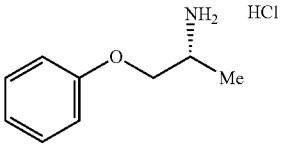 [SMILES: Cl ; C[C@@H](N)COc1ccccc1] | 193.7 (prolongation) | None | 1.214 (prolongation) | 200 |
| 72 | 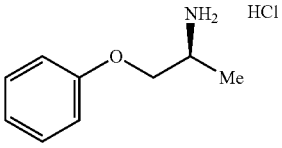 [SMILES: Cl ; C[C@H](N)COc1ccccc1] | 128.9 (prolongation) | None | 1.133 (prolongation) | 200 |
| 73 | 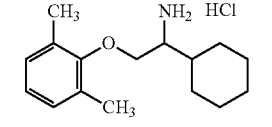 [SMILES: Cl ; Cc1cccc(C)c1OCC(N)C1CCCCC1] | 0.082 | 66 | 1.136 | 0.8 |
| 74 | 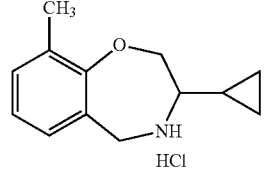 | | None | None | None |

TABLE 1-continued

| | | | | | |
|---|---|---|---|---|---|
| 75 | [structure: 2-(3,4-dimethylphenoxy)-1-phenylethylamine·HCl] | | 66 | 1.370 | 22 |
| 76 | [structure: 2-(2-chloro-6-methylphenoxy)-1-cyclohexylethylamine·HCl] | | 66 | 1.244 | 22 |
| 77 | [structure: 2-(3,4-dimethylphenoxy)-1-cyclopropylethylamine·HCl] | | 200 | 1.18 | 22 |
| 78 | [structure: 2-(3,5-bis(trifluoromethyl)phenoxy)-1-phenylethylamine·HCl] | 23.08 | 66 | 1.208 | 22 |
| 79 | [structure: 2-(2,6-dimethylpyridin-4-yloxy)-1-phenylethylamine·HCl] | | None | 1.145 | 133 |
| 80 | [structure: N-(2-methoxyethyl)-2-(3,5-bis(trifluoromethyl)phenoxy)-1-phenylethylamine·HCl] | 6.59 | 133 | 1.636 | 66 |
| 81 | [structure: 2-(3-(trifluoromethyl)phenoxy)-1-phenylethylamine·HCl] | 4.07 | 66 | 1.539 | 22 |
| 82 | [structure: N-(2-methoxyethyl)-2-(2-(trifluoromethyl)phenoxy)-1-phenylethylamine·HCl] | 20.56 | 66 | 1.442 | 22 |
| 83 | [structure: 2-(3-methylphenoxy)-1-phenylethylamine·HCl] | 0.0023 | 66 | 1.410 | 22 |

TABLE 1-continued

| # | Structure | | | | |
|---|---|---|---|---|---|
| 84 | 3,5-bis(trifluoromethyl)phenoxy isopropylamine · HCl | 0.87 | 66 | 1.200 | 7.4 |
| 85 | 3-(trifluoromethyl)phenoxy isopropylamine · HCl | 31.34 | 200 | 1.661 | 133 |
| 86 | 3-methylphenoxy isopropylamine · HCl | Shortens | None | 1.418 | 200 |
| 87 | cyclohexyloxy isopropylamine · HCl | 34.78 | None | 1.611 | 133 |
| 88 | (4-methylpyridin-3-yloxy)-1-phenylethylamine · HCl | 12.82 | None | 1.287 | 66 |
| 89 | 1-(3,5-dimethylphenoxy)-2-cyclohexylethylamine · HCl | | | | |
| 90 | 2-(2-methylphenoxy)-1-phenyl-N-(2-methoxyethyl)ethylamine · HCl | | 133 | 1.1 | 22 |
| 91 | 1-(3,5-dimethylphenoxy)-2-cyclopropylethylamine · HCl | | | | |
| 92 | 2-(3,5-dimethylphenoxy)-1-phenyl-N-(2-hydroxyethyl)ethylamine | | 66 | 1.41 | 22 |
| 93 | 2-(3,5-bis(trifluoromethyl)phenoxy)-1-phenyl-N-(2-hydroxyethyl)ethylamine | | 22 | 1.5 | 7.4 |

TABLE 1-continued

| | | | | |
|---|---|---|---|---|
| 94 | 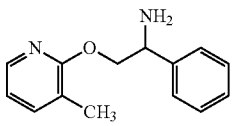 | None | None | None |
| 95 | 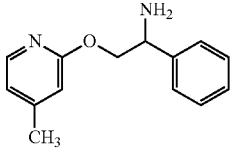 | 22 | 1.22 | 22 |
| 96 | 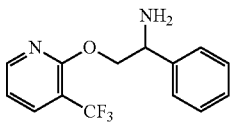 [SMILES: Cc1cccnc1OCC(N)c1ccccc1] | None | 1.3 | 133 |
| 97 | 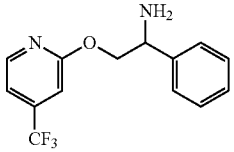 [SMILES: NC(COc1cc(C(F)(F)F)ccn1)c1ccccc1] | None | 1.1 | 22 |
| 98 | 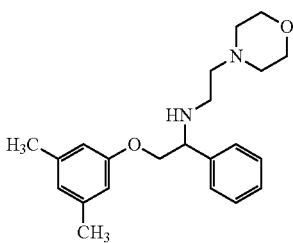 [SMILES: Cc1cc(C)cc(OCC(NCCN2CCOCC2)c2ccccc2)c1] | 66 | 1.3 | 22 |
| 99 | 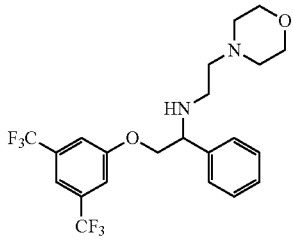 [SMILES: FC(F)(F)c1cc(OCC(NCCN2CCOCC2)c2ccccc2)cc(C(F)(F)F)c1] | 22 | 1.49 | 7.4 |
| 100 | 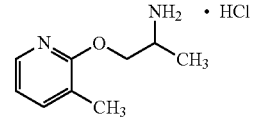 | 22 | 1.13 | 7.4 |

Example 2. Electrophysiology

INa and IKr assays (n=6) were run by patch clamp electrophysiology and confirmed the in vitro potency observed with the Kinetic Image Cytometer (KIC) assays. This provided data to investigate the physiology and action of target compounds on individual ion channels. The assay used standardized protocols for culturing and conducting conventional whole cell recording that have been previously developed for both current and voltage-clamp to characterize action potentials using transfected cells. Briefly, the Nav1.5 sodium channel was transfected into HEK293 cells. The cells were validated using standard assays previously developed and further validated using dose response studies that afforded IC50 values. hERG was expressed in CHO cells and used in automated patch clamp assays. Briefly, cells were plated on 0.1% gelatin-coated 35-mm plastic Petri dishes. Conventional whole cell recording conditions were used in both current and voltage-clamp to characterize action potentials in these cells to investigate the physiology and pharmacology of individual ion channels and the effect of Mexiletine or Mexiletine analogs on function. Data was reported as $IC_{50}$ values±STD (Table 1). For example, racemic Mexiletine had NaI channel Peak (INaP) $IC_{50}$=183 µM, NaI channel Late (INaL) $IC_{50}$=22 µM (ratio=8.3) and hERG potassium channel (IKr) $IC_{50}$=54 VM. Compound 70 had a Na Peak $IC_{50}$=18.9 VM, Na Late $IC_{50}$=0.18 µM (ratio=104) and hERG $IC_{50}$=6 PIM. Analog 70 was thus much more selective for the on-target Na Late channel than Mexiletine.

TABLE 1

Electrophysiology Results for Mexiletine and Analogs using Transfected Cells.

| Compound | Structure | Peak Na$^+$ (I$_{NaP}$) IC$_{50}$ (μM) | Late Na$^+$ (I$_{NaL}$) IC$_{50}$ (μM) | D$_{NaP}$/$_{NaL}$ | hERG (I$_{Kr}$) IC$_{50}$ (μM) | D$_{Kr}$/$_{NaL}$ | D$_{NaP}$/$_{Kr}$ |
|---|---|---|---|---|---|---|---|
| Rac Mexiletine, 1 | | 182.8 | 22.5 | 8.3 | 54 | 2.5 | 73 |
| 36 | 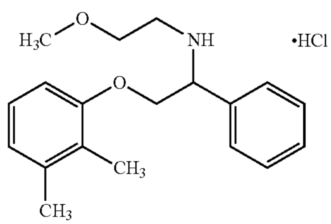 [SMILES: COCCNC(COc1cccc(C)c1C)c1ccccc1 ; Cl] | 25.8 | 0.747 | 34.5 | 27.6 | 36.9 | 0.93 |
| 70 | 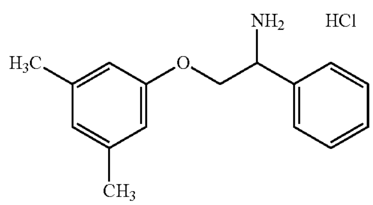 [SMILES: Cc1cc(C)cc(OCC(N)c2ccccc2)c1 ; Cl] | 20.1 | 0.2 | 100.5 | 6.2 | 34.0 | 3.0 |
| 91 | 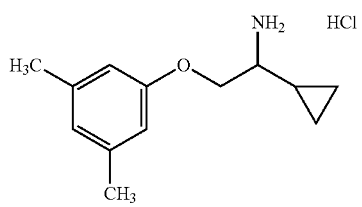 | 76.8 | 10.0 | 7.68 | 45.8 | 4.6 | 1.7 |
| 21 | 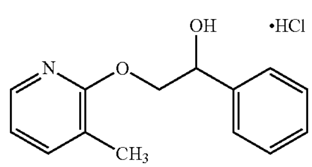 [SMILES: Cc1cccnc1OCC(O)c1ccccc1 ; Cl] | 128.6 | 21.2 | 6.1 | >100 | >4.7 | 1.3 |
| 69 | 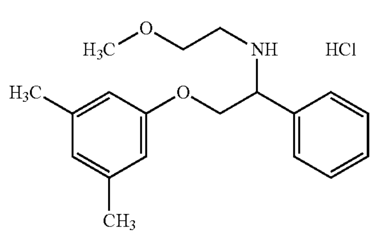 | 38.0 | 0.753 | 50.5 | 5.1 | 6.8 | 7.5 |
| 67 | 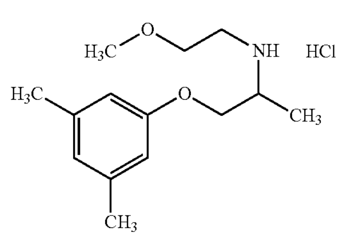 [SMILES: COCCNC(C)COc1cc(C)cc(C)c1 ; Cl] | 135.6 | 10.6 | 12.8 | 63.0 | 5.9 | 2.2 |

TABLE 1-continued

Electrophysiology Results for Mexiletine and Analogs using Transfected Cells.

| Compound | Structure | Peak Na$^+$ (I$_{NaP}$) IC$_{50}$ (μM) | Late Na$^+$ (I$_{NaL}$) IC$_{50}$ (μM) | D$_{NaP}$/$_{NaL}$ | hERG (I$_{Kr}$) IC$_{50}$ (μM) | D$_{Kr}$/$_{NaL}$ | D$_{NaP}$/$_{Kr}$ |
|---|---|---|---|---|---|---|---|
| 25 | 2-methylphenoxy-phenylethylamine·HCl | 34.2 | 0.642 | 53.2 | 22.9 | 35.6 | 1.5 |
| 82 | 2-trifluoromethylphenoxy-phenylethylamine·HCl | 41.1 | 1.04 | 39.5 | 37.5 | 36.1 | 1.1 |
| 89 | 3,5-dimethylphenoxy-cyclohexylethylamine·HCl | 24.3 | 1.6 | 15.3 | 4.9 | 3.1 | 5.0 |
| 66 | 2,4-dimethylphenoxy-phenylethylamine·HCl | 22.1 | 2.1 | 10.7 | 5.9 | 2.8 | 3.7 |
| 78 | 3,5-bis(trifluoromethyl)phenoxy-phenylethylamine·HCl | 20.0 | 1.03 | 19.4 | 7.2 | 7.0 | 2.77 |
| 80 | 3,5-bis(trifluoromethyl)phenoxy-phenyl-N-(2-methoxyethyl)ethylamine·HCl | 45.1 | 1.02 | 44.2 | 16.8 | 16.5 | 2.7 |
| 88 | 3-methylpyridyloxy-phenylethylamine·HCl | 90.9 | 1.04 | 87.4 | 11.2 | 10.7 | 7.7 |

TABLE 1-continued

Electrophysiology Results for Mexiletine and Analogs using Transfected Cells.

| Compound | Structure | Peak Na+ ($I_{NaP}$) $IC_{50}$ (μM) | Late Na+ ($I_{NaL}$) $IC_{50}$ (μM) | $D_{NaP}/_{NaL}$ | hERG ($I_{Kr}$) $IC_{50}$ (μM) | $D_{Kr}/_{NaL}$ | $D_{NaP}/_{Kr}$ |
|---|---|---|---|---|---|---|---|
| 105 | (structure: 2-CF3-phenoxy, HN-CH2CH2-OCH3, phenyl, HCl) | 44.3 | 1.14 | 38.9 | 20.9 | 18.3 | 2.11 |
| 90 | (structure: 2-CH3-phenoxy, HN-CH2CH2-OCH3, phenyl, HCl) | 33.4 | 2.83 | 11.8 | 25.3 | 1.32 | 1.32 |
| 35 | (structure: 2,3-dimethyl-phenoxy, NH2, phenyl, ·HCl) | 10.9 | 1.03 | 10.6 | 9.2 | 8.9 | 1.2 |

Patch clamp recordings from hIPSC LQT3 patient-derived cardiomyocytes for Na+ channel currents were recorded in response to computed voltage waveforms that simulated adult ventricular action potentials. These channels were recorded in human cardiomyocytes and showed all the relevant ion channels in a native context. This confirmed the KIC data that revealed a compound's on- and off-target effects. Patch-clamp recording of hIPSC-LQT3 patient-derived cardiomyocytes showed the presence of functional K+, Na+ and Ca2+ currents, typical for functional cardiomyocytes. Patch clamp studies with LQT3 patient-derived cardiomyocytes showed a significantly prolonged Na+ current, reflecting the substantial proportion of late Na+ current component. The NaI channel Peak (INaP) IC50>100 μM, NaI channel Late (INaL) IC50=1.8 μM (ratio >56) for 82. The NaI channel Peak (INaP) IC50>100 μM, NaI channel Late (INaL) IC50=1.74 μM (ratio>57) for 25. The results are in good agreement with previous electrophysiology data (Table 1, above) and that obtained from optical screening assays (KIC assays). The results showed more potent and selective sodium channel inhibitors with more favorable (lower) potassium channel inhibition were obtained.

Example 3: Synthesis of Compounds of Formula I

The phenoxy propan-2-amine-based compounds of general structure I:

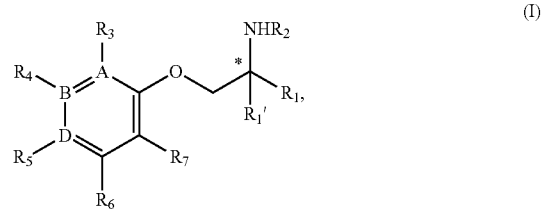

(I)

was synthesized according to the following Schemes:

Scheme 1: General Synthetic Procedure for synthesis of aryloxy propan-2-amines of compound I.

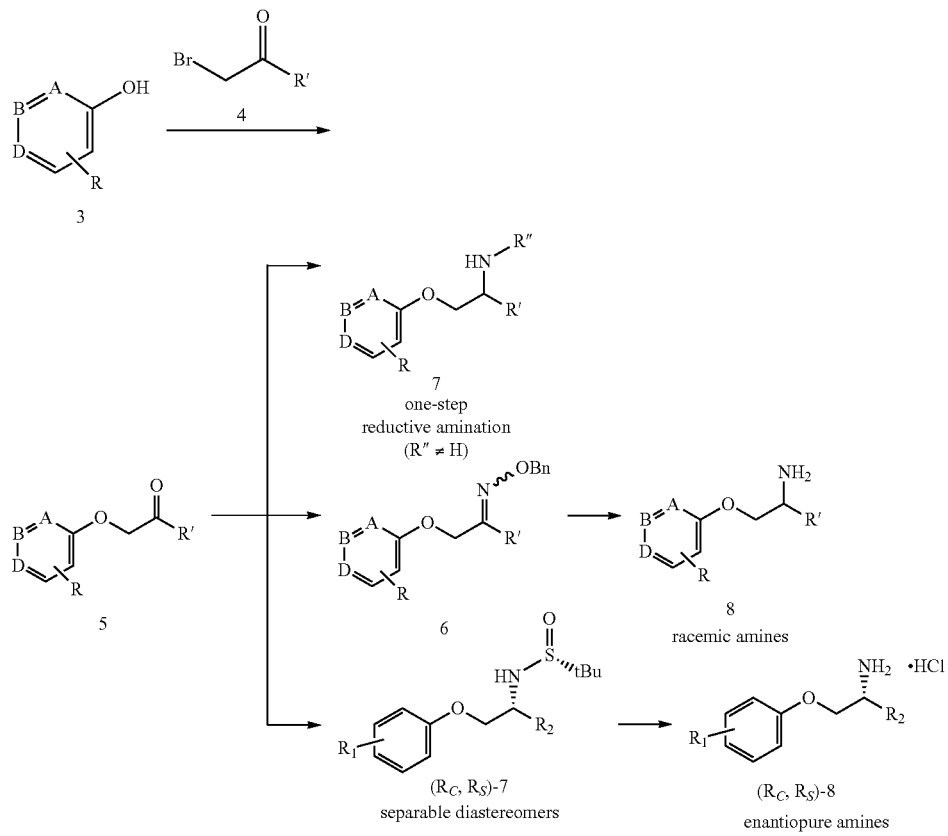

A, B, or D are C or N atoms

Potassium carbonate (1.5 eq.) was added to a stirred solution of 2,6-dimethylphenol (1.5 eq.) and bromoacetone (0.5 M, 1.0 eq.) in DMF at 21° C. After 12-24 hours, the mixture was poured into water and extracted with diethyl ether (2×), washed with 2N NaOH$_{(aq)}$ (5×), dried (Na$_2$SO$_4$), filtered, and concentrated. The product was purified by silica gel column chromatography (ethyl acetate/hexanes) to provide alpha-aryloxy ketones.

The synthesis of Mexiletine enantiomers was done as follows. A two-step condensation-reduction protocol was used to convert ketones 5 to N-tert-butanesulfinyl amines 7 without isolation of hydrolytically unstable N-tert-butanesulfinyl imines (i.e., 6). Reduction of 6 showed substrate and reagent-based stereoselectivity wherein sodium borohydride and L-selectride favored opposite diastereomers of 7. Product diastereomer ratios of 7 were determined by RP HPLC analysis of the crude product. Following separation of diastereomers 7 by silica gel chromatography, (R$_C$, R$_S$-7) and (S$_C$, R$_S$-7) were separately treated with 4N HCl in 1,4-dioxane. The products (R)-8 and (S)-8 were obtained as hydrochloride salts and the enantiopurity of the products was determined by chiral phase HPLC. Isolated products were obtained in greater than 95% purity as judged by $^1$H NMR or HPLC-UV/MS analysis. For 1-3 that have not been experimentally characterized in the scientific literature, the (R$_C$) and (S$_C$) designations of 7 were assumed based on their optical rotation data and HPLC chromatographic profile compared to close structural analogs.

General Procedure "A" for Synthesis of N-tert-butanesulfinyl Amines 5-10. Ti(OEt)4 (2.2 eq.) was added to a mixture of ketone (1.0 eq.) and (R)-tert-butanesulfinamide (1.2 eq.) in a glass microwave vial, sealed and the neat mixture was subjected to microwave heating at 70° C. for 1 h, cooled, diluted with EtOAc and added to a saturated solution of NaCl(aq) (0.1 mL/mmol Ti(OEt)4) with stirring. The resulting suspension was vacuum-filtered through Celite, concentrated and dissolved in THF (1.7 mL/mmol ketone) and CuSO4 (1.0 eq.) and NaBH4 (1.2 eq.) were added at 21° C. After 5 h, acetic acid was added, stirred for 5 min, and concentrated and re-suspended in CH2Cl2, vacuum-filtered through Celite and concentrated. Products were analyzed by HPLC to determine diastereomeric ratio, then purified by silica gel flash column chromatography as described below. Product purity was determined by HPLC to be >95% in all examples. See Example 4, below, for examples.

General Procedure "B" for Synthesis of N-tert-butanesulfinyl Amines. The method is the same as A, above, but the concentrate was dissolved in THF (1.7 mL/mmol ketone) and cooled to −45° C. L-Selectride (1.2 eq., 1 M solution in THF) was added at −45° C. After 5 h, acetic acid was added. The mixture was removed from the cold, stirred for 5 min, concentrated by rotary evaporation, re-suspended in CH2Cl2, vacuum-filtered through Celite and the filtrate was concentrated. Products were analyzed by HPLC to determine diastereomeric ratio and purified by silica gel flash column chromatography as described for individual products below. Product purity was determined by HPLC to be >95% in all examples. See Example 5 for purity analysis.

General Procedure for Removal of the N-tert-butanesulfinyl Group. N-tert-butanesulfinyl amines (i.e., 5-10) were dissolved in 4 N HCl in 1,4-dioxane. After 5-12 hours, the mixture was diluted with diethyl ether (2 eq.) to effect precipitation of the product amine hydrochloride salts. The suspension was vacuum-filtered and dried under high-vacuum to provide amine hydrochlorides as white solids. See Example 4 for examples.

Scheme 3. Synthetic approach to primary amines.

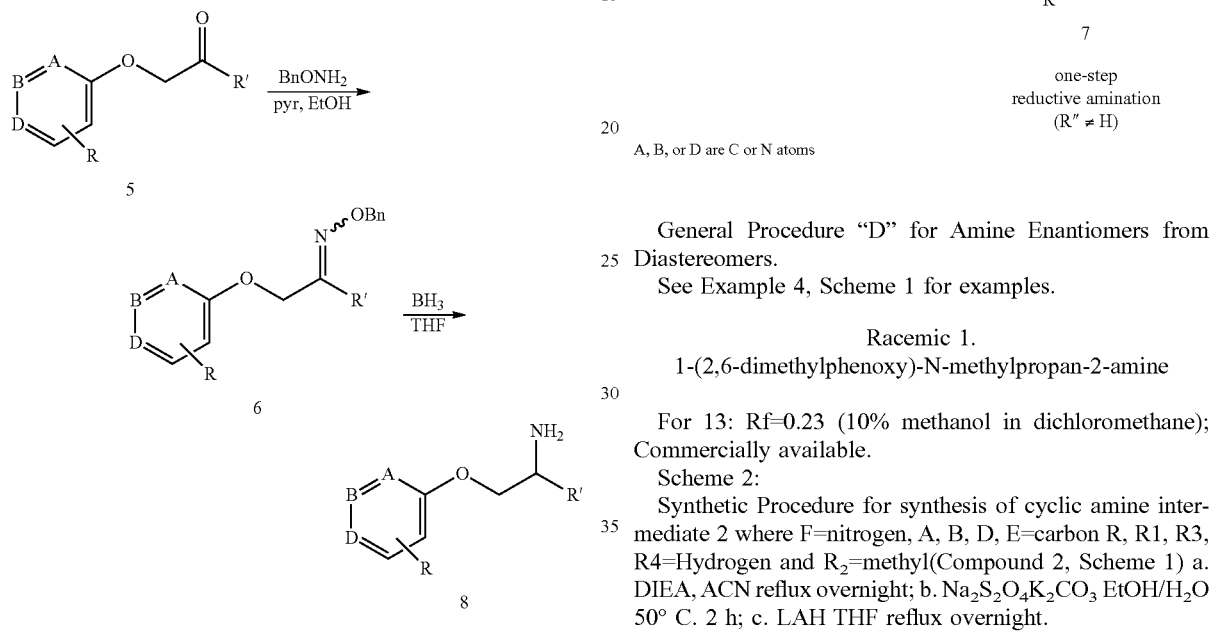

General Procedure "C" for Amines from Oximes.

O-benzylhydroxylamine (1.42 mmol, 2.1 eq.) and pyridine (1.74 mmol, 1.4 eq.) were added to a solution of 1-(aryloxy)propan-2-one (1.24 mmol, 1.0 eq.) in ethanol (12 mL) at 21° C. and the flask was immersed in a 45° C. oil bath. After 2 days, the mixture was concentrated, and the reaction concentrate was diluted with ethyl acetate and washed with water. The organic layer was dried (Na₂SO₄), filtered, and concentrated. The product was purified by silica gel flash column chromatography on a CombiFlash (0 to 70% ethyl acetate/hexanes) to provide oxime (1.14 mmol, >92% yield) as a pale yellow oil that was generally a 3.8:1.0 ratio of oxime isomers by 1H NMR.

Scheme 4.
Synthetic approach to N-substituted Mexiletine analogs and non-chiral analogs.

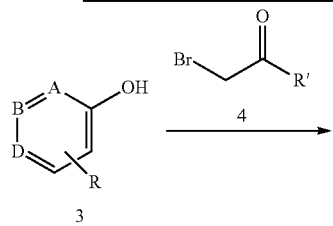

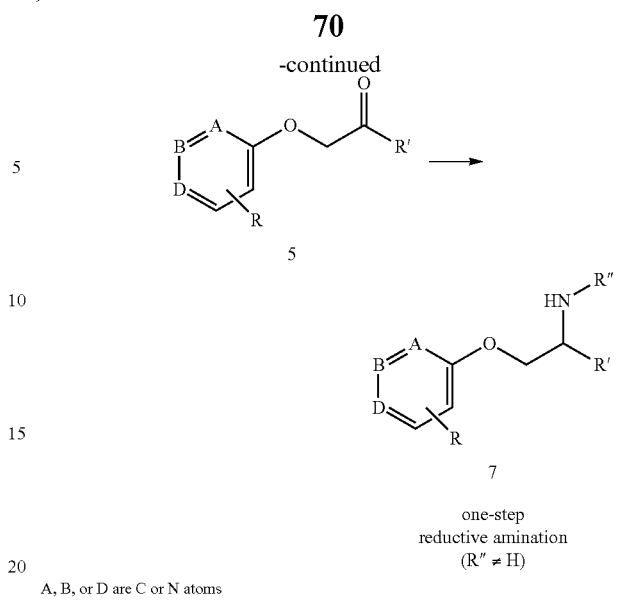

A, B, or D are C or N atoms

General Procedure "D" for Amine Enantiomers from Diastereomers.

See Example 4, Scheme 1 for examples.

Racemic 1.
1-(2,6-dimethylphenoxy)-N-methylpropan-2-amine

For 13: Rf=0.23 (10% methanol in dichloromethane); Commercially available.

Scheme 2:

Synthetic Procedure for synthesis of cyclic amine intermediate 2 where F=nitrogen, A, B, D, E=carbon R, R1, R3, R4=Hydrogen and R₂=methyl(Compound 2, Scheme 1) a. DIEA, ACN reflux overnight; b. Na₂S₂O₄K₂CO₃ EtOH/H₂O 50° C. 2 h; c. LAH THF reflux overnight.

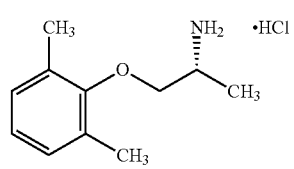

(R)-Mexiletine HCl

Compound (R)-2a (R)-(−)-Mexiletine Hydrochloride

Prepared from ($R_C$, $R_S$)-5 (60.7 mg, 0.213 mmol) using the general procedure provided (R)-1 hydrochloride (80% yield). (R)-1 had e.r.>99:1 (R:S) using chiral HPLC method described below. (R)-1 hydrochloride: ($^1$H NMR, $^{13}$C NMR, MS) in agreement with literature values. $[\alpha]_D^{20}$ −2.6 (c 0.62, CH₃OH); literature values $[\alpha]_D^{20}$ −2.9 (c 1.0, CH₃OH), $[\alpha]_D^{20}$ −2.4 (c 2.0, CH₃OH). $^1$H NMR for (R)-(−)-Mexiletine hydrochloride (300 MHz, CDCl₃): δ 8.77 (b, 2H), 6.97 (m, 3H), 6.99-6.89 (m, 3H), 4.00-3.89 (AB of ABX, $J_{AB}$=9.6 Hz, 2H), 3.79 (b, 1H), 2.32 (s, 6H), 1.64 (d, J=6.6 Hz, 3H) ppm. $^{13}$C{$^1$H} NMR (125 MHz, CDCl₃): δ 154.7, 130.9, 129.2, 124.7, 71.8, 48.5, 16.8, 15.8 ppm. LRMS (ESI-TOF) m/z calc. for C₁₁H₁₇NO [M+H⁺] 180.1; found 180.1.

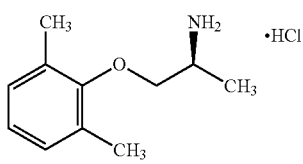

(S)-Mexiletine HCl

Compound (S)-2b. (S)-(+)-Mexiletine Hydrochloride

Prepared from (S$_C$,R$_S$)-5 using the procedure that provided (S)-1 hydrochloride (79% yield). (S)-1: e.r.>99 (S:R) using chiral HPLC. (S)-1 hydrochloride: ($^1$H NMR, $^{13}$C NMR, MS) in agreement with literature values and identical to (R)-1 characterized above. $[\alpha]_D^{20}$ +2.1 (c 0.66, CH$_3$OH); literature values $[\alpha]_D^{20}$ +2.6 (c 1.0, CH$_3$OH), $[\alpha]_D^{20}$ +2.2 (c 2.0, CH$_3$OH).

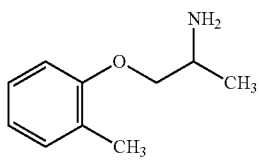

Compound 9

1-(2-Methylphenoxy)propan-2-amine, was made following the general method, above (83% yield) as a pale yellow oil: Rf=0.2 (15% MeOH/CH$_2$Cl$_2$): $^1$H NMR (300 MHz, CDCl$_3$) δ 7.16 (m, 2H, HAr), 6.87 (td, J=7.5, 1.1 Hz, 1H, HAr), 6.82 (m, 1H, HAr), 3.93-3.70 (AB of ABX, J$_{AB}$=8.8 Hz, 2H, CH$_2$), 3.41 (m, 1H, CH), 2.27 (s, 3H, CH$_3$), 1.23 (d, J=6.6 Hz, 1H, CH$_3$) ppm. ESI/MS for C$_{10}$H$_{15}$NO: calc. [M+H]$^+$=166.1, found m/z=166.1.

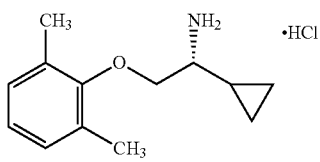

Compound (R)-10 (R)-1-cyclopropyl-2-(2,6-dimethylphenoxy)ethan-1-amine hydrochloride. [DAR-V-143] and [DAR-V-196]

Prepared from (R$_C$,S$_S$)-5 as above (13% yield). (R)-1 had e.r.>96 (R:S) using chiral HPLC. $[\alpha]_D^{20}$ −19 (c 0.41, CH$_3$OH); LRMS (ESI-TOF) m/z calc for C$_{13}$H$_{19}$NO [M+H$^+$] 206.2; found 206.0.

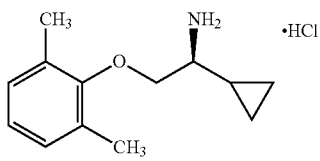

Compound (S)-10 (S)-1-cyclopropyl-2-(2,6-dimethylphenoxy)ethan-1-amine hydrochloride Prepared from (S$_C$, S$_S$)-5 using the general procedure provided (S)-1 hydrochloride (49% yield). (S)-1 had e.r.>96 (R:S) using chiral HPLC. $[\alpha]_D^{20}$ +30 (c 0.36, CH$_3$OH); $^1$H NMR (300 MHz, CDCl$_3$): δ 8.91 (b, 2H), 6.95 (m, 3H), 4.11 (m, 2H), 2.82 (m, 1H), 2.33 (s, 6H), 1.45 (m, 1H), 0.86 (m, 1H), 0.75 (m, 2H), 0.45 (m, 1H) ppm. LRMS (ESI-TOF) m/z calc for C$_{13}$H$_{19}$NO [M+H$^+$] 206.2; found 206.0.

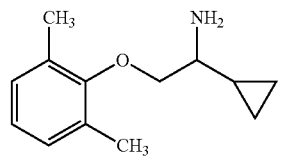

Compound rac 10. 1-cyclopropyl-2-(2,6-dimethylphenoxy)ethanamine, was made according to the general procedure above (85% yield) as a pale yellow oil/solid. Rf=0.17 (10% MeOH/CH2Cl2): $^1$H NMR (300 MHz, CDCl$_3$) δ 7.03-6.90 (m, 3H, HAr), 3.90-3.77 (AB of ABX, J$_{AB}$=9.0 Hz, 2H, CH$_2$), 2.41 (m, 1H, overlapping with neighboring peak, CH), 2.32 (s, 6H, 2×CH$_3$), 0.96 (m, 1H, CH), 0.57 (m, 2H), 0.32 (m, 2H) ppm.

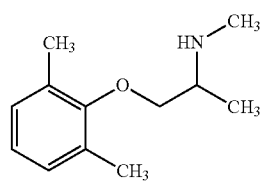

Compound 11

1-(2,6-dimethylphenoxy)-N-methylpropan-2-amine, [DAR-III-149] was made according to the general procedure above (38% yield) as a pale yellow oil/solid. Rf=0.23 10% MeOH/CH2Cl2): $^1$H NMR (300 MHz, CDCl$_3$) δ 7.02-6.93 (m, 3H, HAr), 6.43 (broad s, 1H), 3.93 (m, 2H, CH$_2$), 3.58 (m, 1H, CH), 2.86 (s, 3H, NCH$_3$), 2.30 (s, 6H, 2×CH$_3$), 1.52 (d, J=6.6 Hz, 3H, CH$_3$) ppm.

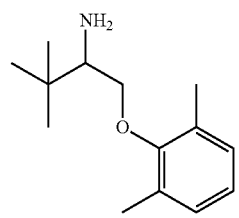 [SMILES: Cc1cccc(C)c1OCC(N)C(C)(C)C]

Compound 12.
1-(2,6-dimethylphenoxy)-3,3-dimethylbutan-2-amine

ESI/MS: calculated C$_{14}$H$_{23}$NO m/z=221.2, found m/z=222.0 [M+H]. $^1$H NMR (CDCl$_3$): 1.03 (s, 9H), 2.31 (s, 6H), 3.12-3.16 (m, 1H), 3.75-3.87 (m, 2H), 6.89-6.94 (m, 1H), 6.96-7.02 (m, 2H).

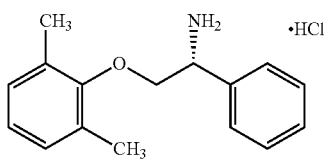 [SMILES: Cc1cccc(C)c1OC[C@H](N)c1ccccc1 ; Cl]

Compound (R)-13 (R)-(+)-2-(2,6-dimethylphenoxy)-1-phenylethanamine hydrochloride Prepared from ($S_C$, $R_S$)-8 as above (78% yield). ($^1$H NMR, $^{13}$C NMR, HRMS) in agreement with literature values. $[\alpha]_D^{20}$ −4.0 (c 0.63, MeOH); literature for (S)-enantiomer $[\alpha]_D^{20}$ +3.5 (c 0.48, MeOH). $^1$H NMR for (R)-(+)-2-(2,6-dimethylphenoxy)-1-phenylethanamine hydrochloride (300 MHz, CD$_3$OD): δ 7.56-7.44 (m, 5H), 7.01-6.89 (m, 3H), 4.78 (X of ABX, 1H), 4.16-4.04 (AB of ABX, $J_{AB}$=10.4 Hz, 2H), 2.20 (s, 6H) ppm. $^{13}$C{$^1$H} NMR (125 MHz, CD$_3$OD): δ 155.6, 135.4, 131.4, 130.6, 130.3, 130.1, 128.5, 125.8, 72.9, 56.7, 16.2 ppm. HRMS (ESI-TOF) m/z calc for $C_{16}H_{19}NO$ [M+Na$^+$] 264.1364; found 264.137.

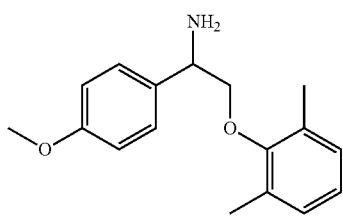

Compound 14. 2-(2,6-dimethylphenoxy)-1-(4-methoxyphenyl)ethanamine

ESI/MS: m/z=[M+H]$^1$H NMR (CDCl$_3$): 2.26 (s, 6H), 3.79-3.82 (m, 2H), 3.80 (s, 3H), 4.39-4.43 (m, 1H), 6.85-6.92 (m, 3H), 6.97-6.99 (m, 2H), 7.36 (s, J=8.8 Hz, 2H).

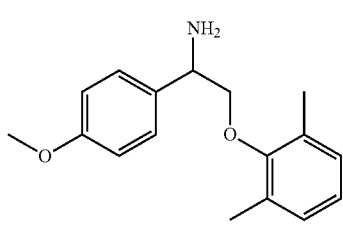 [SMILES: COc1ccc(C(N)COc2c(C)cccc2C)cc1]

Compound 15. 2-(2,6-dimethylphenoxy)-1-(4-methoxyphenyl)ethanamine

ESI/MS: m/z=[M+H]$^1$H NMR (CDCl$_3$): 2.26 (s, 6H), 3.79-3.82 (m, 2H), 3.80 (s, 3H), 4.39-4.43 (m, 1H), 6.85-6.92 (m, 3H), 6.97-6.99 (m, 2H), 7.36 (s, J=8.8 Hz, 2H).

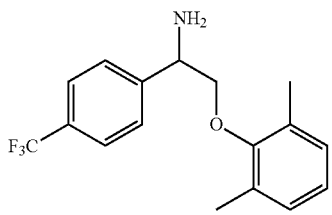 [SMILES: Cc1cccc(C)c1OCC(N)c1ccc(C(F)(F)F)cc1]

Compound 16. 2-(2,6-dimethylphenoxy)-1-(4-(trifluoromethyl)phenyl)ethanamine

ESI/MS: m/z=[M+H]. $^1$H NMR (CDCl$_3$): 2.23 (s, 6H), 3.78-3.88 (m, 2H), 4.51 (dd, J=4.4 Hz and 4.4 Hz, 1H), 6.88-6.93 (m, 1H), 6.97-7.00 (m, 2H), 7.56-7.72 (m, 4H).

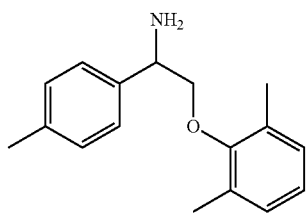 [SMILES: Cc1ccc(C(N)COc2c(C)cccc2C)cc1]

Compound 17. 2-(2,6-dimethylphenoxy)-1-p-tolylethanamine

ESI/MS: m/z=[M+H]. $^1$H NMR (CDCl$_3$): 2.29 (s, 6H), 2.36 (s, 3H), 3.78-3.87 (m, 2H), 4.43 (dd, J=4.1 Hz and 8.0 Hz, 1H), 6.88-6.93 (m, 1H), 6.98-7.01 (m, 2H), 7.17 (d, J=8.0 Hz, 2H), 7.33 (d, J=8.0 Hz, 2H).

Compound 18

$^1$H NMR (499 MHz, Chloroform-d) δ 4.70 (s, 2H), 5.38 (s, 2H), 6.24 (td, J=1.3, 6.7 Hz, 1H), 6.62 (d, J=9.1 Hz, 1H), 7.22 (dd, J=2.1, 6.8 Hz, 1H), 7.27-7.43 (m, 6H), 7.52 (t, J=7.8 Hz, 2H), 7.63 (td, J=1.3, 7.4 Hz, 1H), 8.01-8.06 (m, 2H).

Compound 19

$^1$H NMR (499 MHz, Chloroform-d) δ 2.16 (s, 3H), 4.70 (s, 2H), 5.35 (s, 2H), 6.17 (t, J=6.7 Hz, 1H), 7.09-7.15 (m, 1H), 7.26 (s, 1H), 7.27 (dd, J=1.1, 2.1 Hz, OH), 7.28-7.40 (m, 5H), 7.51 (t, J=7.8 Hz, 2H), 7.63 (dd, J=1.2, 14.9 Hz, OH), 7.63 (s, 1H), 8.01-8.07 (m, 2H).

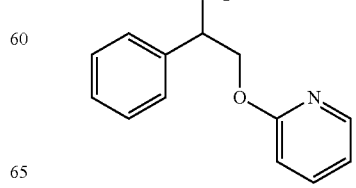

Compound 20.
1-phenyl-2-(pyridin-2-yloxy)ethanamine

ESI/MS: m/z=[M+H]. 1H NMR (CDCl3): 4.00 (dd, J=7.1 Hz and 13.7 Hz, 1H), 4.44 (dd, J=2.7 Hz and 13.7 Hz, 1H), 5.17 (dd, J=2.7 Hz and 7.7 Hz, 1H), 6.12 (t, J=6.6 Hz, 1H), 6.66 (d, J=9.3 Hz, 1H), 7.05 (dd, J=1.7 Hz and 6.6 Hz, 1H), 7.28-7.31 (m, 2H), 7.34-7.40 (m, 4H).

Compound 21

1H NMR (499 MHz, Chloroform-d) δ 2.19 (s, 3H), 4.02 (dd, J=7.7, 13.7 Hz, 1H), 4.41 (dd, J=2.7, 13.7 Hz, 1H), 5.17 (dd, J=2.7, 7.7 Hz, 1H), 6.05 (t, J=6.7 Hz, 1H), 6.94 (dd, J=1.9, 6.8 Hz, 1H), 7.21-7.29 (m, 1H), 7.25-7.33 (m, 1H), 7.35 (dd, J=6.7, 8.4 Hz, 2H), 7.36-7.43 (m, 2H).

Compound 22

1H NMR (300 MHz, Chloroform-d) δ 0.79 (s, 9H), 0.97 (s, 14H), 2.30 (s, 6H), 2.43 (s, 1H), 3.02 (dd, J=2.8, 9.4 Hz, 1H), 3.62 (t, J=9.1 Hz, 1H), 3.83 (s, 1H), 3.84 (dd, J=2.8, 8.9 Hz, 1H), 6.86-7.06 (m, 3H).

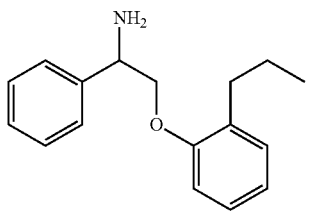 [SMILES: CCCc1ccccc1OCC(N)c1ccccc1]

Compound 23.
1-phenyl-2-(2-propylphenoxy)ethanamine

ESI/MS: calc. $C_{17}H_{21}NO$ m/z=255.2, found m/z=256.0 [M+1] $^1$H NMR (CDCl$_3$): 0.95 (t, J=7.4 Hz, 3H), 1.57 (sextet, J=7.4 Hz, 2H), 2.36 (bs, 2H), 2.56-2.61 (m, 2H), 3.98-4.04 (m, 1H), 4.11 (dd, J=4.4 Hz and 9.1 Hz, 1H), 4.44-4.48 (m, 1H), 6.77-6.80 (m, 1H), 6.84-6.90 (m, 1H), 7.08-7.14 (m, 2H), 7.29-7.38 (m, 4H), 7.44-7.47 (m, 1H).

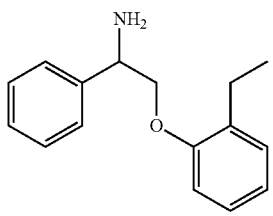 [SMILES: CCc1ccccc1OCC(N)c1ccccc1]

Compound 24.
1-phenyl-2-(2-ethoxyphenoxy)ethanamine

ESI/MS: calc. $C_{16}H_{19}NO$ m/z=241.2, found m/z=242.0 [M+1]. $^1$H NMR (CDCl$_3$): 1.18 (t, J=7.4 Hz, 3H), 2.52 (bs, 2H), 2.65 (q, J=7.4 Hz, 2H), 3.99-4.05 (m, 1H), 4.12 (dd, J=4.1 Hz and 9.1 Hz, 1H), 4.45-4.49 (m, 1H), 6.77-6.80 (m, 1H), 6.86-6.91 (m, 1H), 7.08-7.15 (m, 2H), 7.29-7.38 (m, 4H), 7.44-7.47 (m, 1H).

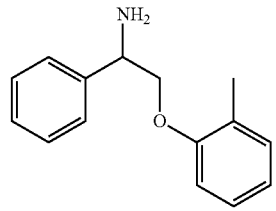 [SMILES: Cc1ccccc1OCC(N)c1ccccc1]

Compound 25. 1-phenyl-2-(o-tolyloxy)ethanamine

ESI/MS: calc. $C_{15}H_{17}NO$ m/z=227.1, found m/z=228.0 [M+1]. $^1$H NMR (CDCl$_3$): 2.24 (s, 3H), 2.88 (bs, 2H), 3.98-4.05 (m, 1H), 4.13 (dd, J=4.1 Hz and 9.1 Hz, 1H), 4.45-4.49 (m, 1H), 6.75-6.78 (m, 1H), 6.83-6.88 (m, 1H), 7.08-7.13 (m, 2H), 7.29-7.37 (m, 4H), 7.44-7.47 (m, 1H).

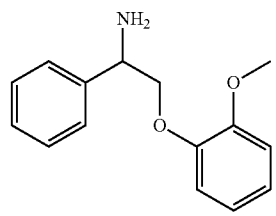 [SMILES: COc1ccccc1OCC(N)c1ccccc1]

Compound 26.
2-(2-methoxyphenoxy)-1-phenylethanamine

ESI/MS: calc. $C_{15}H_{17}NO$ m/z=243.1, found m/z=244.0 [M+1] $^1$H NMR (CDCl$_3$): 2.68 (bs, 2H), 3.79 (m, 3H), 4.05-4.11 (m, 1H), 4.15-4.20 (m, 1H), 4.48-4.52 (m, 1H), 6.86-6.98 (m, 4H), 7.30-7.39 (m, 4H), 7.47-7.50 (m, 1H).

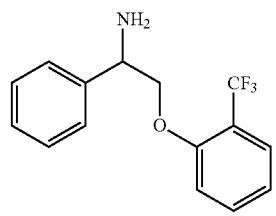 [SMILES: NC(COc1ccccc1C(F)(F)F)c1ccccc1]

Compound 27.
1-phenyl-2-(2-(trifluoromethyl)phenoxy)ethanamine

ESI/MS: calc. $C_{15}H_{14}F_3NO$ m/z=281.1, found m/z=282.0 [M+1] $^1$H NMR (CDCl$_3$): 2.38 (bs, 2H), 4.02-4.11 (m, 1H), 4.19-4.27 (m, 1H), 4.48-4.58 (m, 1H), 6.91-6.94 (m, 1H), 6.98-7.03 (m, 1H), 7.29-7.42 (m, 4H), 7.44-7.49 (m, 2H), 7.54-7.58 (m, 1H).

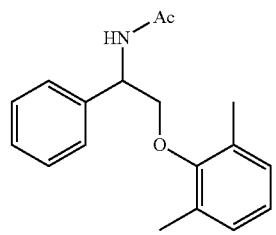 [SMILES: CC(=O)NC(COc1c(C)cccc1C)c1ccccc1]

Compound 28.
N-(2-(2,6-dimethylphenoxy)-1-phenylethyl)acetamide

ESI/MS: calc. $C_{18}H_{21}NO_2$ m/z=283.2, found m/z=284.0 [M+1] $^1$H NMR (CDCl$_3$): 2.11 (s, 6H), 3.98-4.10 (m, 2H), 5.33-5.39 (m, 1H), 6.39-6.43 (m, 1H), 6.87-6.98 (m, 3H) 7.29-7.43 (m, 4H).

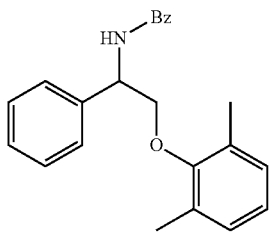

Compound 29.
N-(2-(2,6-dimethylphenoxy)-1-phenylethyl)benzamide

ESI/MS: calc. $C_{23}H_{23}NO_2$ m/z=345.2, found m/z=346.0 [M+1]. $^1$H NMR (CDCl$_3$): 2.13 (s, 6H), 4.11 (dd, J=3.9 Hz and 9.4 Hz, 1H), 4.21 (dd, J=4.4 Hz and 9.4 Hz, 1H), 5.52-5.58 (m, 1H), 6.39-6.43 (m, 1H), 6.88-6.98 (m, 4H), 7.15-7.18 (m, 1H), 7.30-7.41 (m, 4H), 7.44-7.53 (m, 4H), 7.84-7.88 (1H).

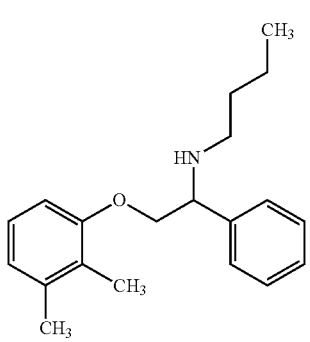 [SMILES: CCCCNC(COc1cccc(C)c1C)c1ccccc1]

Compound 30

2-(2,3-dimethylphenoxy)-N-butyl-1-phenylethanamine was made according to the general method above 66% yield) as a pale yellow oil that solidified over time. Rf=0.25 (2% MeOH/CH2Cl2) 7.49-7.46 (m, 2H, HAr), 7.41-7.29 (m, 3H, HAr), 7.02 (t, J=8.0 Hz, 1H, HAr), 6.79 (d, J=7.4 Hz, 1H, HAr), 6.67 (d, J=8.0 Hz, 1H, HAr), 4.17 (app dd, J=8.2, 3.9 Hz, 1H, CH), 4.10-3.99 (m, 2H, CH$_2$), 2.59 (t, J=6.9 Hz, 2H, CH$_2$), 2.30 (s, 3H, CH$_3$), 2.19 (s, 3H, CH$_3$), 1.54 (m, 2H, CH$_2$), 1.40 (m, 2H, CH$_2$), 0.94 (t, J=7.4 Hz, 3H, CH$_3$) ppm.

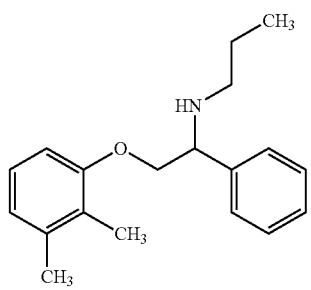 [SMILES: CCCNC(COc1cccc(C)c1C)c1ccccc1]

Compound 31

2-(2,3-dimethylphenoxy)-N-propyl-1-phenylethanamine was made by the method above (66% yield) as a pale yellow oil that solidified over time. Rf=0.23 (2% MeOH/CH$_2$Cl$_2$); $^1$H NMR (300 MHz, CDCl$_3$) δ 7.50-7.46 (m, 2H, HAr), 7.42-7.29 (m, 3H, HAr), 7.03 (t, J=7.7 Hz, 1H, HAr), 6.79 (d, J=7.1 Hz, 1H, HAr), 6.68 (d, J=8.0 Hz, 1H, HAr), 4.18 (app dd, J=8.5, 4.1 Hz, 1H, CH), 4.10-3.99 (m, 2H, CH$_2$), 2.56 (t, J=7.1 Hz, 2H, CH$_2$), 2.30 (s, 3H, CH$_3$), 2.19 (s, 3H, CH$_3$), 1.58 (m, 2H, CH$_2$), 0.96 (t, J=7.7 Hz, 3H, CH$_3$) ppm.

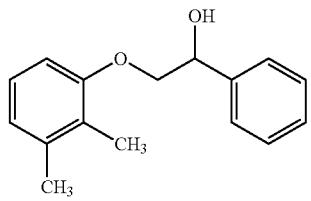 [SMILES: Cc1cccc(OCC(O)c2ccccc2)c1C]

Compound 32

2-(2,3-dimethylphenoxy)-1-phenylethanol, Rf=0.73 (2% methanol in dichloromethane); $^1$H NMR (300 MHz, CDCl$_3$) δ 7.50-7.46 (m, 2H, HAr), 7.44-7.31 (m, 3H, HAr), 7.04 (t, J=8.0 Hz, 1H, HAr), 6.82 (d, J=7.4 Hz, 1H, HAr), 6.69 (d, J=8.2 Hz, 1H, HAr), 5.17 (dd, J=8.5, 3.6 Hz, 1H, CH), 4.15-4.00 (AB of ABX, J$_{AB}$=9.6 Hz, 2H, CH$_2$), 2.31 (s, 3H, CH$_3$), 2.21 (s, 3H, CH$_3$) ppm.

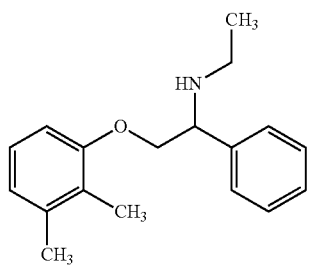 [SMILES: CCNC(COc1cccc(C)c1C)c1ccccc1]

Compound 33

2-(2,3-dimethylphenoxy)-N-ethyl-1-phenylethanamine, was made according to the general procedure above (97% yield) as a pale yellow oil that solidified over time. Rf=0.18 (4% MeOH/CH2Cl2): $^1$H NMR (300 MHz, CDCl$_3$) δ 7.49-7.46 (m, 2H, HAr), 7.41-7.29 (m, 3H, HAr), 7.01 (t, J=8.0

Hz, 1H, HAr), 6.78 (d, J=7.4 Hz, 1H, HAr), 6.68 (d, J=8.3 Hz, 1H, HAr), 4.20 (app dd, J=8.0, 4.7 Hz, 1H, CH), 4.12-4.03 (m, 2H, CH$_2$), 2.64 (q, J=7.2 Hz, 2H, CH$_2$), 2.29 (s, 3H, CH$_3$), 2.17 (s, 3H, CH$_3$), 1.17 (t, J=7.1 Hz, 3H, CH$_3$) ppm.

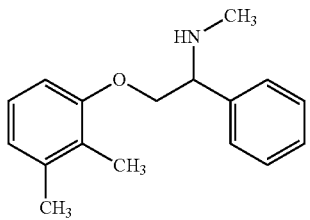 [SMILES: CNC(COc1cccc(C)c1C)c1ccccc1]

Compound 34

2-(2,3-dimethylphenoxy)-N-methyl-1-phenylethanamine, was prepared by the general method above (97% yield) as a pale yellow oil that solidified over time. Rf=0.33 (5% MeOH/CH2Cl2): $^1$H NMR (300 MHz, CDCl$_3$) δ 7.48-7.46 (m, 2H, HAr), 7.42-7.3 (m, 3H, HAr), 7.01 (t, J=7.7 Hz, 1H, HAr), 6.78 (d, J=7.4 Hz, 1H, HAr), 6.68 (d, J=8.3 Hz, 1H, HAr), 4.02 (m, 3H, CH, CH$_2$), 2.42 (s, 3H, NCH$_3$), 2.29 (s, 3H, CH$_3$), 2.18 (s, 3H, CH$_3$) ppm.

Compound 35

2-(2,3-dimethylphenoxy)-1-phenylethanamine, was made according to the above procedure (58% yield) as a pale yellow oil that solidified over time. Rf=0.27 (5% MeOH/CH2Cl2); $^1$H NMR (300 MHz, CDCl$_3$) δ 7.5-7.47 (m, 2H, HAr), 7.42-7.28 (m, 3H, HAr), 7.03 (t, J=7.7 Hz, 1H, HAr), 6.79 (d, J=7.5 Hz, 1H, HAr), 6.68 (d, J=8.0 Hz, 1H, HAr), 4.47 (dd, J=7.7, 3.8 Hz, 1H, CH), 4.13-3.95 (AB of ABX, J$_{AB}$=9.1 Hz, 2H, CH$_2$), 2.39 (broad s, 2H, NH$_2$), 2.30 (s, 3H, CH$_3$), 2.19 (s, 3H, CH$_3$) ppm.

Compound 36. 2-(2,3-dimethylphenoxy)-N-methoxy-ethyl-1-phenylethanamine $^1$H NMR (300 MHz, Chloroform-d) δ 1.27 (d, J=6.5 Hz, 7H), 2.29 (s, 6H), 3.58-3.79 (m, 2H), 4.14-4.31 (m, 1H), 6.92 (dd, J=6.2, 8.4 Hz, 1H), 6.96-7.05 (m, 2H), 7.25 (s, 1H).

Compound 37

$^1$H NMR (300 MHz, Chloroform-d) δ 0.98 (t, J=7.4 Hz, 3H), 1.19 (d, J=6.4 Hz, 3H), 1.52-1.69 (m, 4H), 2.29 (s, 6H), 2.48 (s, 1H), 2.70 (dddd, J=6.8, 8.0, 11.1, 38.0 Hz, 2H), 3.07-3.21 (m, 1H), 3.62-3.77 (m, 2H), 6.85-7.05 (m, 3H).

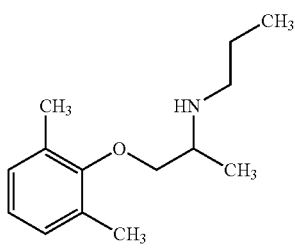 [SMILES: CCCNC(C)COc1c(C)cccc1C]

Compound 38

1-(2,6-dimethylphenoxy)-N-propylpropan-2-amine, was made following the general method above (38% yield) as a pale yellow oil that solidified over time. Rf=0.24 (10% MeOH/CH2Cl2): $^1$H NMR (300 MHz, CDCl$_3$) δ 7.03-6.90 (m, 3H, HAr), 3.70 (m, 2H, CH$_2$), 3.17 (m, 1H, CH), 2.82-2.62 (m, 2H, CH$_2$), 2.50 (broad s, 1H), 2.31 (s, 6H, 2×CH$_3$), 1.62 (m, 2H, CH$_2$), 1.28 (d, J=6.6 Hz, 3H, CH$_3$), 0.99 (t, J=7.4 Hz, 3H, CH$_3$) ppm.

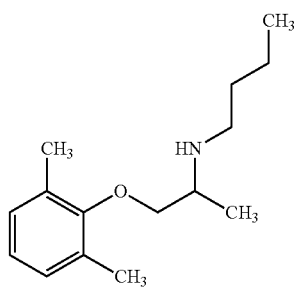 [SMILES: CCCCNC(C)COc1c(C)cccc1C]

Compound 39

1-(2,6-dimethylphenoxy)-N-butylpropan-2-amine, was made according to the general procedure above (60% yield) as a pale yellow oil that solidified over time. Rf=0.31 (10% MeOH/CH$_2$Cl$_2$): $^1$H NMR (300 MHz, CDCl$_3$) δ 7.02-6.91 (m, 3H, HAr), 4.21 (broad s, 1H, NH), 3.83-3.73 (AB of ABX, J$_{AB}$=9.6 Hz, 2H, CH$_2$), 3.27 (m, 1H, CH), 2.95-2.76 (m, 2H, CH$_2$), 2.30 (s, 6H, 2×CH$_3$), 1.65 (m, 2H, CH$_2$), 1.43 (m, 2H, CH$_2$), 1.28 (d, J=6.6 Hz, 3H, CH$_3$), 0.98 (t, J=7.2 Hz, 3H, CH$_3$) ppm.

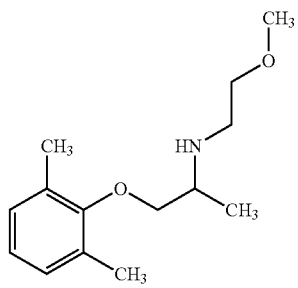 [SMILES: COCCNC(C)COc1c(C)cccc1C]

Compound 40.
1-(2,6-dimethylphenoxy)-N-methoxy-ethyl-2-amine

Rf=0.36 (10% MeOH in DCM); $^1$H NMR (300 MHz, CDCl$_3$) δ 7.02-6.89 (m, 3H, HAr), 3.76-3.67 (m, 2H, CH$_2$), 3.59 (app t, J=4.9 Hz, 2H), 3.40 (s, 3H, OCH$_3$), 3.22-3.12 (m, 2H, CH$_2$), 3.01-2.85 (m, 2H, CH$_2$), 2.54 (broad s, 1H, NH), 2.31 (s, 6H, 2×CH$_3$), 1.22 (d, J=6.6 Hz, 3H, CH$_3$) ppm.

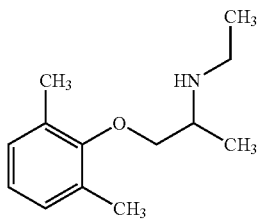

Compound 41

1-(2,6-dimethylphenoxy)-N-ethylpropan-2-amine, was made following the general method above (40% yield) as a pale yellow oil that solidified over time. Rf=0.19 (10% MeOH/CH2Cl2): $^1$H NMR (300 MHz, CDCl$_3$) δ 7.02-6.92 (m, 3H, HAr), 6.23 (broad s, 1H), 4.03-3.96 (AB of ABX, $J_{AB}$=10.1 Hz, 2H, CH$_2$), 3.61 (m, 1H, CH), 3.24 (m, 2H, CH$_2$), 2.30 (s, 6H, 2×CH$_3$), 1.51 (d, J=6.9 Hz, 3H, CH$_3$), 1.45 (t, J=6.4 Hz, 3H, CH$_3$) ppm.

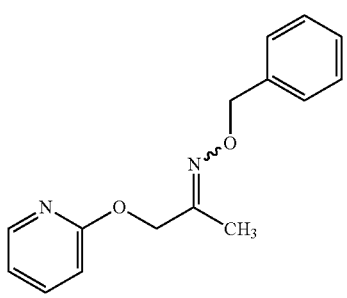 [SMILES: CC(COc1ccccn1)=NOCc1ccccc1]

Compound 42

1-(2,6-dimethylphenoxy)-N-benzylpropan-2-amine, was made according to the above general procedure (80% yield) as a beige solid. Rf=0.24 (5% MeOH/CH2Cl2): $^1$H NMR (300 MHz, CDCl$_3$) δ 7.40-7.3 (m, 4H, HAr), 7.27 (m, 1H, HAr, overlapping with solvent signal), 7.01 (m, 2H, HAr), 6.93 (m, 1H, HAr), 4.00-3.87 (AB quartet, J=13.1 Hz, 2H, CH$_2$), 3.77-3.69 (m, 2H, CH$_2$), 3.20 (m, 1H, CH), 2.29 (s, 6H, 2×CH$_3$), 1.22 (d, J=6.0 Hz, 3H, CH$_3$) ppm.

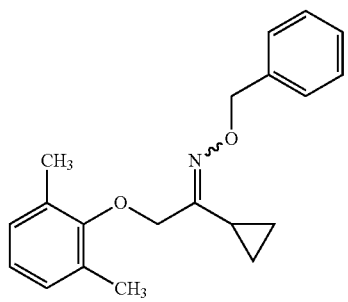

Compound 43

1-(2,6-dimethylphenoxy)-N-phenylpropan-2-amine, was made according to the general method above (61% yield) as a pale yellow oil. Rf=0.34 (20% EtOAc/hexanes): $^1$H NMR (300 MHz, CDCl$_3$) δ 7.20 (t, J=7.7 Hz, 2H, HAr), 7.00 (m, 2H, HAr), 6.92 (m, 1H, HAr), 6.75-6.69 (m, 3H, HAr), 4.13 (broad s, 1H), 3.89 (m, 1H, CH), 3.85-3.80 (m, 2H, CH$_2$), 2.27 (s, 6H, 2×CH$_3$), 1.47 (d, J=6.6 Hz, 3H, CH$_3$) ppm.

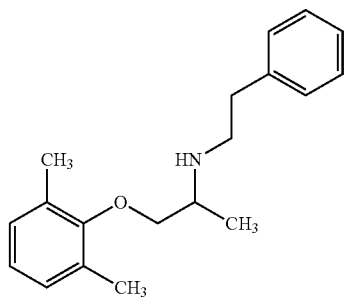 [SMILES: Cc1cccc(C)c1OCC(C)NCCc1ccccc1]

Compound 44

1-(2,6-dimethylphenoxy)-N-(2-phenylethyl)propan-2-amine, was made according to the above procedure (66% yield) as a beige solid. Rf=0.25 (5% MeOH/CH2Cl2): $^1$H NMR (300 MHz, CDCl$_3$) δ 7.31 (m, 2H, HAr), 7.26 (m, 2H, HAr, overlapping with solvent signal), 7.22 (t, J=7.1 Hz, 1H, HAr), 7.01 (m, 2H, HAr), 6.92 (m, 1H, HAr), 3.67 (m, 2H, CH$_2$), 3.15 (m, 1H, CH), 3.06 (m, 1H, CH), 2.96-2.83 (m, 2H, CH$_2$), 2.25 (s, 6H, 2×CH$_3$), 1.18 (d, J=6.1 Hz, 3H, CH$_3$) ppm.

Compound 45

$^1$H NMR (499 MHz, Chloroform-d) δ 1.15-1.33 (m, 5H), 1.72 (dd, J=5.6, 9.7 Hz, 4H), 1.82-1.90 (m, 1H), 1.93 (d, J=4.6 Hz, 1H), 3.22 (tt, J=4.1, 9.5 Hz, 1H), 4.00 (s, 1.6H), 4.35 (s, 0.4H), 5.05 (s, 0.4H), 5.11 (s, 1.6H), 7.25-7.39 (m, 5H).

Compound 46

Rf=0.56 (5% ethyl acetate/hexanes); $^1$H NMR (300 MHz, CDCl$_3$, 2 isomers) δ 7.41-7.28 (m, 10H, HAr), 7.03-6.90 (m, 6H, HAr), 5.16 (s, 2H, CH$_2$), 5.03 (s, 2H, CH$_2$), 4.65 (s, 2H, CH$_2$), 4.15 (s, 2H, CH$_2$), 2.41 (m, 1H, CH), 2.31 (s, 6H, 2×CH$_3$), 2.27 (s, 6H, 2×CH$_3$), 2.05 (m, 1H, CH), 1.18 (m, 2H), 1.03-0.94 (m, 4H), 0.92-0.85 (m, 2H) ppm.

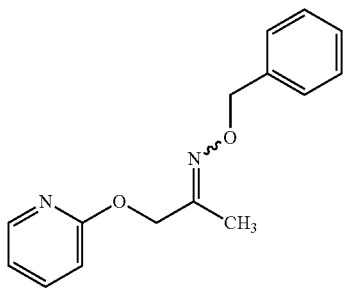 [SMILES: CC(COc1ccccn1)=NOCc1ccccc1]

Compound 47

1-(pyridin-2-yloxy)propan-2-one O-benzyl oxime, Rf=0.28 (75% ethyl acetate/hexanes); $^1$H NMR (300 MHz, CDCl$_3$) δ 7.37-7.30 (m, 5H, HAr), 7.19 (m, 1H, HAr), 6.60 (m, 1H, HAr), 6.16 (td, J=6.8, 1.3 Hz, 1H, HAr), 5.12 (s, 2H, CH$_2$), 4.70 (s, 2H, CH$_2$), 1.89 (s, 3H, CH$_3$) ppm.

General Procedure for Synthesis of (Pyridin-2-yloxy)propan-2-amine, Compound 48

A 1M solution of borane-tetrahydrofuran complex in THF (5.0 eq.) was added to a stirred solution of 1-(pyridin-2-yloxy)propan-2-one O-benzyl oxime (1.0 eq.) in THF (3.8 mL) at 21° C. After 14 hours, the reaction was stopped by dropwise addition of 1 M HCl$_{(aq)}$ (pH 3) and then 10% (wt/wt) Na$_2$CO$_{3(aq)}$ was added (pH 9), Celite (3 mL) was added, concentrated and dry-loaded onto a silica gel column and flashed using gradient elution (10% methanol in CH2Cl2 initial, then 1% NH$_4$OH$_{(aq)}$/20% MeOH/79% CH2Cl2). The isolated product was dissolved in 20% MeOH/CH2Cl2, filtered through a Whatman #1 filter paper and concentrated to give 23 (50% yield) as a pale yellow solid. For 23: Rf=0.46 (1% NH$_4$OH$_{(aq)}$/20% MeOH/79% CH2Cl2): $^1$H NMR (300 MHz, CD$_3$OD) δ 7.69 (dd, J=6.6, 1.9 Hz, 1H, HAr), 7.57 (overlapping ddd, J=9.0, 6.8, 2.2 Hz, 1H, HAr), 6.58 (d, J=7.8 Hz, 1H, HAr), 6.44 (td, J=6.6, 1.1 Hz, 1H, HAr), 4.32-4.16 (AB of ABX, J$_{AB}$=14.0 Hz, 2H, CH$_2$), 3.76 (m, 1H, CH), 1.36 (d, J=6.9 Hz, 1H, CH$_3$) ppm. ESI/MS for C$_8$H$_{12}$N$_2$O: calc. [M+H]$^+$=153.1, found m/z=153.1.

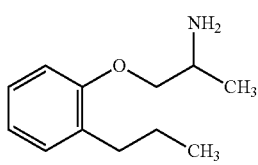

Compound 49

1-(2-Propylphenoxy)propan-2-amine was made following the above procedure (94% yield) as a pale yellow oil. Rf=0.24 (15% MeOH/CH2Cl2): $^1$H NMR (300 MHz, CDCl$_3$) δ 7.15 (m, 2H, HAr), 6.89 (td, J=7.4, 1.4 Hz, 1H, HAr), 6.82 (m, 1H, HAr), 3.92-3.70 (AB of ABX, J$_{AB}$=8.8 Hz, 2H, CH$_2$), 3.41 (m, 1H, CH), 2.64 (t, J=7.5 Hz, 2H, CH$_2$), 1.64 (m, 2H, CH$_2$), 1.23 (d, J=6.6 Hz, 1H, CH$_3$), 0.98 (t, J=7.1 Hz, 3H, CH$_3$) ppm. ESI/MS for C$_{12}$H$_{19}$NO: calculated [M+H]$^+$=194.1, found m/z=194.1.

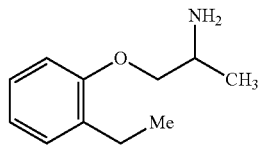

Compound 50

1-(2-Ethylphenoxy)propan-2-amine was made according to the procedure above (76% yield) as a pale yellow oil. Rf=0.22 (15% MeOH/CH2Cl2): $^1$H NMR (300 MHz, CDCl$_3$) δ 7.16 (m, 2H, HAr), 6.92 (td, J=7.4, 1.1 Hz, 1H, HAr), 6.82 (dd, J=8.8, 0.9 Hz, 1H, HAr), 3.92-3.71 (AB of ABX, J$_{AB}$=9.0 Hz, 2H, CH$_2$), 3.41 (m, 1H, CH), 2.69 (q, J=7.5 Hz, 2H, CH$_2$), 1.24 (t, J=7.5 Hz, 3H, CH$_3$), 1.23 (d, J=6.6 Hz, 1H, CH$_3$) ppm. ESI/MS for C$_{11}$H$_{17}$NO: calculated [M+H]$^+$=180.1, found m/z=180.1.

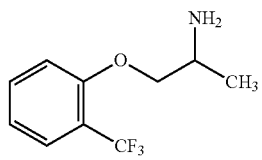

Compound 51

1-(2-(Trifluoromethyl)phenoxy)propan-2-amine was made by the general procedure (71% yield) as a pale yellow oil. Rf=0.16 (15% MeOH/CH2Cl2): $^1$H NMR (300 MHz, CDCl$_3$) δ 7.57 (dd, J=7.7, 1.3 Hz, 1H, HAr), 7.48 (m, 1H, HAr), 7.00 (m, 2H, HAr), 4.03-3.76 (AB of ABX, J$_{AB}$=8.5 Hz, 2H, CH$_2$), 3.44 (m, 1H, CH), 1.23 (d, J=6.6 Hz, 1H, CH$_3$) ppm. ESI/MS for C$_{10}$H$_{12}$F$_3$NO: calc. [M+H]$^+$=220.1, found m/z=220.0.

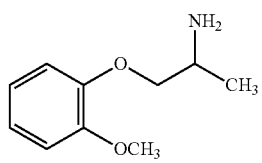

Compound 52

1-(2-Methoxyphenoxy)propan-2-amine was made following the general procedure above (74% yield) as a pale yellow oil. Rf=0.29 (15% MeOH/CH2Cl2): $^1$H NMR (300 MHz, CDCl$_3$) δ 6.96-6.88 (m, 4H, HAr), 3.98-3.70 (AB of ABX, J$_{AB}$=9.4 Hz, 2H, CH$_2$), 3.88 (s, 3H, OCH$_3$), 3.41 (m, 1H, CH), 1.20 (d, J=6.6 Hz, 1H, CH$_3$) ppm. ESI/MS for C$_{10}$H$_{15}$NO$_2$: calculated [M+H]$^+$=182.1, found m/z=182.0.

Compound 53

$^1$H NMR (300 MHz, Chloroform-d) δ 1.41 (d, J=6.8 Hz, 2H), 2.04 (s, 3H), 2.26 (s, 6H), 3.66-3.86 (m, 2H), 4.28-4.44 (m, 1H), 5.93 (s, 1H), 6.86-7.08 (m, 3H).

Compound 54

¹H NMR (300 MHz, Chloroform-d) δ 1.54 (d, J=6.8 Hz, 3H), 2.28 (s, 6H), 3.78-4.00 (m, 2H), 3.90 (s, 2H), 3.95 (dd, J=3.8, 9.1 Hz, 1H), 4.57 (m, 1H), 6.64 (d, J=8.4 Hz, 1H), 6.87-7.05 (m, 3H), 7.38-7.57 (m, 3H), 7.73-7.92 (m, 2H).

Compound 55

ESI/MS calculated for $C_{11}H_{17}NO$ m/z: 179.1, found m/z=180.0 [M+H]⁺.

Compound 56

¹H NMR (300 MHz, Methanol-d₄) δ 1.45 (dd, J=1.5, 6.7 Hz, 3H), 2.35 (s, 3H), 3.85-4.20 (m, 2H), 7.04 (t, J=7.7 Hz, 1H), 7.17 (d, J=6.7 Hz, 1H), 7.25 (d, J=7.4 Hz, 1H).

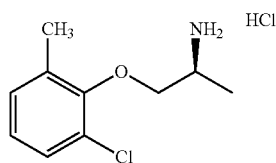

Compound 57. (S)-1-(2-chloro-6-methylphenoxy)propan-2-amine hydrochloride

ESI/MS: calculated $C_{10}H_{14}ClNO$ m/z=199.1, found m/z=200.0 [M+1] ¹H NMR (MeOH-d6): 1.32 (d, J=6.2 Hz, 3H), 2.32 (s, 3H), 3.82-3.96 (m, 3H), 4.18 (bs, 1H), 6.94 (t, J=7.8 Hz, 1H), 7.04-7.08 (m, 1H), 7.17-7.21 (m, 1H).

Compound 58

¹H NMR (300 MHz, Methanol-d₄) δ 1.45 (d, J=6.7 Hz, 2H), 3.70-3.81 (m, 1H), 4.06 (dd, J=6.7, 10.2 Hz, 1H), 4.24 (dd, J=3.8, 10.2 Hz, 1H), 7.01 (td, J=1.4, 7.6 Hz, 1H), 7.13 (dd, J=1.5, 8.3 Hz, 1H), 7.23-7.35 (m, 1H), 7.40 (dd, J=1.6, 7.9 Hz, 1H).

Compound 59

¹H NMR (300 MHz, Chloroform-d) δ 2.29 (t, J=0.6 Hz, 6H), 4.30 (s, 2H), 6.92-7.08 (m, 3H).

Compound 60

ESI/MS calculated for $C_{13}H_{19}NO$ m/z: 205.2, found m/z=206.0 [M+H]⁺.

Compound 61

ESI/MS calculated for $C_{13}H_{19}NO$ m/z: 205.2, found m/z=206.0 [M+H]⁺.

Compound 62

ESI/MS calculated for $C_{13}H_{19}NO$ m/z: 205.2, found m/z=206.0 [M+H]⁺.

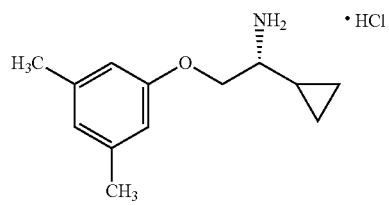

Compound (R—) 63a. (R)-1-cyclopropyl-2-(3,5-dimethylphenoxy)ethan-1-amine hydrochloride Prepared from $(R_C,S_S)$-5 using the general procedure provided (R)-1 hydrochloride (47% yield). LRMS (ESI-TOF) m/z calc for $C_{13}H_{19}NO$ [M+H⁺] 206.2; found 206.0.

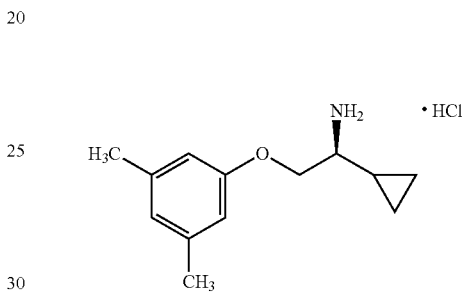

Compound (S)-63b. (S)-1-cyclopropyl-2-(2,6-dimethylphenoxy)ethan-1-amine hydrochloride Prepared from $(S_C,S_S)$-) using the above method, (49% yield). $[\alpha]_D^{20}$ +30 (c 0.36, CH₃OH); ¹H NMR (300 MHz, CDCl₃): δ 8.67 (b, 2H), 6.68 (s, 2H), 6.58 (s, 1H), 4.26 (m, 1H), 4.13 (m, 1H), 2.26 (s, 6H), 1.15 (m, 1H), 0.53 (m, 3H), 0.16 (m, 1H) ppm. LRMS (ESI-TOF) m/z calc for $C_{13}H_{19}NO$ [M+H⁺] 206.2; found 206.0.

Compound 64

¹H NMR (300 MHz, Methanol-d₄) δ 1.44 (d, J=6.7 Hz, 3H), 2.24 (broad s, 6H), 3.73 (pd, J=3.7, 6.7 Hz, 1H), 3.96 (dd, J=6.8, 10.3 Hz, 1H), 4.13 (dd, J=3.8, 10.3 Hz, 1H), 6.79 (d, J=7.9 Hz, 1H), 6.89-7.00 (m, 2H).

Compound 65

¹H NMR (300 MHz, Methanol-d₄) δ 0.45-0.63 (m, 2H), 0.78 (ddd, J=2.0, 3.8, 8.0 Hz, 2H), 1.11 (m, 1H), 2.24 (broad s, 6H), 2.84 (ddd, J=3.4, 6.3, 10.0 Hz, 1H), 4.06-4.28 (m, 2H), 6.77-6.86 (m, 1H), 6.90-7.00 (m, 2H).

Compound 66

¹H NMR (300 MHz, Methanol-d₄) δ 2.23 (d, J=2.1 Hz, 6H), 4.22-4.36 (m, 2H), 4.79 (dd, J=4.9, 7.1 Hz, 1H), 6.80 (d, J=8.1 Hz, 1H), 6.94 (m, 2H), 7.42-7.60 (m, 5H).

87

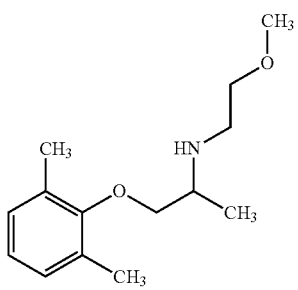

Compound 67

1-(2,6-dimethylphenoxy)-N-butylpropan-2-amine was made according to the general method above (52% yield) as a pale yellow oil that solidified over time. Rf=0.36 (10% MeOH/CH2Cl2): $^1$H NMR (300 MHz, CDCl$_3$) δ 7.02-6.89 (m, 3H, HAr), 3.76-3.67 (m, 2H, CH$_2$), 3.59 (app t, J=4.9 Hz, 2H), 3.40 (s, 3H, OCH$_3$), 3.22-3.12 (m, 2H, CH$_2$), 3.01-2.85 (m, 2H, CH$_2$), 2.54 (broad s, 1H, NH), 2.31 (s, 6H, 2×CH$_3$), 1.22 (d, J=6.6 Hz, 3H, CH$_3$) ppm.

Compound 68

$^1$H NMR (300 MHz, Methanol-d$_4$) δ 0.14-0.82 (m, 9H), 0.91-1.09 (m, 1H), 2.25 (s, 6H), 2.75-2.91 (m, 1H), 2.99-315 (m, 1H), 3.16-3.32 (m, 1H), 3.36 (dd, J=1.2, 4.5 Hz, 1H), 3.54 (td, J=2.2, 4.9 Hz, 1H), 3.80-4.14 (m, 2H), 6.54 (s, 2H), 6.56 (d, J=4.9 Hz, 1H).

Compound 69

$^1$H NMR (300 MHz, MeOH-d$_4$) δ 2.24 (d, J=0.7 Hz, 6H), 2.53-2.76 (m, 1H), 3.35 (s, 1H), 3.33-3.56 (m, 2H), 3.96-4.13 (m, 2H), 6.49-6.61 (m, 3H), 7.22-7.47 (m, 5H).

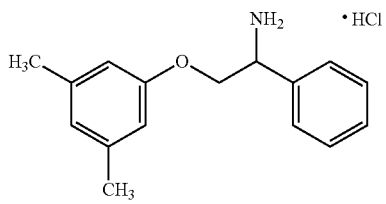

Compound 70. (rac)-(+)-2-(3,5-dimethylphenoxy)-1-phenylethanamine hydrochloride

Prepared from (rac)-8 by the general procedure provided the title product (83% yield): $^1$H NMR (300 MHz, CD$_3$OD): δ 7.56-7.46 (m, 5H), 6.64 (s, 3H), 4.74 (dd, J=8.3, 4.4 Hz, 1H), 4.35-4.24 (AB of ABX, J$_{AB}$=10.5 Hz, 2H), 2.27 (s, 6H) ppm. LRMS (ESI-TOF) m/z calc for C$_{16}$H$_{19}$NO [M+H$^+$] 242.2; found 242.0.

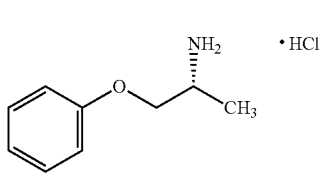

88

Compound (R—)-71.
(R)-1-phenoxypropan-2-amine hydrochloride

Prepared from (R$_C$, S$_S$)-5 above using the general procedure provided (R)-1 hydrochloride (65% yield): $^1$H NMR (300 MHz, CD$_3$OD): δ 7.30 (m, 2H), 7.01-6.96 (m, 3H), 4.22-3.97 (AB of ABX, J$_{AB}$=10.5 Hz, 2H), 3.73 (m, 1H), 1.44 (d, J=6.9 Hz, 3H) ppm. LRMS (ESI-TOF) m/z calc. for C$_9$H$_{13}$NO [M+H$^+$] 152.1; found 152.2.

Compound 72

$^1$H NMR (300 MHz, MeOH-d$_4$) δ 1.44 (d, J=6.7 Hz, 1H), 3.71 (ddd, J=3.7, 7.1, 10.5 Hz, OH), 4.00 (dd, J=7.1, 10.3 Hz, OH), 4.20 (dd, J=3.6, 10.2 Hz, 1H), 7.00 (m, 3H), 7.30 (m, 2H).

Compound 73

$^1$H NMR (300 MHz, Methanol-d$_4$) δ 1.15-1.39 (m, 5H), 1.63-2.05 (m, 6H), 2.30 (s, 6H), 3.41 (td, J=3.7, 7.2 Hz, 1H), 3.66 (s, 1H), 3.86-4.05 (m, 1H), 6.87-7.07 (m, 2H).

Compound 74

$^1$H NMR (300 MHz, CHCl$_3$-d) δ 0.14-0.45 (m, 2H), 0.45-0.92 (m, 3H), 2.27 (s, 3H), 2.34 (dt, J=9.0, 2.7 Hz, 1H), 3.35-3.77 (m, 1H), 3.80-4.20 (m, 2H), 4.46 (dd, J=2.6, 12.1 Hz, 1H), 6.89 (t, J=7.4 Hz, 1H), 6.98 (dt, J=7.6, 1.9 Hz, 1H), 7.06 (dt, J=7.4, 1.2 Hz, 1H)

Compound 75

$^1$H NMR (300 MHz, Methanol-d$_4$) δ 2.19 (s, 3H), 2.24 (s, 3H), 4.18-4.37 (m, 2H), 4.73 (dd, J=4.2, 8.4 Hz, 1H), 6.73 (dd, J=2.8, 8.2 Hz, 1H), 6.82 (d, J=2.7 Hz, 1H), 7.03 (d, J=8.2 Hz, 1H), 7.42-7.58 (m, 5H).

Compound 76

$^1$H NMR (300 MHz, Methanol-d$_4$) δ 1.15-1.38 (m, 6H), 1.75 (d, J=10.8 Hz, 1H), 1.88 (d, J=9.7 Hz, 6H), 2.36 (s, 3H), 3.43 (td, J=3.5, 7.0 Hz, 1H), 4.01-4.22 (m, 2H), 7.04 (t, J=7.8 Hz, 1H), 7.12-7.31 (m, 2H).

Compound 77

$^1$H NMR (300 MHz, Methanol-d$_4$) δ 0.54 (qd, J=4.9, 10.2 Hz, 2H), 0.70-0.82 (m, 2H), 1.07-1.24 (m, 1H), 2.20 (s, 3H), 2.2.4 (s, 3H), 2.79 (ddd, J=3.5, 7.0, 10.4 Hz, 1H), 4.09 (dd, J=7.0, 10.3 Hz, 1H), 4.23 (dd, J=3.5, 10.3 Hz, 1H), 6.72 (dd, J=2.7, 8.2 Hz, 1H), 6.80 (d, J=2.8 Hz, 1H), 7.03 (d, J=8.2 Hz, 1H).

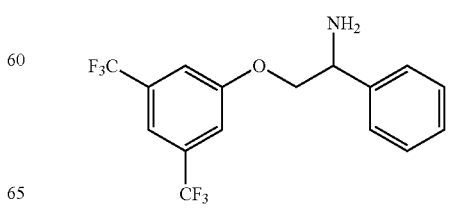

Compound 78. 2-(3,5-bis(trifluoromethyl)phenoxy)-1-phenylethan-1-amine

ESI/MS: calc. C$_{16}$H$_{13}$F$_6$NO m/z=349.1, found m/z=350.0 [M+1] $^1$H NMR (300 MHz, CHCl$_3$-d) δ 4.02 (t, J=8.7 Hz, 1H), 4.15 (dd, J=3.8, 8.7 Hz, 1H), 4.48 (dd, J=3.8, 8.6 Hz, 1H), 7.27-7.49 (m, 8H).

Compound 79

LRMS (ESI-TOF) m/z Expected [M+H]$^+$=243, Obs. [M+H]$^+$=243

Compound 80

$^1$H NMR (300 MHz, Chloroform-d) δ 2.62-2.85 (m, 3H), 3.38 (s, 3H), 3.50 (m, 3H), 4.08-4.21 (m, 3H), 7.27 (d, J=10.2 Hz, 2H), 7.32-7.50 (m, 6H).

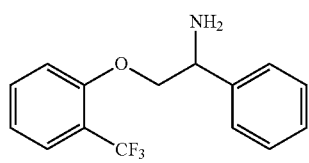

Compound 81. 1-phenyl-2-(3-(trifluoromethyl)phenoxy)ethan-1-amine

ESI/MS: calculated C$_{15}$H$_{14}$F$_3$NO m/z=281.1, found m/z=282.0 [M+1].

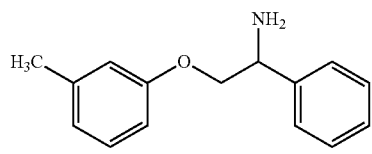 [SMILES: NC(COc1cccc(C(F)(F)F)c1)c1ccccc1]

Compound 82. 1-phenyl-2-(2-(trifluoromethyl)phenoxy)ethan-1-amine

ESI/MS: calculated C$_{15}$H$_{14}$F$_3$NO m/z=281.1, found m/z=282.0 [M+1].

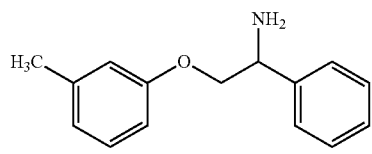 [SMILES: NC(COc1cccc(C(F)(F)F)c1)c1ccccc1]

Compound 83. 2-methyl-N-(1-phenyl-2-(m-tolyloxy)ethyl)propane-2

ESI/MS: calculated C$_{15}$H$_{17}$NO m/z=227.1, found m/z=228.0 [M+1].

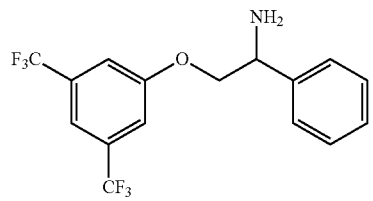 [SMILES: NC(COc1cc(C(F)(F)F)cc(C(F)(F)F)c1)c1ccccc1]

Compound 84

MS: [M+H]$^+$=288. Expected [M+H]$^+$=288

Compound 85

MS: [M+H]$^+$=220. Expected [M+H]$^+$=220

Compound 86

MS: [M+H]$^+$=166. Expected [M+H]$^+$=166

Compound 87

$^1$H NMR (300 MHz, Chloroform-d) δ 0.63-1.41 (m, 5H), 1.09 (d, J=5.1 Hz, 3H), 1.43-2.0 (m, 5H), 3.07-3.31 (m, 2H), 3.37-3.50 (m, 1H)

Compound 88

A mixture of rotamers. $^1$H NMR (300 MHz, Methanol-d$_4$) δ 2.14-2.40 (m, 3H), 4.17-4.26 (m, 2H), 4.32-4.49 (m, 1H), 7.50-7.72 (m, 6H), 7.83-8.29 (m, 2H).

Compound 89

$^1$H NMR (300 MHz, Methanol-d$_4$) δ 1.07-1.54 (m, 5H), 1.64-1.98 (m, 6H), 2.28 (s, 6H), 3.32 (s, 3H), 4.04-4.23 (m, 2H), 6.58-6.67 (m, 3H).

Compound 90

$^1$H NMR (300 MHz, Chloroform-d) δ 2.24 (s, 3H), 2.68-2.86 (m, 2H), 3.37 (s, 3H), 3.53 (td, J=1.4, 4.5, 5.0 Hz, 2H), 4.02-4.19 (m, 2H), 4.21 (dd, J=4.1, 8.3 Hz, 1H), 6.71-6.95 (m, 2H), 7.04-7.20 (m, 2H), 7.21-7.44 (m, 3H), 7.44-7.53 (m, 2H).

Compound 91

$^1$H NMR (300 MHz, Chloroform-d) δ 6.68 (s, 2H), 6.58 (s, 1H), 4.04-4.37 (m, 3H), 2.26 (s, 6H), 0.52 (br. s., 4H), 0.16 (br. s., 1H)

Compound 92

$^1$H NMR (300 MHz, ChCl$_3$-d) δ 2.28 (s, 6H), 2.61-2.87 (m, 2H), 3.52-3.74 (m, 2H), 3.94-4.10 (m, 2H), 4.10-4.19 (m, 1H), 6.50-6.64 (m, 2H), 7.22-7.46 (m, 6H).

Compound 93

ESI/MS: MW calculated for $C_{18}H_{17}F_6NO_2$: 393.1 Observed: 394.0 [M+H]$^+$

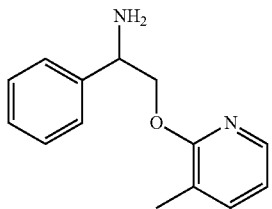 [SMILES: Cc1cccnc1OCC(N)c1ccccc1]

2-(3-methylpyridin-2-yloxy)-1-phenylethanamine, KJO-VIII-068

$^1$H NMR (CDCl$_3$): 2.19 (s, 3H), 2.74 (bs, 2H), 4.02 (dd, J=7.7 Hz and 13.7 Hz, 1H), 4.41 (dd, J=2.7 Hz and 13.7 Hz, 1H), 5.17 (dd, J=2.2 Hz and 7.7 Hz, 1H), 6.05 (t, J=6.6 Hz, 1H), 6.94 (d, J=6.6 Hz, 1H), 7.23 (d, J=6.6 Hz, 1H), 7.29 (t, J=7.1 Hz, 1H), 7.35 (t, J=7.7 Hz, 2H), 7.40 (d, J=7.1 Hz, 2H).

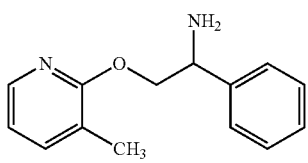 [SMILES: Cc1cccnc1OCC(N)c1ccccc1]

Compound 94. 2-((3-methylpyridin-2-yl)oxy)-1-phenylethan-1-amine

ESI/MS: calculated $C_{14}H_{14}N_2O_2$ m/z=228.1, found m/z=229.0 [M+1] $^1$H NMR (300 MHz, Chloroform-d) δ 2.10 (s, 3H), 4.19 (d, J=6.6 Hz, 2H), 4.65 (t, J=6.5 Hz, 1H), 5.95 (t, J=6.8 Hz, 1H), 6.92 (d, J=6.8 Hz, 1H), 7.16 (d, J=6.9 Hz, 1H), 7.24-7.38 (m, 3H), 7.39-7.50 (m, 2H).

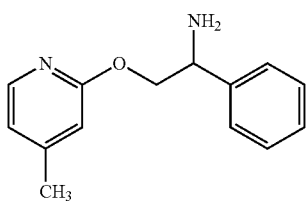

Compound 95. 2-((4-methylpyridin-2-yl)oxy)-1-phenylethan-1-amine

ESI/MS: calculated $C_{14}H_{16}N_2O$ m/z=228.1, found m/z=229.0 [M+1].

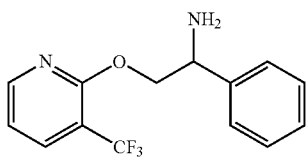 [SMILES: NC(COc1ncccc1C(F)(F)F)c1ccccc1]

Compound 96. 1-phenyl-2-((3-(trifluoromethyl)pyridin-2-yl)oxy)ethan-1-amine

ESI/MS: calculated $C_{14}H_{13}F_3N_2O$ m/z=282.1, found m/z=283.0 [M+1].

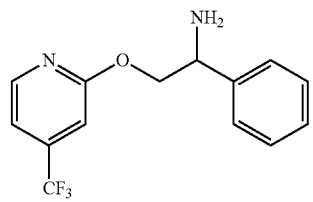 [SMILES: NC(COc1cc(C(F)(F)F)ccn1)c1ccccc1]

Compound 97. 1-phenyl-2-((4-(trifluoromethyl)pyridin-2-yl)oxy)ethan-1-amine

ESI/MS: calculated $C_{14}H_{13}F_3N_2O$ m/z=282.1, found m/z=283.0 [M+1].

Compound 98

$^1$H NMR (300 MHz, Methanol-d$_4$) δ 2.11 (s, 6H), 2.58 (m, 8H), 3.40-3.63 (m, 6H), 3.78 (s, 1H), 6.46-6.56 (m, 3H), 7.27-7.41 (m 3H), 7.46-7.57 (m, 2H).

Compound 99

$^1$H NMR (300 MHz, Methanol-d$_4$) δ 3.49 (d, J=6.2 Hz, 1H), 3.71 (s, 10H), 3.95 (m, 8H), 4.61-4.84 (m, 6H), 7.50-7.54 (m, 4H), 7.65-7.73 (m, 4H).

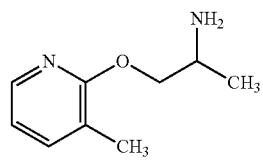

Compound 100

1-(-3-Methyl-pyridin-2-yloxy)propan-2-amine was made (31% yield) as a pale yellow solid: Rf=0.44 (1% NH$_4$H$_{(aq)}$/20% MeOH/79% CH2Cl2): $^1$H NMR (300 MHz, CD$_3$OD) δ 7.45 (m, 1H, HAr), 7.39 (m, 1H, HAr), 6.30 (t, J=6.9 Hz, 1H, HAr), 4.06-3.89 (AB of ABX, J$_{AB}$=12.8 Hz, 2H, CH$_2$), 3.42 (m, 1H, CH), 1.17 (d, J=6.6 Hz, 1H, CH$_3$) ppm. ESI/MS for $C_9H_{14}N_2O$: calc. [M+H]$^+$=167.1, found m/z=167.1.

Compound 105

$^1$H NMR (300 MHz, Chloroform-d) δ 2.62-2.83 (m, 2H), 3.37 (s, 3H), 3.44-3.56 (m, 2H), 4.07 (t, J=8.6 Hz, 1H), 4.11-4.26 (m, 2H), 6.90 (d, J=8.3 Hz, 1H), 6.94-7.05 (m, 1H), 7.25-7.46 (m, 3H), 7.45 (tt, J=1.4, 7.4 Hz, 3H), 7.51-7.61 (m, 1H).

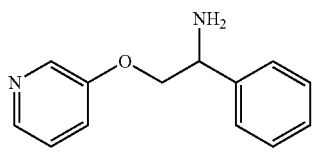 [SMILES: NC(COc1cccnc1)c1ccccc1]

Compound 110

¹H NMR (499 MHz, CD₃OD) δ 8.32-8.41 (m, 1H), 8.25-8.32 (m, 1H), 7.44-7.69 (m, 4H), 7.38 (t, J=7.68 Hz, 2H), 7.28-7.35 (m, 1H), 5.12 (dd, J=3.84, 7.68 Hz, 1H), 4.72-4.79 (m, 2H), 4.29-4.47 (m, 2H), 3.57-3.78 (m, 2H), 3.39 (s, 3H). Calculated m/z for $C_{16}H_{20}N_2O_2$: 272.15, Observed: 273.2 [M+H]⁺, 295.3 [M+Na]⁺

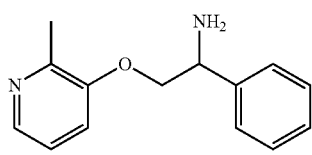 [SMILES: Cc1ncccc1OCC(N)c1ccccc1]

Compound 111

$R_f$=0.44 (1:20 MeOH/DCM), purity 98%+. ¹H NMR (300 MHz, Methanol-d₄) δ 8.18 (d, J=4.8 Hz, 1H), 7.55-7.18 (m, 7H), 4.57-4.40 (m, 2H), 2.43 (s, 3H). Calculated m/z for $C_{14}H_{16}N_2O$ m/z: 228.1, found m/z=229.00 [M+H]⁺.

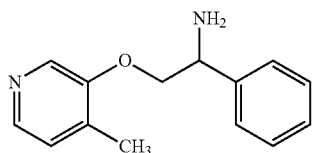

Compound 112

Rf=0.45 (1:20 MeOH/DCM), purity 97%+. ¹H NMR (300 MHz, Methanol-d₄) δ 8.47-8.26 (m, 2H), 7.85-7.30 (m, 6H), 5.11 (s, 1H), 4.35 (d, J=5.2 Hz, 2H), 2.45 (s, 3H). Calculated m/z for $C_{14}H_{16}N_2O$ m/z: 228.1, found m/z=229.00 [M+H]⁺.

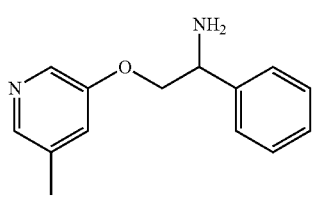

Compound 113

$R_f$=0.43 (1:20 MeOH/DCM), purity 95%+. ¹H NMR (300 MHz, DMSO-d₆) δ 8.98 (s, 3H), 8.10 (d, J=10.1 Hz, 2H), 7.82-7.57 (m, 2H), 7.50-7.39 (m, 4H), 4.77 (s, 1H), 4.52-4.39 (m, 2H), 2.35 (s, 3H). Calculated m/z for $C_{14}H_{16}N_2O$ m/z: 228.1, found m/z=229.00 [M+H]⁺.

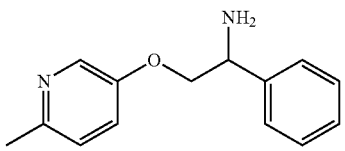

Compound 114

$R_f$=0.43 (1:20 MeOH/DCM), purity 97%+. ¹H NMR (300 MHz, DMSO-d₆) δ 8.90 (s, 3H), 8.50 (s, 1H), 7.87 (d, J=8.9 Hz, 1H), 7.66 (m, 3H), 7.45 (m, J=6.9 Hz, 3H), 4.81 (s, 1H), 4.52 (m, J=5.3 Hz, 2H), 2.48 (s, 3H). Calculated m/z for $C_{14}H_{16}N_2O$ m/z: 228.1, found m/z=229.00 [M+H]⁺.

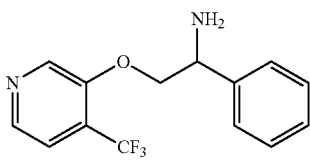 [SMILES: Cc1ccncc1OCC(N)c1ccccc1]

Compound 115

$R_f$=0.45 (1:20 MeOH/DCM), purity 95%+. ¹H NMR (300 MHz, Methanol-d₄) δ 8.37 (s, 1H), 7.91-7.21 (m, 7H), 4.52-4.37 (m, 2H). Calculated m/z for $C_{14}H_{13}F_3N_2O$ m/z: 282.1, found m/z=283.00 [M+H]⁺.

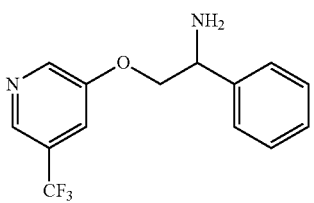 [SMILES: NC(COc1cncc(C(F)(F)F)c1)c1ccccc1]

Compound 116

$R_f$=0.46 (1:20 MeOH/DCM), purity 95%+. ¹H NMR (300 MHz, Methanol-d₄) δ 8.12-7.02 (m, 8H), 4.70-4.59 (m, 1H), 4.45-4.31 (m, 2H). Calculated m/z for $C_{14}H_{13}F_3N_2a$ m/z: 282.1, found m/z=283.0 [M+H]⁺.

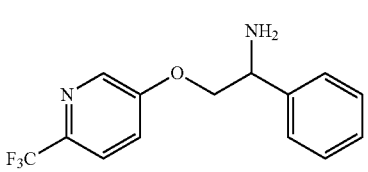 [SMILES: NC(COc1ccc(C(F)(F)F)nc1)c1ccccc1]

Compound 117

$R_f$=0.46 (1:20 MeOH/DCM), purity 95%+. Entry #10, (Notebook: MEJ-I-077) ¹H NMR (300 MHz, DMSO-d₆) δ 8.92 (s, 3H), 8.31 (s, 1H), 7.92 (d, J=8.6 Hz, 1H), 7.70-7.54 (m, 3H), 7.45 (m, 3H), 4.80 (s, 1H), 4.51 (m, J=5.1 Hz, 2H), 2.46 (s, 3H). Calculated m/z for $C_{14}H_{13}F_3N_2O$ m/z: 282.1, found m/z=283.0 [M+H]⁺.

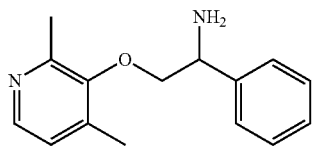 [SMILES: Cc1ccnc(C)c1OCC(N)c1ccccc1]

Compound 118

R$_f$=0.45 (1:20 MeOH/DCM), purity 98%+. $^1$H NMR (300 MHz, Methanol-d$_4$) δ 7.98 (d, J=5.0 Hz, 1H), 7.50-7.42 (m, 2H), 7.35 (dt, J=15.0, 7.0 Hz, 3H), 7.07 (d, J=5.0 Hz, 1H), 4.38 (t, J=5.8 Hz, 1H), 3.94 (dd, J=5.8, 2.9 Hz, 2H), 2.35 (s, 3H), 2.21 (s, 3H). Calculated m/z for C$_{15}$H$_{18}$N$_2$O m/z: 242.1, found m/z=243.0 [M+H]$^+$.

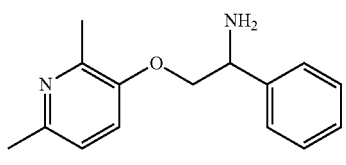

Compound 119

R$_f$=0.45 (1:20 MeOH/DCM), purity 98%+. $^1$H NMR (300 MHz, Methanol-d$_4$) δ 7.55-7.11 (m, 7H), 4.68 (s, 1H), 4.52-4.37 (m, 2H), 2.62 (s, 3H), 2.41 (s, 3H). Calculated m/z for C$_{15}$H$_{18}$N$_2$O m/z: 242.1, found m/z=243.00 [M+H]$^+$.

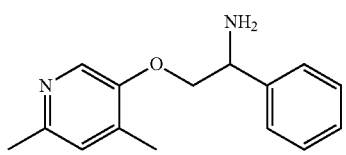 [SMILES: Cc1cc(C)c(OCC(N)c2ccccc2)cn1]

Compound 120

R$_f$=0.46 (1:20 MeOH/DCM), purity 95%+. $^1$H NMR (300 MHz, DMSO-d$_6$) δ 9.12 (s, 3H), 8.48 (s, 1H), 7.95-7.55 (m, 3H), 7.44 (m, 3H), 4.81 (s, 1H), 4.62-4.37 (m, 2H), 2.64 (s, 3H), 2.45 (s, 3H). Calculated m/z for C$_{15}$H$_{18}$N$_2$O m/z: 242.1, found m/z=243.00 [M+H]$^+$.

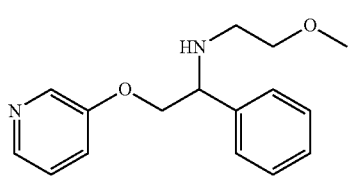 [SMILES: COCCNC(COc1cccnc1)c1ccccc1]

Compound 121

$^1$H NMR (499 MHz, CD$_3$OD) δ 8.32-8.41 (m, 1H), 8.25-8.32 (m, 1H), 7.44-7.69 (m, 4H), 7.38 (t, J=7.68 Hz, 2H), 7.28-7.35 (m, 3H), 5.12 (dd, J=3.84, 7.68 Hz, 1H), 4.72-4.79 (m, 2H), 4.29-4.47 (m, 2H), 3.57-3.78 (m, 2H), 3.39 (s, 3H); Calculated for C$_{16}$H$_{20}$N$_2$O$_2$: 272.15 Observed: 273.2 [M+H]$^+$, 295.3 [M+Na]$^+$

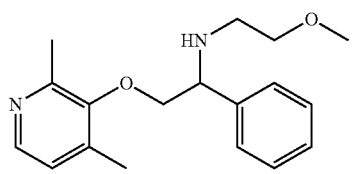 [SMILES: COCCNC(COc1c(C)ccnc1C)c1ccccc1]

Compound 122

R$_f$=0.49 (1:20 MeOH/DCM), purity 98%+. $^1$H NMR (300 MHz, Methanol-d$_4$) δ 8.50-7.09 (bm, 7H), 5.10 (s, 1H), 4.18 (s, 2H), 3.81-3.68 (m, 2H), 3.51 (s, 2H), 3.29 (s, 3H), 2.61 (s, 3H), 2.43 (s, 3H). Calculated m/z for C$_{18}$H$_{24}$N$_2$O$_2$ m/z: 300.18, found m/z=301.0 [M+H]$^+$.

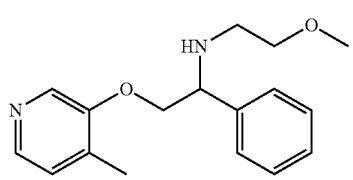 [SMILES: COCCNC(COc1cnccc1C)c1ccccc1]

Compound 123

R$_f$=0.48 (1:20 MeOH/DCM), purity 98%+. $^1$H NMR (300 MHz, Methanol-d$_4$) δ 8.44 (s, 1H), 8.29 (s, 1H), 7.80 (s, 1H), 7.39 (m, 5H), 5.12 (s, 1H), 4.33 (d, J=5.2 Hz, 2H), 3.61 (m, 4H), 3.38 (s, 3H), 2.48 (s, 3H). Calculated m/z for C$_{17}$H$_{22}$N$_2$O$_2$ m/z: 286.17, found m/z=287.0 [M+H]$^+$.

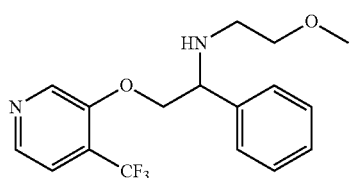

Compound 124

R$_f$=0.46 (1:20 MeOH/DCM), purity 95%+. $^1$H NMR (300 MHz, Methanol-d$_4$) δ 8.37 (s, 1H), 7.91-7.21 (m, 7H), 4.52-4.37 (m, 2H), 4.15-4.01 (m, 2H), 3.56-3.41 (m, 2H), 3.28 (s, 3H). Calculated m/z for C$_{17}$H$_{19}$F$_3$N$_2$O$_2$ m/z: 340.14, found m/z=341.0 [M+H]$^+$.

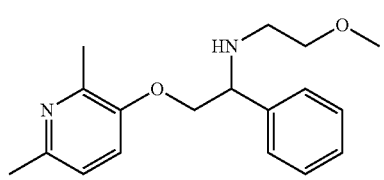

Compound 125

R$_f$=0.48 (1:20 MeOH/DCM), purity 97%+. $^1$H NMR (300 MHz, Methanol-d$_4$) δ 7.61-7.05 (m, 7H), 4.71-4.60 (m, 1H), 4.54-4.39 (m, 2H), 3.91-3.52 (m, 4H), 3.27 (s, 3H), 2.62 (s, 3H), 2.41 (s, 3H). Calculated m/z for $C_{18}H_{24}N_2O_2$ m/z: 300.18, found m/z=301.0 $[M+H]^+$.

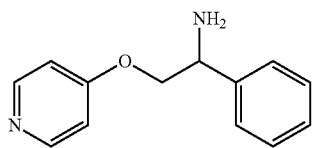

Compound 126

$^1$H NMR (300 MHz, CD$_3$OD) δ 4.25 (d, J=10.3 Hz, 1H), 4.32 (d, J=10.3 Hz, 1H), 6.60-6.70 (m, 4H), 7.41-7.61 (m, 5H). ESI/MS calculated for $C_{13}H_{14}N_2O$ m/z: 214.1, found m/z=215.0 $[M+H]^+$.

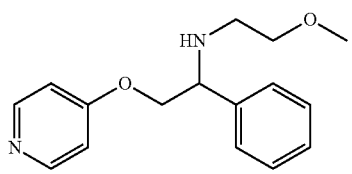 [SMILES: COCCNC(COc1ccncc1)c1ccccc1]

Compound 127

$^1$H NMR (300 MHz, CD$_3$OD) δ 7.41-7.61 (m, 5H), 6.60-6.70 (m, 4H), 4.70 (br. s., 1H), 4.48 (br. s., 1H), 4.32 (br. s., 1H), 3.72-3.45 (m. 2H), 3.30-3.42 (m, 2H), 3.28 (s, 3H).

ESI/MS calculated for $C_{16}H_{20}N_2O_2$ m/z: 272.2, found m/z=273.1 $[M+H]^+$.

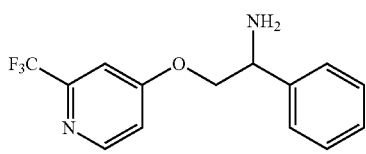 [SMILES: NC(COc1ccnc(C(F)(F)F)c1)c1ccccc1]

Compound 128

$R_f$=0.47 (1:20 MeOH/DCM), purity 95%+. $^1$H NMR (300 MHz, Methanol-d$_4$) δ 8.52 (d, J=5.1 Hz, 1H), 7.63-7.22 (m, 6H), 6.75 (s, 1H), 4.71-4.63 (m, 1H), 4.49-4.34 (m, 2H). Calculated m/z for $C_{14}H_{13}F_3N_2O$ m/z: 282.1, found m/z=283.00 [M+H].

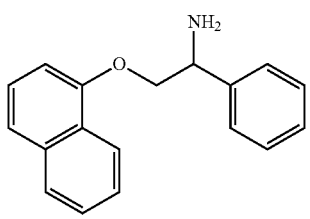 [SMILES: NC(COc1cccc2ccccc12)c1ccccc1]

Compound 129

$R_f$=0.50 (1:20 MeOH/DCM), purity 97%+. $^1$H NMR (300 MHz, DMSO-d$_6$) δ 8.80 (s, 3H), 8.44 (d, J=9.6 Hz, 1H), 7.96-7.76 (m, 1H), 7.49 (m, 9H), 6.99 (d, J=7.5 Hz, 1H), 4.90 (m, 1H), 4.46 (d, J=5.7 Hz, 2H). Calculated m/z for $C_{18}H_{17}NO$ m/z: 263.1, found m/z=264.1 [M+H].

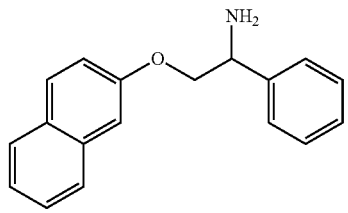 [SMILES: NC(COc1ccc2ccccc2c1)c1ccccc1]

Compound 130

$R_f$=0.45 (1:20 MeOH/DCM), purity 97%+. $^1$H NMR (300 MHz, Methanol-d$_4$) δ 8.81-8.35 (m, 3H), 7.82 (dd, J=16.8, 10.6 Hz, 3H), 7.63 (d, J=6.5 Hz, 4H), 7.56-7.09 (m, 5H), 4.81 (s, 1H), 4.40 (s, 2H). Calculated m/z for $C_{18}H_{17}NO$ m/z: 263.1, found m/z=264.1 $[M+H]^+$.

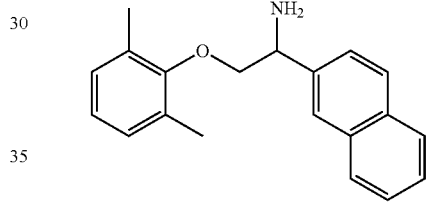

Compound 131

$R_f$=0.52 (1:20 MeOH/DCM), purity 97%+. $^1$H NMR (300 MHz, DMSO-d$_6$) δ 8.95 (s, 3H), 8.15 (s, 1H), 7.97 (m, 3H), 7.77 (d, J=8.5 Hz, 1H), 7.57 (dd, J=5.7, 3.8 Hz, 2H), 7.01-6.87 (m, 3H), 4.90 (s, 1H), 4.38-4.00 (m, 2H), 2.10 (s, 6H). Calculated m/z for $C_{20}H_{21}NO$ m/z: 291.16, found m/z=292.10 $[M+H]^+$.

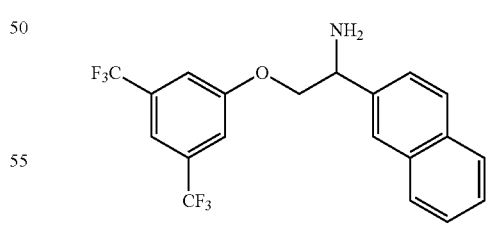

Compound 132

$R_f$=0.60 (1:20 MeOH/DCM), purity 97%+. $^1$H NMR (300 MHz, DMSO-d$_6$) δ 8.87-8.42 (m, 3H), 8.12 (s, 1H), 8.09-7.85 (m, 4H), 7.71 (s, 4H), 7.58 (d, J=9.4 Hz, 1H), 4.94 (s, 1H), 4.61 (s, 2H). Calculated m/z for $C_{20}H_{15}F_6NO$ m/z: 399.1, found m/z=400.1 $[M+H]^+$.

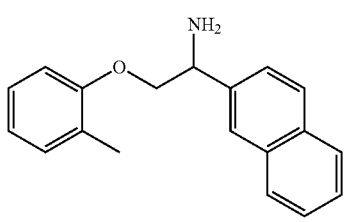

Compound 133

R$_f$=0.48 (1:20 MeOH/DCM), purity 97%+. $^1$H NMR (300 MHz, DMSO-d$_6$) δ 8.83 (s, 3H), 8.14 (s, 1H), 8.06-7.85 (m, 3H), 7.75 (d, J=8.6 Hz, 1H), 7.57 (dd, J=6.2, 3.3 Hz, 2H), 7.11 (d, J=7.4 Hz, 2H), 6.95 (d, J=7.5 Hz, 1H), 6.85 (t, J=7.0 Hz, 1H), 4.92 (s, 1H), 4.39 (d, J=5.5 Hz, 2H), 2.17 (s, 3H). Calculated m/z for C$_{19}$H$_{19}$NO m/z: 277.15, found m/z=278.1 [M+H]$^+$.

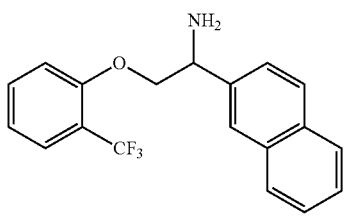

Compound 134

R$_f$=0.5 (1:20 MeOH/DCM), purity 97%+. $^1$H NMR (300 MHz, DMSO-d$_6$) δ 8.77 (s, 3H), 8.10 (s, 1H), 8.04-7.85 (m, 3H), 7.71 (d, J=8.7 Hz, 1H), 7.68-7.48 (m, 3H), 7.39-7.28 (m, 2H), 7.13 (t, J=7.4 Hz, 1H), 4.87 (s, 1H), 4.58 (dd, J=9.9, 5.9 Hz, 2H). Calculated m/z for C$_{19}$H$_{16}$F$_3$NO m/z: 331.12, found m/z=332.1 [M+H]$^+$.

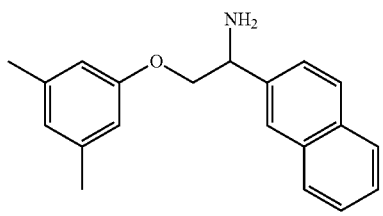 [SMILES: Cc1cc(C)cc(OCC(N)c2ccc3ccccc3c2)c1]

Compound 135

R$_f$=0.50 (1:20 MeOH/DCM), purity 97%+. $^1$H NMR (300 MHz, DMSO-d$_6$) δ 8.89 (s, 3H), 8.13 (s, 1H), 8.08-7.85 (m, 3H), 7.75 (dd, J=8.5, 1.7 Hz, 1H), 7.57 (dd, J=5.6, 3.8 Hz, 2H), 6.61 (d, J=5.0 Hz, 3H), 4.85 (t, J=6.0 Hz, 1H), 4.51-4.18 (m, 2H), 2.22 (s, 6H). Calculated m/z for C$_{20}$H$_{21}$NO m/z: 291.16, found m/z=292.10 [M+H]$^+$.

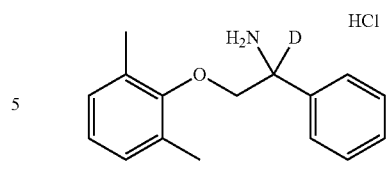

Compound 136

R$_f$=0.57 (9:1 CH$_2$Cl$_2$:CH$_3$OH) $^1$H NMR (499 MHz, methanol-d$_4$) δ 7.57 (d, 2H), 7.54-7.43 (m, 3H), 7.07-6.97 (m, 2H), 6.97-6.89 (m, 1H), 4.19-4.11 (d, 1H, J=10 Hz), 4.08 (d, 1H, J=10 Hz), 2.20 (s, 6H); m/z calculated for C$_{16}$H$_{18}$DNO: 242.15. Observed for [M+H]$^+$: 243.4.

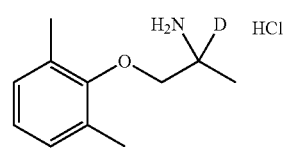

Compound 137

R$_f$=0.52 (9:1 CH$_2$Cl$_2$:CH$_3$OH); $^1$H NMR (499 MHz, methanol-d$_4$) δ 6.98-7.11 (m, 2H), 6.89-6.99 (m, 1H), 3.86-3.96 (m, 1H), 3.77-3.86 (m, 1H), 2.30 (s, 6H), 1.44 (s, 3H); m/z calculated for C$_{11}$H$_{16}$DNO: 180.14. Observed for [M+H]$^+$: 181.2.

Example 4. Preparation of Enantiomers of Mexiletine

Enantiomers of Mexiletine analogs (Scheme 1 and 2) were prepared by NaBH$_4$ reduction of the starting ketone A to give the racemic alcohol B. B and N,N'-diisopropyl-carbodiimide were combined (catalyzed by CuCl), heated with (R)-mandelic acid in toluene at 150° C. to afford S—C and R—C, that were separated via chromatography. Each diastereomer was hydrolyzed with NaOH$_{aq}$ (MeOH:THF), subjected to Mitsunobu reaction conditions in the presence of phthalimide, and treated with excess hydrazine. Each amine in ether was treated with 4M HCl in dioxane at RT to give HCl salts of the enantiomers (R)-D and (S)-D).

SCHEME 1

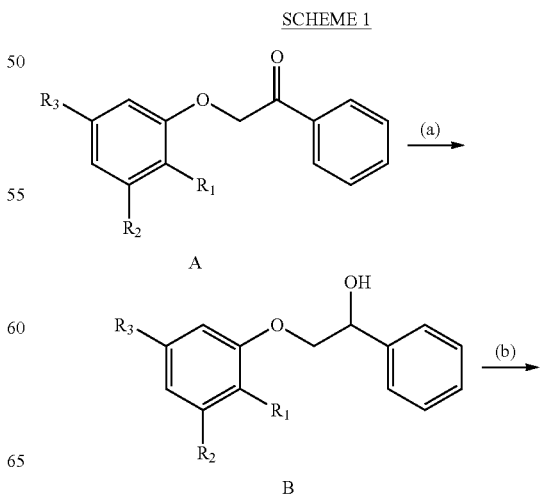

TABLE 1

Substituents for Mexiletine enantiomers in Schemes 1 and 2.

| | $R_1$ | $R_2$ | $R_3$ |
|---|---|---|---|
| Da | H | $CF_3$ | $CF_3$ |
| Db | H | $CH_3$ | $CH_3$ |
| Dc | $CH_3$ | H | H |
| Dd | $CF_3$ | H | H |

Ketone A was treated with chiral t-bultylsulfinamide catalyzed by $Ti(OEt)_4$ followed by $NaBH_4$ reduction led to a mixture of diastereomeric sulfinamides separated via chromatography. Treatment of each sulfinamide with HCl in dioxane followed by treatment with $Et_2O$ gave the individual enantiomers (S)-D and (R)-D.

SCHEME 2*

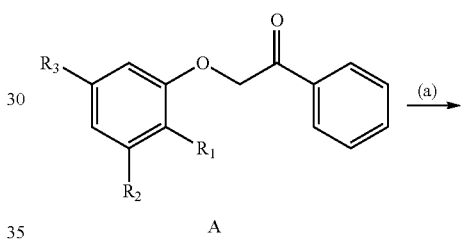

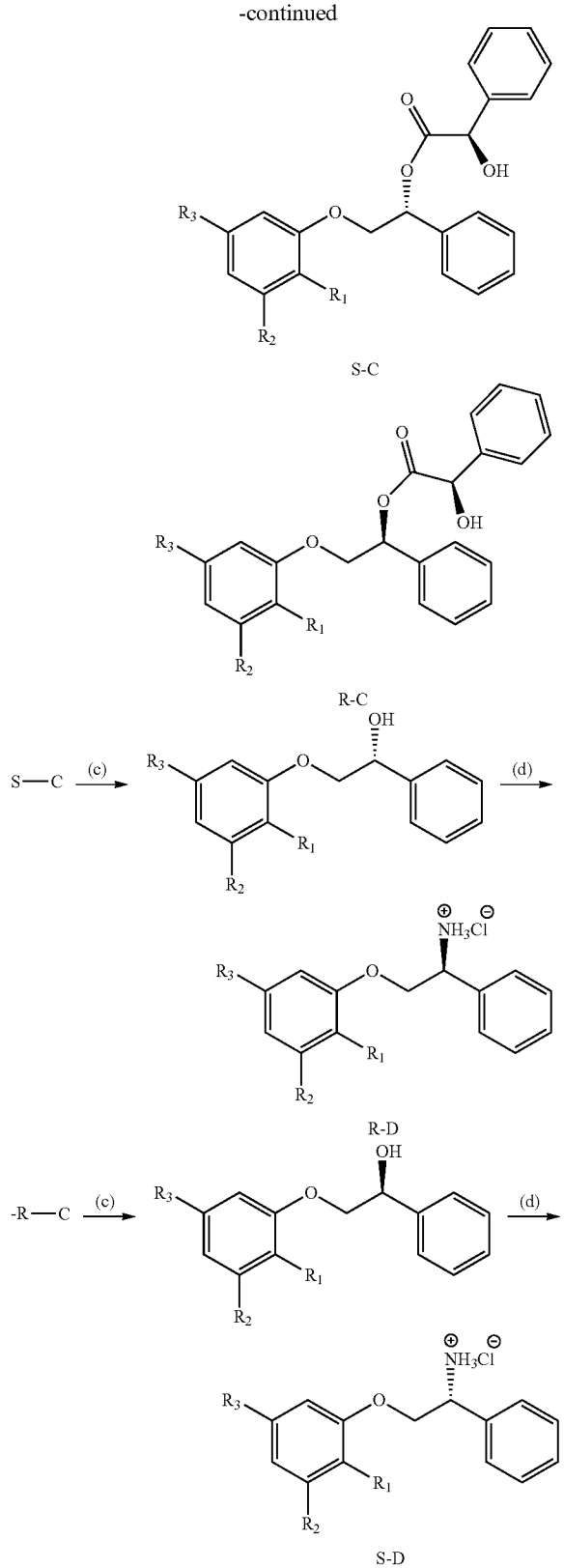

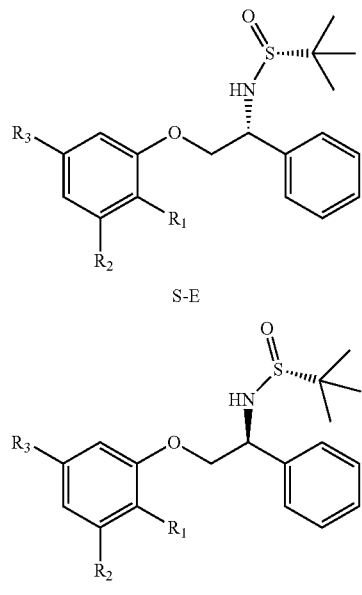

* (a) $NaBH_4$, MeOH, RT (b) (i) Diisopropycarbodiimide, CuCl, 100° C., 5 min uwave. (ii) (R)-Mandelic acid, toluene, 150° C., 5 min uwave. (c) (R)-Mandelic acid, HBTU, DMF, RT. (c) NaOH, $H_2O:CH_3OH:THF$, RT. (d) (i) Phthalimide, triphenylphosphine, diisopropoylazodicarboxylate, THF, RT; (ii) Hydrazine hydrate, EtOH, 75° C.; (iii) HCl in dioxane, ether, RT.

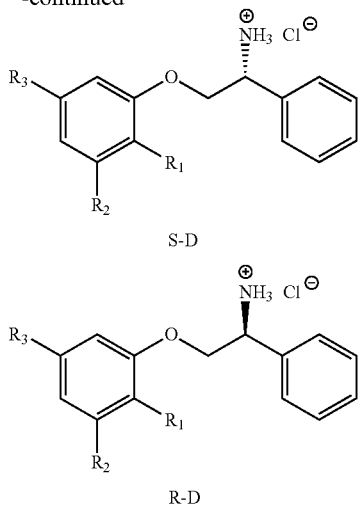

*(a) (i) (R)-2-methylpropane-2-sulfinamide, Ti(OEt)4, 90° C. (uwave), 1 h,
(ii) NaBH₄, CuSO₄, THF, RT
(b) HCl in dioxane, Et₂O, RT.

Chiral Amine (S)-Da.

1H NMR (300 MHz, Chloroform-d) δ 4.52-4.63 (m, 1H), 5.29 (t, J=9.6 Hz, 1H), 5.80 (dd, J=5.3, 10.1 Hz, 1H), 7.24-7.26 (m 4H), 7.26-7.31 (s, 2H), 7.31-7.49 (m, 3H), 7.58 (d, J=6.6 Hz, 1H), 7.68-7.79 (m, 1H), 7.78-7.89 (m, 1H). ESI MS: Calculated m/z for $C_{16}H_{13}F_6NO$: 349.1 Observed: 350.2 $[M+H]^+$. 1H NMR of the HCl salt (300 MHz, MeOH-d₄) δ 4.44-4.62 (m, 2H), 4.78-4.84 (m, 1H), 7.30-7.95 (m, 8H). $[\alpha]_{546}^{20}=-17°$ (c=0.08; CD3OD).

Chiral Amine (R)-Da.

1H NMR (300 MHz, MeOH-d₄) δ 4.44-4.62 (m, 2H), 4.78-4.84 (m, 1H), 7.30-7.95 (m, 8H). ESI MS: Calculated m/z for $C_{16}H_{13}F_6NO$: 349.1 Observed: 350.2 $[M+H]^+$ $[\alpha]_{546}^{20}=+19°$ (c=0.08; CD3OD).

Chiral Amine (R)-db.

$^1$H NMR (300 MHz, MeOH-d₄) δ 2.27 (d, J=0.7 Hz, 6H), 4.18-4.38 (m, 2H), 4.73 (dd, J=4.1, 8.4 Hz, 1H), 6.64 (s, 3H), 7.42-7.58 (m, 4H). Calculated m/z for $C_{16}H_{19}NO$: 241.1 Observed: 242.1 $[M+H]^+$. $[\alpha]_{546}^{20}=-30°$ (c=0.1; CD₃OD).

Chiral Amine (S)-db.

$^1$H NMR (300 MHz, MeOH-d₄) δ 2.27 (d, J=0.7 Hz, 6H), 4.18-4.38 (m, 2H), 4.73 (dd, J=4.1, 8.4 Hz, 1H), 6.64 (s, 3H), 7.42-7.58 (m, 4H). Calculated m/z for $C_{16}H_{19}NO$: 241.1 Observed: 242.1 $[M+H]^+$. $[\alpha]_{546}^{20}=+32.3°$ (c=0.1; CD₃OD).

Chiral Amine (R)-Dc.

$^1$H NMR (300 MHz, MeOH-d₄) δ 2.27 (s, 3H), 3.44 (s, 2H), 4.26-4.40 (m, 1H), 6.83-6.97 (m, 1H), 7.08-7.19 (m, 1H), 7.42-7.60 (m, 2H). Calculated m/z for $C_{15}H_{17}NO$: 227.1 Observed: 228.1 $[M+H]^+$. $[\alpha]_{589}^{20}=-12°$ (c=0.1; CD₃OD).

Chiral Amine (S)-Dc.

$^1$H NMR (300 MHz, MeOH-d₄) δ 2.27 (s, 3H), 3.44 (s, 2H), 4.26-4.40 (m, 1H), 6.83-6.97 (m, 1H), 7.08-7.19 (m, 1H), 7.42-7.60 (m, 2H). Calculated m/z for $C_{15}H_{17}NO$: 227.1 Observed: 228.1 $[M+H]^+$. $[\alpha]_{589}^{20}=+15°$ (c=0.1; CD₃OD).

Chiral Amine (S)-Dd.

$^1$H NMR (300 MHz, MeOH-d₄) δ 4.43-4.53 (m, 2H), 4.77-4.85 (m, 1H), 7.09-7.31 (m, 2H) 7.43-7.53 (m, 1H), 7.48-7.67 (m, 1H). Calculated m/z for $C_{16}H_{19}NO$: 281.1 Observed: 282.1 $[M+H]^+$. $[\alpha]_{589}^{20}=+36°$ (c=0.15; CD₃OD).

Chiral Amine (R)-Dd.

$^1$H NMR (300 MHz, MeOH-d₄) δ 4.43-4.53 (m, 2H), 4.77-4.85 (m. 1H), 7.09-7.31 (m, 2H) 7.43-7.53 (m, 1H), 7.48-7.67 (m, 1H). Calculated m/z for $C_{16}H_{19}NO$: 281.1 Observed: 282.2 $[M+H]^+$. $[\alpha]_{589}^{20}=-31°$ (c=0.15; CD3OD). The enantiomers (i.e., (R)- and (S)-Da-Dd) were examined side by side for pharmacological response in cardiomyocytes derived from IPSCs from an LQT3 patient. For Da-Dd, it was observed that compared to the (R)-enantiomer, the (S)-enantiomer generally possessed much greater action potential shortening. This stereoselective result showed fundamental pharmacological interaction with the cellular target in the cells from the patient cohort. The interaction with the cells possesses significant stereoselectivity. However, this observation is surprising and unexpected because the clinically used material (i.e., (R)-Mexilitene) possesses the opposite apparent (and modest) stereoselectivity as observed for the more pharmacologically potent analogs described in this Example (i.e., Da to Dd). Further, (R)- and (S)-Mexilitene itself does not show significant stereoselectivity for shortening of the action potential in IPSCs-derived cardiomyocytes from an LQT3 patient (i.e., (R)-Mexilitene ratio is 1.3 and (S)-Mexilitene is 1.25 and racemic Mexilitene ratio is 1.3, see Table 3, Example 1, data for entries 1, 2a and 2b). This result may be due to the differences in the pharmacological preparations used in the experiments.

Example 5: Separation of Enantiomers of Mexiletine

Reverse phase HPLC analysis. RPHPLC analysis of N-tert-butanesulfinyl amine derivatives of Mexiletine and analogs (Example 4, Scheme 2) was done on a Hitachi HPLC using a Phenomenex Luna C18 column (5 µm, 150×4.6 mm) using gradient elution at a flow rate of 1.0 mL/min. Compounds were eluted using a mobile phase gradient of 60/40 water/acetonitrile with 0.05% TFA to 20/80 water/acetonitrile with 0.05% TFA. UV detection was at 254 nm.

Chiral Phase HPLC Analysis.

Mexiletine enantiomers and enantiomers of analogs were analyzed by HPLC on a Hitachi HPLC using a Phenomenex Lux Cellulose-1 column (5 m, 150×4.6 mm) with isocratic elution using a mobile phase of 75/20/5 hexanes/isopropanol/acetonitrile with 0.01% perchloric acid (70% aqueous solution) at a flow rate of 0.75 mL/min. UV detection was at 220 nm. On the basis of chiral phase HPLC, purity of Mexiletine enantiomers was observed to be >95%. Purity of synthetic Mexiletine analog enantiomers (RPHPLC) was observed to be >95%.

Example 6: Synthesis of Deuterated Compounds for Improved Metabolic Stability

Deuterated compounds 104a-d were synthesized according to Scheme 1 (below). Ketones 101a-101d were treated with NaBD₄ (>99% deuterium) in EtOH at RT to afford deutero alcohols 102a-102d that were treated with phthalimide, triphenylphosphine and diisopropyl azodicarboxylate in THF (72 h) to provide 103a-103d. Treatment of 103a-103d with hydrazine hydrate in refluxing EtOH (20 h) yielded the free base form of the amines that were converted to their corresponding HCl salts 104a-104d by treatment with HCl in dioxane/ether (1 h, RT).

Scheme 1

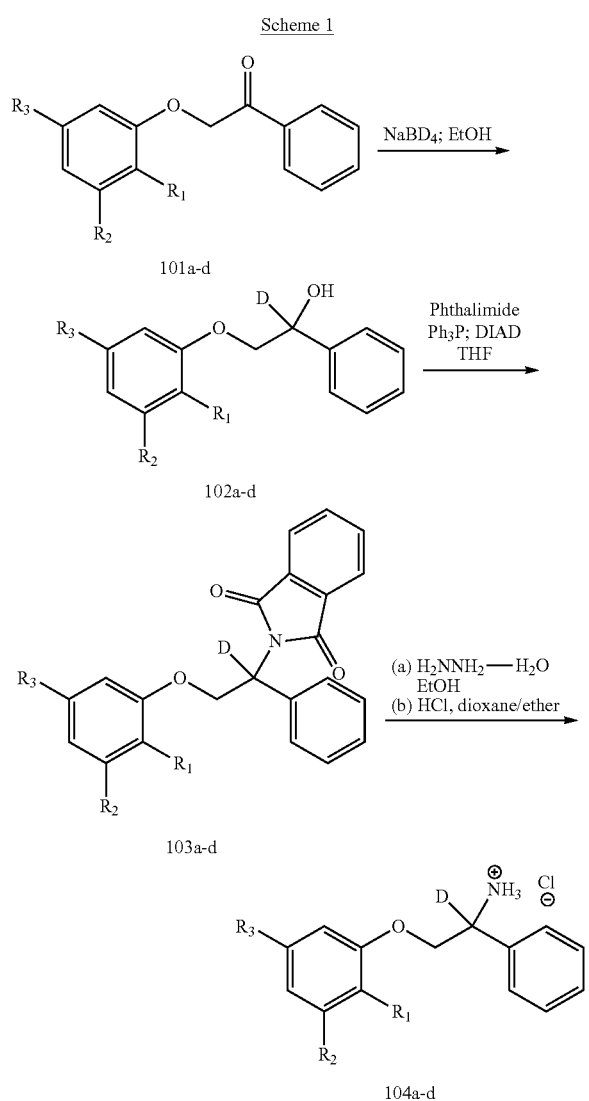

TABLE 1
Deuterated Analogs of Mexiletine Analogs

| Compd | R₁ | R₂ | R₃ |
|---|---|---|---|
| 104 a | H | CF₃ | CF₃ |
| 104 b | H | CH₃ | CH₃ |

TABLE 1-continued
Deuterated Analogs of Mexiletine Analogs

| Compd | R₁ | R₂ | R₃ |
|---|---|---|---|
| 104 c | CH₃ | H | H |
| 104 d | CF₃ | H | H |

Compound 104a ($R_1$=H; $R_2$=$CF_3$; $R_3$=$CF_3$): $^1$H NMR (300 MHz, MeOH-$d_4$) δ 4.48 (d, J=10.4 Hz, 1H), 4.55 (d, J=10.4 Hz, 1H), 7.42-7.59 (m, 4H), 7.61-7.65 (m, 4H). ESI/MS calcd. for $C_{16}H_{12}DF_6NO$ m/z=350.1, found m/z=351.0 [M+H]$^+$.

Compound 104b ($R_1$=H; $R_2$=$CH_3$; $R_3$=$CH_3$) $^1$H NMR (300 MHz, MeOH-$d_4$) δ 2.27 (s, 6H), 4.25 (d, J=10.3 Hz, 1H), 4.32 (d, J=10.3 Hz, 1H), 6.64 (s, 3H), 7.41-7.61 (m, 5H). ESI/MS calcd. for $C_{16}H_{18}DNO$ m/z: 242.1, found m/z=243.00 [M+H]$^+$.

Compound 104c ($R_1$=$CH_3$; $R_2$=H; $R_3$=H): $^1$H NMR (300 MHz, MeOH-$d_4$) δ 2.27 (s, 3H), 4.34 (m, 2H), 6.77-7.01 (m, 2H), 7.02-7.30 (m, 2H), 7.30-7.76 (m, 2H). ESI/MS calcd. for $C_{16}H_{18}DNO$ m/z=228.1, found m/z=229.0 [M+H]$^+$.

Compound 104d ($R_1$=$CF_3$; $R_2$=H; $R_3$=H): $^1$H NMR (300 MHz, MeOH-$d_4$) δ 4.47 (broad m, 2H), 7.09-7.20 (m, 1H), 7.24 (d, J=8.2 Hz, 1H), 7.34-7.69 (m, 7H). ESI/MS calculated for $C_{15}H_{13}DF_3NO$ m/z: 282.1, found m/z=283.0 [M+H]$^+$.

Because a prominent route of metabolism of Mexilitene and analogs involves C—H oxidation (alpha to the amine), replacement of the labile C—H bond with C-D decreases metabolism, decreases clearance and increases bioavailability and efficacy (also, see Example 15, below).

In biological testing in cardiomyocytes derived from IPSCs from an LQT3 patient, it was observed that compared to unlabeled compound, deuterium-labeled Mexilitene analogs (e.g., 104a and 104b) showed equal to or greater action potential shortening (Table 1). This result illustrates that deuterium labeling at the alpha position does not change the fundamental pharmacological interaction with the cellular target. However, a kinetic isotope effect on metabolism and decreased clearance of the molecule will be manifested in vivo to improve bioavailability and further improve efficacy.

TABLE 1
Effect of Deuterated and Non-Deuterated Mexilitene Analogs on Cardiomyocytes.

| CPD[a,b] | Structure | WT-EC₅₀ (μM) -Prolong. | WT-Cess. Dose (μM) | WT-Prolong. Dose (μM) | LQT-EC₅₀ (μM)-Shortening | LQT-Cess. Dose (μM) | LQT-Fold Shortening | LQT-Shortening Dose (μM) |
|---|---|---|---|---|---|---|---|---|
| 78 | bis-CF₃ racemic parent | No AP prolongation | 133 | No AP Prolong. | 23.08 | 66 | 1.208 | 22 |
| 104a | bis-CF₃ Deuterated | No AP prolongation | 66 | No AP Prolong. | No AP shortening | 133 | 1.274 | 22 |
| 82 | mono-CF₃ racemic parent | No AP prolongation | 66 | No AP Prolong. | 4.07 | 66 | 1.539 | 22 |

TABLE 1-continued

Effect of Deuterated and Non-Deuterated Mexilitene Analogs on Cardiomyocytes.

| CPD[a,b] | Structure | WT-EC$_{50}$ (μM) -Prolong. | WT-Cess. Dose (μM) | WT-Prolong. Dose (μM) | LQT-EC$_{50}$ (μM)-Shortening | LQT-Cess. Dose (μM) | LQT-Fold Shortening | LQT-Shortening Dose (μM) |
|---|---|---|---|---|---|---|---|---|
| 104d | mono-CF$_3$ Deuterated | No AP prolongation | 22 | No AP Prolong. | (no EC50-but shortens) | 66 | 1.395 | 22 |
| 25 | mono-CH$_3$ racemic parent | 1247 | No EADs | 4.07 | 996.9 | 1.539 | 1.606 | 22 |
| 104c | mono-CH$_3$ Deuterated | No AP prolongation | 66 | No AP Prolong. | No AP shortening | 22 | No AP shortening | No AP shortening |
| 70 | bis-CH$_3$ racemic parent | No AP prolongation | 66 | No AP Prolong. | <0.8 | 66 | 1.279 | 7.4 |
| 104b | bis-CH$_3$ Deuterated | No AP prolongation | 22 | No AP Prolong. | 0.87 | 22 | 1.280 | 2.5 |

[a]No EADs or Spiky Peaks for any compound;
[b]No AP Prolongation for any compound

Example 7: Synthesis of Compounds of Formula III

The pyridinoxy propan-2-amine-based compounds (i.e., 2, 3 or 4-pyridin-ol Mexiletine analogs) of general formula III were synthesized according to the Schemes in Example 3.

Example 8. Metabolic and Chemical Stability

Metabolic Stability Studies in the presence of Rat, Mouse or Human Liver Microsomes or S9.

A typical incubation contained rat, mouse, dog or human liver microsomes (0.4-0.5 mg of protein), 100 mM potassium phosphate buffer (pH7.4), 50 μM test compound, an NADPH-generating system consisting of 0.5 mM NADP$^+$, 0.5 mM glucose-6-phosphate, 1 IU/mL glucose-6-phosphate dehydrogenase, 1 mg/mL diethylenetriaminepentaaceticacid (DETAPAC), and 3 mM MgCl$_2$ in a final incubation volume of 0.25 mL. Incubations were run for 0, 7, 15, 30, and 60 min with constant shaking at 37° C. in a water bath and were terminated by the addition of 0.75 mL cold ACN. After centrifugation at 3000 rpm for 5 min, the organic fraction was collected, the solvent was removed with a stream of argon and the residue was reconstituted in 125 μL of MeOH and 125 μL H$_2$O, mixed thoroughly, centrifuged at 13,000 rpm for 5 min and analyzed by high performance liquid chromatography. Samples were run on a Hitachi D-7000 HPLC system using a L-7100 analytical pump, L-7400 UV-Visible variable wavelength detector, and L-7600 automatic sample injector. A Gemini C18 column (250×4.6 mm, 5 um particle size; Phenomenex,) with a C18 guard column were used for chromatographic separation of the Mexiletine analogs. The mobile phase was an isocratic system using 75% water (0.05% TFA) and 25% acetonitrile (0.05% TFA) with a flow rate of 1.25 mL/min monitored at 275 nm. Disappearance of the analyte was monitored over time. A plot of the area under the curve for the normalized analyte versus time afforded the half-life values and k$_{app}$.

TABLE 1

Metabolic Stability of 25, 70, 78 and 82 in Human, Dog, Mouse and Rat Liver microsomes.

| | Liver Microsomes t$_{1/2}$ (min) | | | |
|---|---|---|---|---|
| Compound | Human | Dog | Mouse | Rat |
| | 104 | 184 | 59 | 52 |

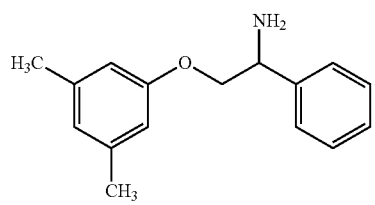

70

TABLE 1-continued

Metabolic Stability of 25, 70, 78 and 82 in Human, Dog, Mouse and Rat Liver microsomes.

| Compound | Liver Microsomes $t_{1/2}$ (min) | | | |
|---|---|---|---|---|
| | Human | Dog | Mouse | Rat |
| 78 (F3C-phenyl-O-CH2-CH(NH2)-phenyl, with CF3 at 3,5-positions) | Stable >95% parent after 60 min | 116 | Stable >95% parent after 60 min | Stable >95% parent after 60 min |
| 25 (2-methylphenyl-O-CH2-CH(NH2)-phenyl) | 141 | Stable >95% parent after 60 min | 208 | 475 |
| 82 (2-CF3-phenyl-O-CH2-CH(NH2)-phenyl) | Stable >95% parent after 60 min | Stable >95% parent after 60 min | 196 | 198 |

The Mexiletine analogs tested (Table 1, above) showed surprising stability in the presence of microsomes that efficiently metabolized testosterone. This is attributed to replacement of the metabolically labile 2,6-dimethyl groups of Mexiletine with metabolically stable CF3- or H-moieties. Unexpectedly, movement of the dimethyl group to the 3,5-position also resulted in a compound that was relatively stable showing the microsomal oxidase(s) that oxidize Mexiletine at the 2,6-dimethyl positions do not efficiently oxidize analogs with substitutions at the 3,5-position. Moving the substituents from the 2,6-positions to the 3,5-positions improves planarity and decreases metabolism. Molecular energy minimization (Avogadro software) of Mexiletine and analogs showed the key dihedral angle of Mexiletine (20.7°) and showed lack of planarity due to an aryl 2,6-dimethyl "gem dimethyl" effect. In contrast, 3- or 5- or 3,5-disubstituted compounds showed a 0° dihedral angle. We hypothesize that 3, 5-aryl-mono or di-substituted Mexiletine analogs possess greater on-target potency and decreased arrhythmogenicity and decreased hepatic microsomal metabolism and better bioavailability.

TABLE 2

STABILITY OF LEAD COMPOUNDS IN S9 FRACTIONS

| Compound | % Metabolism Human S9 | % Metabolism Rat S9 | % Metabolism Dog S9 | % Metabolism Mouse S9 |
|---|---|---|---|---|
| 78 (3,5-bis-CF3-phenyl-O-CH2-CH(NH2)-phenyl) | 41.1 ± 28.9 | 2.1 ± 1.4 | 25.6 ± 17.9 | 11.6 ± 3.0 |

TABLE 2-continued

STABILITY OF LEAD COMPOUNDS IN S9 FRACTIONS

| Compound | % Metabolism Human S9 | % Metabolism Rat S9 | % Metabolism Dog S9 | % Metabolism Mouse S9 |
|---|---|---|---|---|
| 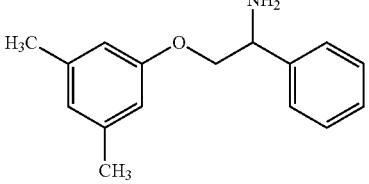 70 | 39.2 ± 8.4 | 45.0 ± 14.5 | 35.8 ± 7.0 | 13.6 ± 5.0 |
| 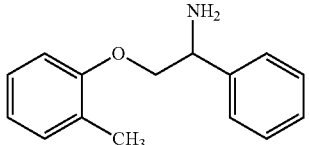 25 | 7.0 ± 0.1 | 97.8 ± 19.5 | 98.0 ± 28.1 | 34.6 |
| 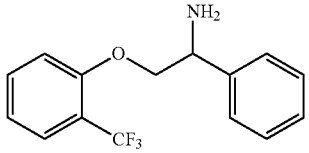 82 | 28.0 ± 7.4 | 15.4 ± 10.5 | 51.0 ± 19.1 | 55.0 ± 22.4 |

Metabolism of Mexiletine analogs in the presence of hepatic S9 from rat, mouse, dog or human (0.5 mg of protein) were conducted as above and analyzed by HPLC as described above. With the possible exception of 25 (in the presence of rat or dog liver S9), the Mexiletine analogs were relatively stable in the presence of S9 (Table 2). Microsomes contain CYPs and FMO metabolic enzymes. S9 contains soluble enzymes (i.e., aldehyde oxidase, MAO, etc.). The data suggests that, unexpectedly, the presence of F-containing substituents decreases metabolism at distal sites due to metabolism by S9 enzymes.

Stability of Mexiletine Analogs at Various Temperatures and pH.

A typical incubation contained 100 μM of the test compound prepared in PBS buffer (pH 7.4 or 3.0, 50 mM) with 1% Ethanol. The test compounds were incubated at 37° C. An aliquot from incubations was taken at various times and injected onto an RP-HPLC system as described above. Disappearance of the analyte was monitored over time. A plot of the area under the curve for the normalized analyte versus time afforded the half-life values and kapp.

TABLE 3

Chemical stability results for Mexiletine Analogs.

| Compound | Half-Life @ pH 7.4 and 37° C. | Half-Life @ pH 3.0 and 37° C. |
|---|---|---|
| 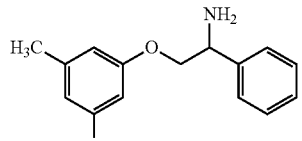 70 | stable > 30 days[a] | stable > 30 days[a] |
| 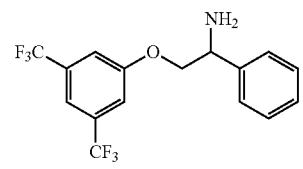 78 | $t_{1/2}$ = 30 days | stable > 30 days[a] |
| 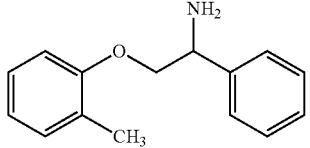 [SMILES: NC(COc1ncccc1C(F)(F)F)c1ccccc1] 25 | stable > 30 day[a] | stable > 15 days[a] |
| 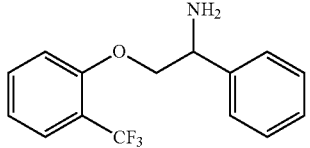 82 | stable > 30 days[a] | stable > 15 days[a] |

[a]No observed change in the parent peak compared to time zero by HPLC analysis.

Chemical stability of the Mexiletine analogs was apparent at pH 7.4 and pH 3 that mimicked the pH of serum and the contents of the gut, respectively (Table 3). The results showed no autooxidation, hydrolysis or other degradation is occurring and the compounds are remarkably stable for extended periods of time (>30 days).

Example 9: In Vivo Studies with Mexilitene Analogs

A prominent adverse reaction in the patient cohort (and others reported in the literature) administered (R)-Mexilitene is nausea and seizures. Because Mexilitene analogs (e.g., 25, 69, 70, 78, 82, 88, 105) possessed Log P values (i.e., 3.2, 4.1, 3.7, 4.5, 2.3, 1.9 and 4.0, respectively) and total polar surface area (PSA $Å^2$ values of 35, 30, 35, 35, 35, 47 and 40, respectively) showing lipophilic and blood brain barrier-penetrating properties, we compared the behavioral properties of the compounds and compared them to Mexilitene. It is known that compounds with PSA less than 60 $Å^2$ and molecular weight below 450 (both observed for the Mexiletene analogs described herein) possess very good GI absorption properties and good CNS-absorption (to treat CNS diseases). Male BALBc mice (20-22 g) were used throughout these studies. The animals were maintained in a temperature-controlled room with 12-hr periods of light and darkness and had continuous access to water and animal food. Mexiletine or Mexiletine analogs showed good water solubility and were dissolved in 10:30:60% DMSO: PEG400:water (v:v) and administered via i.p. injection (5 ml/kg). Groups contained 2-4 animals. Compound treatment was: vehicle or Mexiletine (30 or 100 or 200 mg/kg) or Mexiletine analogs (30 or 100 or 200 mg/kg) administered and monitored for 24 hr after treatment. HBRI compounds (25, 36, 69, 70, 78, 82, 88 or 105) possessed good solubility and were well-tolerated (30-100 mg/kg). For (R)- or (S)- or Racemic Mexiletine, administration of 30 mg/kg produced lethargy and in some cases immobilization. At greater doses (100 or 200 mg/kg), (R)- or Racemic Mexiletine produced seizures and death. (S)-Mexiletine (200 mg/kg) produced lethargy, immobilization and death but severe seizures were not observed. In contrast, mice treated with HBRI compounds 36, 69, 70, or 88 (200 mg/kg) only showed slight lethargy. All behavioral effects subsided after ~45 mins and animals recovered to full activity after 2-3 hours. Both Mexiletine analogs tested and Mexiletine (R→Racemate>S—) produced apparent increase in fast heart rate effects that subsided with time. In conclusion, it was apparent that the Mexiletine analogs tested showed considerably less toxicity (i.e., lack of seizures and death) while preserving cardiovascular effects observed for Mexiletine. The lack of CNS and peripheral (i.e., muscle) toxicity shows that the compounds have utility for CNS diseases such as seizures and epilepsy and other channelopathies.

Example 10: Electrophysiology Studies with Mexilitene Analogs

The basis for LQT3 is a mutation in SCN5a that encodes the voltage-gated Na channel responsible for cardiac action potential. The Na current ($I_{Na}$) has peak and late components: the peak component initiates the action potential but as voltage rises, the channel normally inactivates. The late current is normally a very small portion of the channels that do not inactivate. The LQT3 mutation impairs inactivation. The late component is then enlarged, resulting in action potential prolongation. We identified compounds that more potently and selectively blocked the late current ($I_{NaL}$) in LQT3 patient-derived iPSC-cardiomyocytes. Whole cell patch clamp electrophysiology experiments in LQTS3 cardiomyocytes helped determine the functional activity of drug candidates for inhibition of the late sodium current in the cells. Thus, we tested compounds for Peak ($I_{NaP}$) and Late ($I_{NaL}$) components. They were recorded in a "whole-cell" voltage-clamp mode configuration in response to voltage stimulation steps from −80 mV to +40 mV and their $IC_{50}$ values determined (Table 1). Table 1 is a summary table with the $IC_{50}$ values for peak sodium current ($I_{NaP}$) inhibition, late sodium current ($I_{NaL}$) inhibition and the ratio of the $IC_{50}$ for $I_{NaP}$ inhibition to the $IC_{50}$ for $I_{NaL}$ inhibition. The Peak/Late ratio for 25, 82, 36 and 70 was 60 to 316-fold. This value is similar or greater to that observed measuring the effect on Na ion channels overexpressed in CHO cells (overexpressed $Na_v1.5$ encoded by the LQT3 mutated SCN5A) as presented in Table 1, Example 2, above. Mexiletine has a Peak/Late ratio of ~3. Thus, based on electrophysiology results, our approach of using patient-specific cells has succeeded quite well in producing drug candidates that are much more selective for $I_{NaL}$.

TABLE 1

Effect of Mexiletine Analogs on Electrophysiology in Transfected CHO Cells.

| Compound | $IC_{50}$ for $I_{NaP}$ (µM) | $IC_{50}$ for $I_{NaL}$ (µM) | Ratio $I_{NaP}/I_{NaL}$ | Ratio $Mex^a$ $I_{NaL}$/Lead $I_{NaL}$ | Ratio of Mex Ratio/Lead $Ratio^b$ |
|---|---|---|---|---|---|
| Mexiletine | 145 | 51 | 2.7 | N/A | N/A |
| 25 | 102 | 1.7 | 60 | 30 | 22.3 |
| 82 | 200 | 1.8 | 111 | 28.3 | 41 |
| 36 | 51.8 | 0.38 | 136 | 134.2 | 50 |
| 70 | 171 | 0.54 | 316 | 94.4 | 117 |

The peak current ($I_{NaP}$) mediates cardiac excitability and is an undesired effect of the molecules. Potency at the late current ($I_Na$) is the desired goal. The ratio of the two indicates the selectivity and the $IC_{50}$ indicates the potency of the molecules. Drug candidate (e.g., 36) is as much as 134-fold more potent than racemic mexiletine. Compound 70 is as much as 117-fold more selective than mexiletine. Both metrics show that we have developed significantly more potent and selective inhibitor of $I_{NaL}$ that could be used for the treatment of LQT3 or other indications where $I_{NaL}$ inhibition is the therapeutic target.

Example 11: Metabolism Studies with Mexilitene Analog Enantiomers

Racemic 25, 82, 70 and 78 possessed metabolic stability (in liver microsomes of $T_{1/2}$>60 mins) and chemical stability ($T_{1/2}$>30 days, pH 7.4, 37° C.) (see Example 8). Using the HPLC method described in Example 8, testing metabolism of drug candidate enantiomers showed good metabolic stability. Metabolism of Mexiletine and drug candidates was conducted in human liver S-9 and microsomes, respectively. In good agreement with the literature, Mexiletine was not metabolized very extensively (Table 1). In the presence of S-9, 25, 36 and 70 were detectably metabolized as judged by HPLC. Metabolism was stereoselective with the (R)-enantiomer metabolized greater than the (S)-enantiomer (Table 1). In the presence of human liver microsomes, compounds 82, 70 and 36 were metabolized as judged by HPLC. In good agreement with S-9 studies (above) metabolism was stereoselective, with the (R)-enantiomer greater than the (S)-enantiomer (Table 1).

TABLE 1

Metabolic Stability of Mexiletine and Analogs with Human Liver Preparations

| Compound # | Liver S-9 $T_{1/2}$ | Liver Microsomes $T_{1/2}$ |
| --- | --- | --- |
| (S)-82 | >95% after 1 hr | 365 minutes |
| (R)-82 | >95% after 1 hr | 136 minutes |
| (R)-25 | 408 minutes | >95% after 1 hr |
| (S)-25 | >95% after 1 hr | >95% after 1 hr |
| (R)-70 | 1015 minutes | 406 minutes |
| (S)-70 | >95% after 1 hr | >95% after 1 hr |
| (S)-36 | >95% after 1 hr | >95% after 1 hr |
| (R)-36 | 187 minutes | 175 minutes |
| (R)-78 | >95% after 1 hr | >95% after 1 hr |
| (S)-78 | 1040 minutes | >95% after 1 hr |
| (R)-Mexiletine | >95% after 1 hr | >95% after 1 hr |
| (S)-Mexiletine | >95% after 1 hr | >95% after 1 hr |

It is known that certain CYPs (i.e., CYP3A4 and CYP2D6) play a role in the metabolism of Mexiletine. Accordingly, we examined the metabolism of leads with highly purified CYPs with an HPLC method (Example 8). As shown in Table 2, compared to Mexiletine, minor CYP-dependent metabolism was observed for 82 and 70. The data show analogs 82, 36 and 70 are more metabolically stable than Mexiletine in the presence of highly purified CYP 450. Unexpectedly, Mexiletine was metabolized by FMO (Example 16). It is known that FMO metabolizes primary amines but it was unknown that FMO metabolizes Mexiletine.

TABLE 2

Metabolic Stability of Mexiletine and Rac Compounds with Human Liver Cytochrome P-450a

| | nmols metabolized | nmols/µg CYP | pmols product/µg CYP/min |
| --- | --- | --- | --- |
| Mexilitene | | | |
| CYP3A4 | 32.4 | 2.31 | 46.2 |
| CYP3A5 | 34.2 | 2.44 | 48.8 |
| CYP2D6 | 4.04 | 0.3 | 6.0 |
| Rac 82 | | | |
| CYP3A4 | 10.9 | 0.77 | 15.4 |
| CYP3A5 | 29.9 | 2.13 | 42.6 |
| CYP2D6 | 29.1 | 2.18 | 43.6 |
| Rac 36 | | | |
| CYP3A4 | ND[b] | | ND |
| CYP3A5 | ND | | ND |
| CYP2D6 | ND | | ND |
| Rac 70 | | | |
| CYP3A4 | ND | | ND |
| CYP3A5 | ND | | ND |
| CYP2D6 | 4.6 | .345 | 6.92 |

[a] 50 min incubation,
ND, [b] Not Detectable

Example 12: Behavioral and Safety Studies with Mexilitene Analog Enantiomers

Safety has been established in several enantiomers of drug candidates. The literature states the $LD_{50}$ for Mexiletine in mice is 114 mg/kg. Administration of 200 mg/kg for 25, 82, 70, or 36 enantiomers did not show any lethality. Thus, the $LD_{50}$ is >200 mg/kg for these compounds. In contrast, lethality was observed for Mexiletine at 100 and 200 mg/kg. Thus, the drug candidates examined are safer than Mexiletine.

A prominent adverse reaction in the patient cohort (and others reported in the literature) administered (R)-Mexiletine is nausea and seizures. We compared the behavioral properties of enantiomerically pure drug candidates (i.e., 25, 82, 70, 78 and 36) and compared them to (R)- or (S)-Mexiletine at 100 mg/kg (Table 1). Drug candidate enantiomers (i.e., enantiomers of 25, 82, 70, 78 and 36) were well-tolerated in vivo (100 mg/kg) in terms of behavioral effects (or lack thereof). In contrast, for (R)-Mexiletine, administration of 100 mg/kg produced immobilization, seizures and death. (S)-Mexiletine (100 mg/kg) produced lethargy and immobilization but severe seizures were not observed. In contrast, mice treated with drug candidate enantiomer (R)-82, 70, or 78 (100 mg/kg) unexpectedly showed no apparent behavioral effects. Minor lethargy was observed for (S)-25, 82, 70 and 78. Thus, adverse behavioral effects were stereoselective (adverse effects S→R—). In conclusion, compared to Mexiletine, it was apparent that (R)-enantiomer drug candidate compounds examined showed considerably less toxicity (i.e., seizures and death) than that observed for Mexiletine enantiomers.

TABLE 1

Effect of Stereochemistry on Behavioral Effects of Mexiletine Analogs.

| Compound | Behavior Effect[a] (R)-enantiomer | Behavior Effect[a] (S)-enantiomer |
| --- | --- | --- |
| 82 | No detectable effect | 2/4 slightly lethargic |
| 70 | No detectable effect | 2/4 lethargic |
| 78 | No detectable effect | 2/4 shaking |
| 36 | 3/4 immobilized | No detectable effect |
| 25 | 4/4 immobilized | 3/4 immobilized |
| Mexilitene | 1 seizure, 1 death, 2 immobilized | 4/4 immobilized |

Example 13: Effect of Pyridyl-Mexiletine Derivatives on WT and LQT-3 Cardiomyocytes Pyridyl-Mexiletines moderate potency for LQT-3 shortening. Two most effective compounds, (i.e., unsubstituted 4-pyridyl (i.e., 126) and ortho-methyl-3-pyridyl compounds (i.e., 111), showed shortening EC50 values of approximately 4 and 8 µM, respectively. The unsubstituted 3-pyridyl derivative (i.e., 121) with the N-methoxy ethyl modification also showed moderate shortening in LQT-3 cells (Table 1).

TABLE 1

Effect of Pyridyl-Mexiletine derivatives on WT and LQT-3 Cardiomyocytes.

| Compound Number | Structure | WT-EC$_{50}$ (µM) Prolongation | WT-Cessation Dose (µM) | LQT-EC$_{50}$ (µM) Shortening | LQT-Fold Shortening | LQT-Shortening Dose (µM) |
|---|---|---|---|---|---|---|
| 19 | pyridyl-CH$_3$-O-CH$_2$-C(=NOBn)-Ph | Does Not Prolong AP | 133 | 1.38 | 1.406 | 66 |
| 20 | pyridyl-O-CH$_2$-CH(NH$_2$)-Ph | Does Not Prolong AP | No cessation of beating | Does Not Shorten | Does Not Shorten | Does Not Shorten |
| 48 | pyridyl-O-CH$_2$-CH(NH$_2$)-CH$_3$ | Does Not Prolong AP | No cessation of beating | Does Not Shorten | Does Not Shorten | Does Not Shorten |
| 94 | pyridyl-CH$_3$-O-CH$_2$-CH(NH$_2$)-Ph | 18.48 | No cessation of beatimg | 12.82 | 1.287 | 66 |
| 96 | pyridyl-CF$_3$-O-CH$_2$-CH(NH$_2$)-Ph | Does Not Prolong AP | No cessation of beating | 20.7 | 1.358 | 133 |

TABLE 2

Effect of 3-Pyridyl-Mexiletine derivatives on WT and LQT-3 Cardiomyocytes

| Compound Number | Structure | WT-EC$_{50}$ (µM) Prolongation | WT-Cessation Dose (µM) | LQT-EC$_{50}$ (µM) Shortening | LQT-Fold Shortening | LQT-Shortening Dose (µM) |
|---|---|---|---|---|---|---|
| 110 | 3-pyridyl-O-CH$_2$-CH(NH$_2$)-Ph | 33.76 | No cessation of beating | 62.56 (Prolongation and EADs) | 1.546 (Prolongation) | 133 |
| 111 | 3-pyridyl-CH$_3$-O-CH$_2$-CH(NH$_2$)-Ph | Does Not Prolong AP | 133 | 8.57 | 1.426 | Does Not Shorten |

TABLE 2-continued

Effect of 3-Pyridyl-Mexiletine derivatives on WT and LQT-3 Cardiomyocytes

| Compound Number | Structure | WT-EC$_{50}$ (μM) Prolongation | WT-Cessation Dose (μM) | LQT-EC$_{50}$ (μM) Shortening | LQT-Fold Shortening | LQT-Shortening Dose (μM) |
| --- | --- | --- | --- | --- | --- | --- |
| 112 | 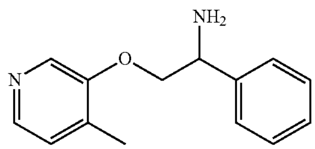 [SMILES: Cc1ccncc1OCC(N)c1ccccc1] | 19.4 | No cessation of beating | Does Not Shorten | Does Not Shorten | Does Not Shorten |
| 113 | 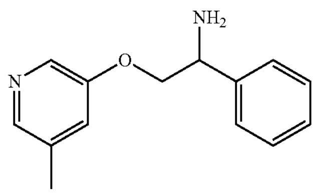 [SMILES: Cc1cncc(OCC(N)c2ccccc2)c1] | 7.24 | 200 | Does Not Shorten | Does Not Shorten | Does Not Shorten |
| 114 | 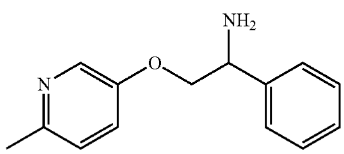 [SMILES: Cc1ccc(OCC(N)c2ccccc2)cn1] | Does Not Prolong AP | No cessation of beating | 67.5 | 1.233 | 22 |
| 115 | 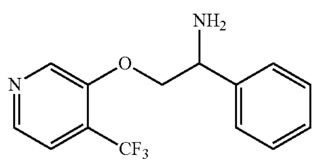 | 25.7 | No cessation of beating | Does Not Shorten | Does Not Shorten | Does Not Shorten |
| 116 | 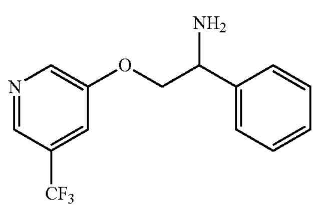 | Does Not Prolong AP | 200 | Shortens | 1.422 | 22 |
| 117 | 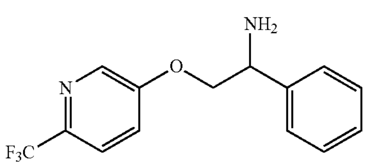 [SMILES: NC(COc1ccc(C(F)(F)F)nc1)c1ccccc1] | Does Not Prolong AP | 66 | Does Not Shorten | Does Not Shorten | Does Not Shorten |
| 118 | 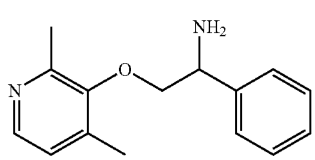 [SMILES: Cc1ccnc(C)c1OCC(N)c1ccccc1] | 8.22 | No cessation of beating | Does Not Shorten | Does Not Shorten | Does Not Shorten |
| 119 | 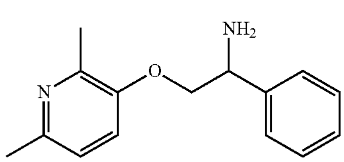 [SMILES: Cc1ccc(OCC(N)c2ccccc2)c(C)n1] | Does Not Prolong AP | No cessation of beating | Shortens | 1.123 | 22 |

TABLE 2-continued

Effect of 3-Pyridyl-Mexiletine derivatives on WT and LQT-3 Cardiomyocytes

| Compound Number | Structure | WT-EC$_{50}$ (μM) Prolongation | WT- Cessation Dose (μM) | LQT-EC$_{50}$ (μM) Shortening | LQT-Fold Shortening | LQT- Shortening Dose (μM) |
| --- | --- | --- | --- | --- | --- | --- |
| 120 | 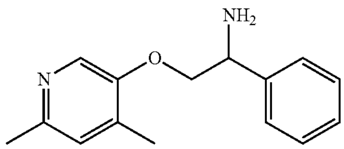 [SMILES: Cc1cc(C)c(OCC(N)c2ccccc2)cn1] | 7.33 | No cessation of beating | Does Not Shorten | Does Not Shorten | Does Not Shorten |
| 121 | 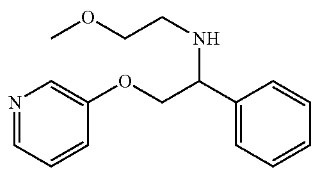 [SMILES: COCCNC(COc1cccnc1)c1ccccc1] | 25.42 | No cessation of beating | 2.58 | 1.144 | 22 |
| 122 | 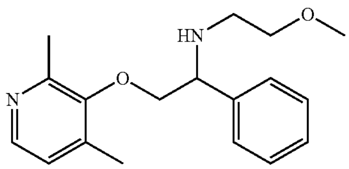 [SMILES: COCCNC(COc1c(C)ccnc1C)c1ccccc1] | Does Not Prolong AP | 200 | 46.57 | 1.188 | 66 |
| 123 | 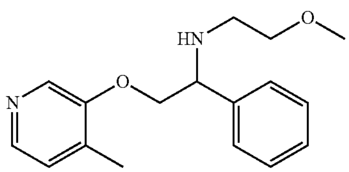 [SMILES: COCCNC(COc1cnccc1C)c1ccccc1] | Does Not Prolong AP | 200 | Shortens | 1.402 | 66 |
| 124 | 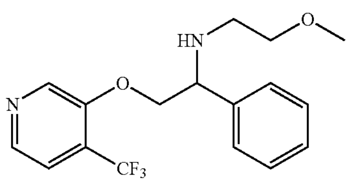 [SMILES: COCCNC(COc1cnccc1C(F)(F)F)c1ccccc1] | Does Not Prolong AP | 66 | Shortens | 1.601 | 7.4 |
| 125 | 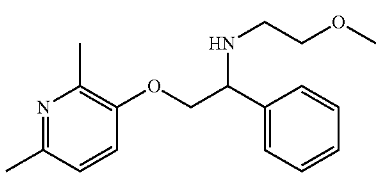 | Does Not Prolong AP | 66 | Does Not Shorten | Does Not Shorten | Does Not Shorten |

TABLE 3

Effect of 4-Pyridyl-Mexiletine derivatives on WT and LQT-3 Cardiomyocytes

| Compound Number | Structure | WT-EC$_{50}$ (μM) Prolongation | WT- Cessation Dose (μM) | LQT-EC$_{50}$ (μM) Shortening | LQT- Fold Shortening | LQT- Shortening Dose (μM) |
| --- | --- | --- | --- | --- | --- | --- |
| 126 | 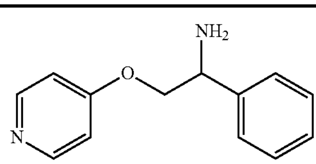 | Does Not Prolong AP | No cessation of beating | 3.82 | 1.281 | 7.4 |

TABLE 3-continued

Effect of 4-Pyridyl-Mexiletine derivatives on WT and LQT-3 Cardiomyocytes

| Compound Number | Structure | WT-EC$_{50}$ (µM) Prolongation | WT- Cessation Dose (µM) | LQT-EC$_{50}$ (µM) Shortening | LQT- Fold Shortening | LQT- Shortening Dose (µM) |
|---|---|---|---|---|---|---|
| 127 | (structure) | 97.68 | No cessation of beating | Does Not Shorten | Does Not Shorten | Does Not Shorten |
| 128 | (structure) | Does Not Prolong AP | No cessation of beating | Shortens | 1.226 | 22 |

Example 14: Naphthalene Derivatives of Mexiletine and Analogs

Naphthalene derivatives of Mexiletine and several lead compounds bearing phenol substitution were synthesized following the previously described method (Scheme 1, Example 3) and obtained in good yield and excellent purity. Naphthalene analogs of Mexiletine and the lead compounds showed potency with significant LQT-3 shortening. Although the shortening EC$_{50}$ was generally greater than the corresponding phenyl analogs, the cessation dose was also increased. The most potent bicyclic compound tested contained 1-naphthol as a phenol moiety analog, consistent with the hypothesis that this would be highly potent given the structural similarity to analogs with 2,3-dimethyl phenol substituents (e.g., 30-36). Although showing some prolongation effects in wild type cells, the mono-trifluoromethyl naphtha-Mexiletine compound (i.e., 134) was highly potent and did not induce cessation of beating at the concentrations examined.

TABLE 1

Effect of Naphtha-Mexiletine derivatives on WT and LQT-3 Cardiomyocytes.

| Compound Number | Structure | WT-EC$_{50}$ (µM) Prolongation | LQT-EC$_{50}$ (µM) Shortening | LQT- Cessation Dose (µM) | LQT- Fold Shortening | LQT- Shortening Dose (µM) |
|---|---|---|---|---|---|---|
| 129 | (structure) | Does Not Prolong AP | 0.82 | 66 | 1.316 | 2.5 |
| 130 | (structure) | Does Not Prolong AP | 8.7 | 133 | 1.459 | 66 |

TABLE 1-continued

Effect of Naphtha-Mexiletine derivatives on WT and LQT-3 Cardiomyocytes.

| Compound Number | Structure | WT-EC$_{50}$ (μM) Prolongation | LQT-EC$_{50}$ (μM) Shortening | LQT- Cessation Dose (μM) | LQT- Fold Shortening | LQT- Shortening Dose (μM) |
|---|---|---|---|---|---|---|
| 131 | 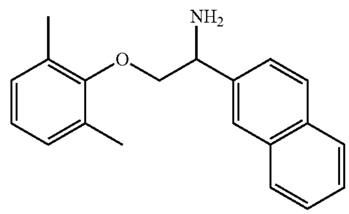 [SMILES: Cc1cccc(C)c1OCC(N)c1ccc2ccccc2c1] | Does Not Prolong AP | 4.73 | 133 | 1.309 | 22 |
| 132 | 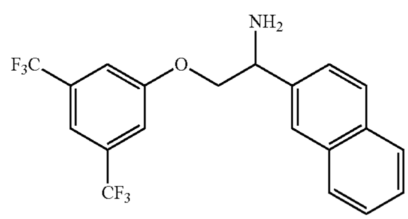 [SMILES: NC(COc1cc(C(F)(F)F)cc(C(F)(F)F)c1)c1ccc2ccccc2c1] | Does Not Prolong AP | Shortens | No cessation of beating | 1.205 | 133 |
| 133 | 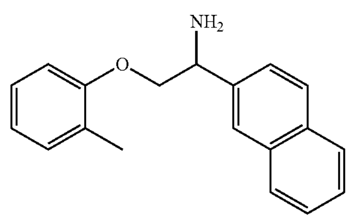 [SMILES: Cc1ccccc1OCC(N)c1ccc2ccccc2c1] | Does Not Prolong AP | 8.83 | 133 | 1.302 | 22 |
| 134 | 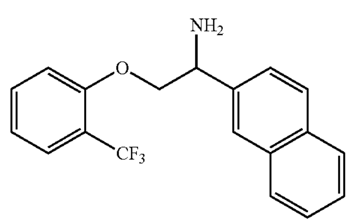 [SMILES: NC(COc1ccccc1C(F)(F)F)c1ccc2ccccc2c1] | 24.40 | 1.79 | No cessation of beating | 1.515 | 133 |
| 135 | 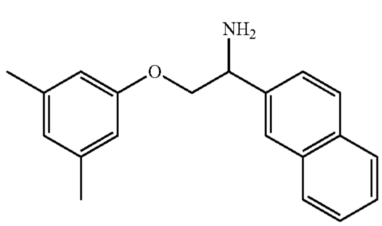 [SMILES: Cc1cc(C)cc(OCC(N)c2ccc3ccccc3c2)c1] | Does Not Prolong AP | Shortens | 200 | 1.667 | 133 |

Example 15: Metabolism of Deuterated Mexiletine Analogs

As discussed above (Example 6), deuterated Mexiletine analogs were synthesized and tested in hepatic preparations or enzymes to determine if deuteration would decrease metabolism compared to Mexiletine. Compared to Mexiletine, data of Table 1, below, shows that the deuterated analogs were in general, more metabolically stable. In many cases, an apparent large isotope effect is apparent for the deuterated compounds compared to non-deuterated Mexiletine.

TABLE 1

Effect of Metabolism on Deuterated Analogs and unlabeled Mexiletine.

| Compound | Mouse liver S-9 (nmol/incub)$^a$ | Human FMO1 (nmol/incub)$^b$ | Human FMO3 (nmol/incub)$^b$ | Human CYP3A4 (nmol/incub)$^c$ |
|---|---|---|---|---|
| Mexiletine | 5.2 | 6.7 | ND$^d$ | 3.0 |
| 104a | ND$^d$ | 0.8 | 0.6 | 1.1 |
| 104c | 13.2 | 1.4 | 1.3 | 1.0 |
| 104d | ND | 0.3 | 0.7 | 0.3 |
| 104b | ND | 1.0 | 0.05 | 0.3 |

$^a$0.4 mg protein/incubation;
$^b$15 µg enzyme/incubation;
$^c$3 pmol enzyme/incubation;
$^d$ND, no detectable decrease.
Incubations were run for 30 mins with shaking at 37° C. Expressed as nmol metabolism/incubation.

As a further example, the metabolism of Mexiletine was compared to deuterated Mexiletine (135) and Phenyl Mexiletine was compared with deuterated Phenyl Mexiletine (136), (compounds in Example 3). As shown in Table 2, generally, compounds with deuterium (i.e., 135 and 136) showed large and unexpected isotope effects on metabolism. This will translate to a large isotope effect on in vivo metabolism, a decrease in clearance, greater bioavailability and longer efficacy. This will result in a more long-lived human drug resulting in fewer doses/day and less side effects and greater efficacy.

TABLE 2

Effect of Metabolism on Deuterated Mexiletine and Phenyl Mexiletine.

| | Condition | | | |
|---|---|---|---|---|
| | Mexiletine nmol metab./ incub. | D$^d$- Mexiletine nmol metab./ incub. | Phenyl Mexiletine nmol metab./ incub. | D$^d$-Phenyl Mexiletine nmol metab./ incub. |
| Mouse S-9$^a$ | 8.0 | 3.9 | 2.5 | 1.4 |
| Human S-9$^a$ | 3.9 | 2.7 | 1.2 | 1.4 |
| Human FMO1$^b$ | 2.4 | 1.4 | 0.33 | 0.06 |
| Human CYP3A4$^c$ | 4.1 | 5.2 | 2.3 | 1.5 |

$^a$0.4 mg protein/incubation;
$^b$15 µg enzyme/incubation;
$^c$3 pmol enzyme/incubation;
Incubations were run for 30 mins with shaking at 37° C. and results are in nmol of metabolism/incubation,
$^d$D stands for deuterium.

Figure 2:
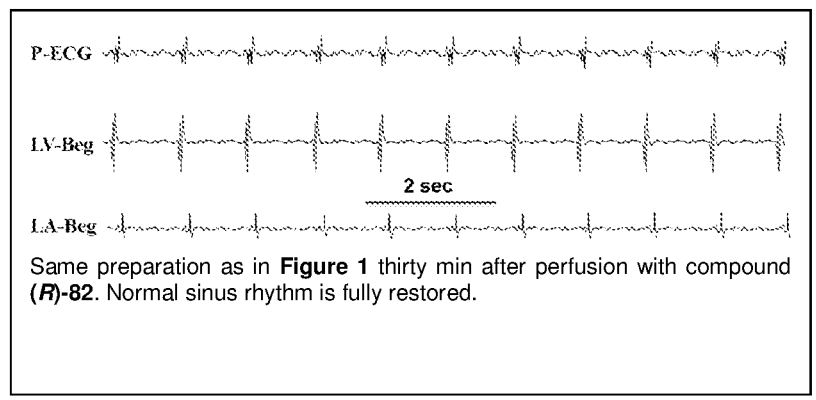
FIG. 2. Complete resolution of all forms of arrhythmias to normal sinus rhythm 30 min after perfusion of Compound (R)-82 (10 µM) in an Isolated Perfused Aged Heart in the presence of hydrogen peroxide.

Example 16. Effect of (R)-82 on an Aged Rat Heart Perfusion Model of Arrhythmia Conduction velocity (CV), action potential duration (APD) and responsiveness to drugs was measured in ex-vivo rat heart preparations (FIG. 1). We chose a rat heart model to test for the effect of (R)-82 (i.e., (R)-Dd, Example 4) to decrease arrhythmias because CV and APD are preserved in buffer-perfused rat hearts up to 2 days. In contrast, in this model, continuous presence (perfusion) of H$_2$O$_2$ (0.1 mM) produces early after depolarizations (EADs) and ectopic ventricular beats 6 min after exposure that degenerates to ventricular tachycardia (VT) and ventricular fibrillation (VF) after 12 min (FIG. 1). Left untreated, the heart would die within 45 mins. Using this preparation, complete resolution of all forms of arrhythmias to normal sinus rhythm was observed 30 min after perfusion of compound (R)-82 (10 VM) in the continuous presence of H$_2$O$_2$ (0.1 mM) (FIG. 2). This shows that administration of (R)-82 (i.e., (R)-Dd, Example 4) to a heart suffering from severe arrhythmias potently reverses VT and VF and corrects EADs in a very clinically relevant short time. The effect of (R)-82 is similar to or more potent than the effect of ranolazine (10 M) in the same ex vivo model. The conclusion is that (R)-82 is more efficacious than the currently used standard of care.

What is claimed is:
1. A compound of Formula I:

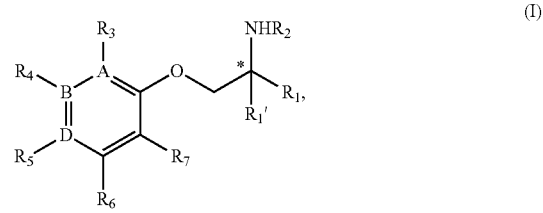

or a salt thereof,
wherein:
A, B, D are each Carbon;
R$_1$ is selected from the group consisting of methyl, trideuteromethyl, (C$_2$-C$_6$)alkyl, (C$_3$-C$_6$)cycloalkyl, phenyl, (C$_6$-C$_{24}$)aryl, and (C$_5$-C$_{24}$)heteroaryl, wherein (C$_6$-C$_{24}$)aryl and (C$_6$-C$_{24}$)heteroaryl are optionally substituted with 1 or 2 R$_8$ substituents, wherein each R$_8$ substituent is independently selected from the group consisting of deuterium, halo, methyl, trideuteromethyl, trifluoromethyl, 2,2,2-trifluoroethyl, (C$_2$-C$_6$)alkyl, (C$_3$-C$_6$)cycloalkyl, (C$_1$-C$_6$)alkyloxy, (C$_3$-C$_6$)cycloalkyloxy, amino, (C$_1$-C$_6$)alkylamino, di-(C$_1$-C$_6$)alkylamino, (C$_6$-C$_{24}$)arylamino, cyano, nitro, and (C$_1$-C$_6$)alkylsulfonyl;
R$_1$' is deuterium;
R$_2$ is selected from the group consisting of hydrogen, deuterium, methyl, trideuteromethyl, trifluoromethyl, 2,2,2-trifluoroethyl, (C$_2$-C$_6$)alkyl, (C$_3$-C$_6$)cycloalkyl, (C$_3$-C$_6$)cycloheteroalkyl, 2-(C$_1$-C$_6$)alkoxyethyl, 2-hydroxyethyl, 2-(C$_6$-C$_{24}$)aryloxyethyl, bis(2-methoxyethyl), (C$_1$-C$_6$)alkoxymethyl, 2-(C$_3$-C$_6$)cycloalkoxyethyl, (C$_6$-C$_{24}$)aryl, and (C$_6$-C$_{24}$)heteroaryl, wherein (C$_6$-C$_{24}$)aryl and (C$_6$-C$_{24}$)heteroaryl are optionally substituted with 1 to 2 R$_8$ substituents selected from the group consisting of deuterium, halo, methyl, trideuteromethyl, trifluoromethyl, 2,2,2-trifluoroethyl, (C$_2$-C$_6$) alkyl, (C$_3$-C$_6$)cycloalkyl, (C$_1$-C$_6$)alkyloxy, (C$_3$-C$_6$)cycloalkyloxy, amino, (C$_1$-C$_6$)alkylamino, di-(C$_1$-C$_6$) alkylamino, (C$_6$-C$_{24}$)arylamino, cyano, nitro and and (C$_1$-C$_6$)alkylsulfonyl;
R$_3$ is selected from the group consisting of hydrogen, deuterium, halo, methyl, trideuteromethyl, trifluoromethyl, 2,2,2-trifluoroethyl, $(C_2-C_6)$alkyl, $(C_3-C_6)$cycloalkyl, $(C_1-C_6)$alkyloxy, $(C_3-C_6)$cycloalkyloxy, amino, $(C_1-C_6)$alkylamino, di-$(C_1-C_6)$alkylamino, $(C_6-C_{24})$arylamino, cyano, nitro, and $(C_1-C_6)$alkylsulfonyl;

$R_4$ is selected from the group consisting of hydrogen, deuterium, halo, methyl, trideuteromethyl, trifluoromethyl, 2,2,2-trifluoroethyl, $(C_2-C_6)$alkyl, $(C_3-C_6)$cycloalkyl, $(C_1-C_6)$alkyloxy, $(C_3-C_6)$cycloalkyloxy, amino, $(C_1-C_6)$alkylamino, di-$(C_1-C_6)$alkylamino, $(C_6-C_{24})$arylamino, cyano, nitro, and $(C_1-C_6)$alkylsulfonyl;

$R_5$ is selected from the group consisting of hydrogen, deuterium, halo, methyl, trideuteromethyl, trifluoromethyl, 2,2,2-trifluoroethyl, $(C_2-C_6)$alkyl, $(C_3-C_6)$cycloalkyl, $(C_1-C_6)$alkyloxy, $(C_3-C_6)$cycloalkyloxy, amino, $(C_1-C_6)$alkylamino, di-$(C_1-C_6)$alkylamino, $(C_6-C_{24})$arylamino, cyano, nitro, and $(C_1-C_6)$alkylsulfonyl;

$R_6$ and $R_7$ are independently selected from the group consisting of hydrogen, deuterium, halo, methyl, trideuteromethyl, trifluoromethyl, 2,2,2-trifluoroethyl, $(C_2-C_6)$alkyl, $(C_3-C_6)$cycloalkyl, $(C_1-C_6)$alkyloxy, $(C_3-C_6)$cycloalkyloxy, amino, $(C_1-C_6)$alkylamino, di-$(C_1-C_6)$alkylamino, $(C_6-C_{24})$arylamino, cyano, nitro, and $(C_1-C_6)$alkylsulfonyl; and wherein the indicated (*) carbon atom is in the R- or S-configuration.

2. The compound of claim 1 wherein the compound is of Formula Ia:

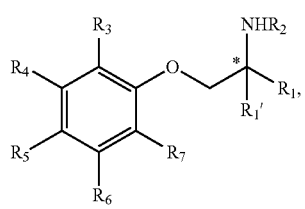

(Ia)

or a salt thereof,
wherein:
$R_1$ is selected from the group consisting of methyl, trideuteromethyl, $(C_2-C_6)$alkyl, $(C_3-C_6)$cycloalkyl, phenyl, $(C_6-C_{24})$aryl, and $(C_5-C_{24})$heteroaryl, wherein $(C_6-C_{24})$aryl and $(C_6-C_{24})$heteroaryl are optionally substituted with 1 or 2 $R_8$ substituents, wherein each $R_8$ substituent is independently selected from the group consisting of deuterium, halo, methyl, trideuteromethyl, trifluoromethyl, 2,2,2-trifluoroethyl, $(C_2-C_6)$alkyl, $(C_3-C_6)$cycloalkyl, $(C_1-C_6)$alkyloxy, $(C_3-C_6)$cycloalkyloxy, amino, $(C_1-C_6)$alkylamino, di-$(C_1-C_6)$alkylamino, $(C_6-C_{24})$arylamino, cyano, nitro, and $(C_1-C_6)$alkylsulfonyl;

$R_1'$ is deuterium;

$R_2$ is selected from the group consisting of hydrogen, deuterium, methyl, trideuteromethyl, trifluoromethyl, 2,2,2-trifluoroethyl, $(C_2-C_6)$alkyl, $(C_3-C_6)$cycloalkyl, $(C_3-C_6)$cycloheteroalkyl, 2-$(C_1-C_6)$alkoxyethyl, 2-hydroxyethyl, 2-$(C_6-C_{24})$aryloxyethyl, bis(2-methoxyethyl), $(C_1-C_6)$alkoxymethyl, 2-$(C_3-C_6)$cycloalkoxyethyl, $(C_6-C_{24})$aryl, and $(C_6-C_{24})$heteroaryl, wherein $(C_6-C_{24})$aryl and $(C_6-C_{24})$heteroaryl are optionally substituted with 1 or 2 $R_8$ substituents, wherein each $R_8$ substituent is selected from the group consisting of deuterium, halo, methyl, trideuteromethyl, trifluoromethyl, 2,2,2-trifluoroethyl, $(C_2-C_6)$alkyl, $(C_3-C_6)$cycloalkyl, $(C_1-C_6)$alkyloxy, $(C_3-C_6)$cycloalkyloxy, amino, $(C_1-C_6)$alkylamino, di-$(C_1-C_6)$alkylamino, $(C_6-C_{24})$arylamino, cyano, nitro and $(C_1-C_6)$alkylsulfonyl; and $R_3$, $R_4$, $R_5$ and $R_6$ are independently selected from the group consisting of hydrogen, methyl and trifluoromethyl.

3. The compound of claim 2 wherein the compound is:

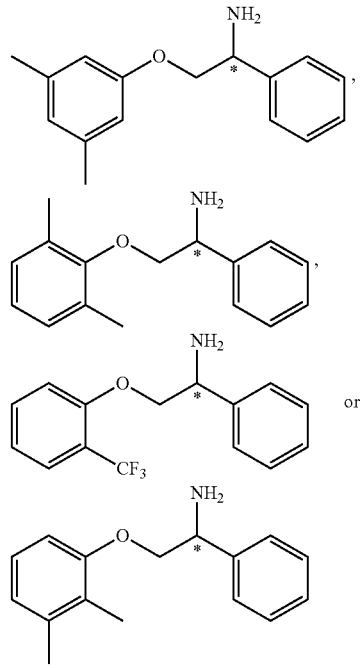

or a salt thereof.

4. The compound of claim 2 wherein the compound is:

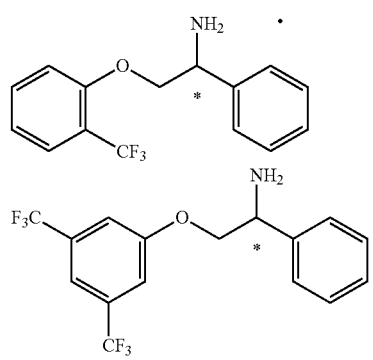

or a salt thereof.

5. The compound of claim 1 wherein the compound salt is that of a pharmaceutically acceptable salt wherein the pharmaceutically acceptable salt is an acid addition salt from hydrochloric, hydrobromic, phosphoric, phosphonic, nitric, sulfuric, acetic, chloroacetic, dichloroacetic, trichloroacetic, triflouroacetic, oxalic, maleic, mandelic, malonic, citric, tartaric, fumaric, salicylic, methanesulfonic, benzenesulfonic, toluenesulfonic, or 2,6-dimethylbenzenesulfonic acid.

6. The compound of claim 1, wherein the compound is in the R-configuration at the indicated (*) carbon atom.

7. A composition comprising a compound of claim 1 and one, two, three or more compounds independently selected from the group consisting of anesthetics, anti-arrhythmics, anticonvulsants, anti-antiarrhythmic peptides, anti-antiarrhythmic growth factors, anti-antiarrhythmic proteins, anti-antiarrhythmic drug-peptide conjugates, antibody-drug conjugates, vitamins, and nutraceuticals.

8. A drug delivery system for a compound of claim 1, wherein the drug delivery system is comprised of a component selected from the group consisting of pharmaceutically accepted polymers, collagen, modified collagens, thrombin-collagen gels, starches, modified starches, gels, hydrogels, pastes, colloids, suspensions, encapsulants, cyclodextrins, micelles, vesicles, and liposomes.

9. A composition comprising a compound of claim 1 and isolated cells capable of acting on functional muscle cells, neuronal cells or cells of the central nervous system.

10. The composition of claim 9 wherein the cells are progenitor cells or stem cells of induced, embryonic or adult origin.

11. A method of inhibiting sodium channels in animal cells found in living organisms or in isolated tissue cells comprising the step of contacting said cells with an effective amount of a compound of claim 1.

12. The method of claim 11 wherein inhibition of said sodium channels in animal cells modulate membrane potential, action potential or physiological function wherein the animal cells are those of heart, brain, muscle, or central nervous system, or are peripheral cells.

13. The method of claim 12, wherein the heart, brain, muscle, central nervous system, or peripheral cells are mature cells or progenitor cells.

14. The method of claim 13 wherein the progenitor cells are stem cells of induced, embryonic or adult origin.

15. A method of inhibiting sodium channels in mammalian cells comprising the step of co-contacting the mammalian cells with an effective amount of a compound of claim 1 and an effective amount of an anti-arrhythmic drug.

16. The method of claim 15, wherein the anti-arrhythmic drug is an ion channel inhibitor or agonist.

17. The method of claim 16 wherein the anti-arrhythmic drug is a Class 1, Class 2, Class 3, Class 4 or Class 5 anti-arrhythmic drug.

18. A method of inducing anesthetic, anti-arrhythmic, anticonvulsant or anti-hyperexcitability therapeutic effects in a subject in need thereof comprising the steps of:
(a) contacting isolated progenitor cells or stem cells of induced, embryonic cells or adult origin cells with an effective amount of a compound of claim 1, and (b) administering an effective number of cells of step (a) to the subject, OR comprising the step of:
(a') co-administering an effective number of isolated progenitor cells or stem cells of induced, embryonic cells or adult origin cells and an effective amount of a compound of claim 1 to the subject.

19. A method of inducing anesthetic, anti-arrhythmic, anticonvulsant or anti-hyperexcitability therapeutic effects in a subject in need thereof comprising the steps of:
(a) co-contacting isolated progenitor cells or stem cells of induced, embryonic cells or adult origin cells with an effective amount of a compound of claim 1 and an effective amount of a chemical or biological agent selected from the group consisting of anesthetics, anti-arrhythmics, anticonvulsants, drugs, small molecules with ion channel antagonist effects, small molecules with ion channel agonist effects, anti-antiarrhythmic peptides, anti-antiarrhythmic growth factors, anti-antiarrhythmic proteins, anti-antiarrhythmic drug-peptide conjugates, antibody-drug conjugates, vitamins, and nutraceuticals, and
(b) administering an effective number of cells of step (a) to the subject, OR, comprising the step of:
(a') co-administering to the subject an effective number of isolated cells and an effective amount of a compound of claim 1 and an effective amount of a chemical or biological agent selected from the group consisting of anesthetics, anti-arrhythmics, anticonvulsants, drugs, small molecules with ion channel antagonist effects, small molecules with ion channel agonist effects, anti-antiarrhythmic peptides, anti-antiarrhythmic growth factors, anti-antiarrhythmic proteins, anti-antiarrhythmic drug-peptide conjugates, antibody-drug conjugates, vitamins, and nutraceuticals.

20. A method for therapeutic modulation of a channelopathy or to induce anesthesia in a subject, comprising the step of administering an effective amount of a compound of claim 1 to the subject.

21. The method of claim 20 wherein the channelopathy is a cardiac arrhythmia or amyotrophic lateral sclerosis or seizures.

* * * * *